United States Patent
Harris et al.

(10) Patent No.: US 9,713,468 B2
(45) Date of Patent: Jul. 25, 2017

(54) SURGICAL STAPLER FOR APPLYING A LARGE STAPLE THROUGH A SMALL DELIVERY PORT AND A METHOD OF USING THE STAPLER TO SECURE A TISSUE FOLD

(75) Inventors: Jason L. Harris, Mason, OH (US); Lawrence Crainich, Charlestown, NH (US); Michael J. Stokes, Cincinnati, OH (US); Mark S. Zeiner, Mason, OH (US); Darrel M. Powell, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1810 days.

(21) Appl. No.: 12/608,860

(22) Filed: Oct. 29, 2009

(65) Prior Publication Data
US 2010/0191282 A1   Jul. 29, 2010

Related U.S. Application Data

(63) Continuation-in-part of application No. 12/359,351, filed on Jan. 26, 2009, and a continuation-in-part of
(Continued)

(51) Int. Cl.
*A61B 17/10*     (2006.01)
*A61B 17/064*    (2006.01)
(Continued)

(52) U.S. Cl.
CPC ...... *A61B 17/0644* (2013.01); *A61B 17/0682* (2013.01); *A61B 2017/00818* (2013.01);
(Continued)

(58) Field of Classification Search
CPC . A61B 17/068; A61B 17/0682; A61B 17/072; A61B 17/07207
(Continued)

(56) References Cited

U.S. PATENT DOCUMENTS 2,185,518 A    1/1940  Posnack
3,193,165 A    7/1965  Akhalaya et al.
(Continued)

FOREIGN PATENT DOCUMENTS

CN    86106345       7/1987
DE    2348670 A1     4/1974
(Continued)

OTHER PUBLICATIONS

International Search Report dated Apr. 7, 2011 (PCT/US2011/020472).
(Continued)

*Primary Examiner* — Melanie Tyson

(57) ABSTRACT

A method of deploying a surgical fastener into a patient by introducing the fastener into a body of a patient while the fastener is in a first shape having a first loop with a back span and an original size and shape. The method then involves moving end segments of the fastener away from each other substantially along an entire length thereof while keeping the back span in substantially its original size and shape. The method then involves forming the fastener into a second loop having a width greater than a width of the first loop.

10 Claims, 79 Drawing Sheets

Related U.S. Application Data application No. 12/359,354, filed on Jan. 26, 2009, and a continuation-in-part of application No. 12/359,357, filed on Jan. 26, 2009.

(51) Int. Cl.
- *A61B 17/068* (2006.01)
- *A61B 17/00* (2006.01)
- *A61B 17/29* (2006.01)

(52) U.S. Cl.
CPC ............ *A61B 2017/2925* (2013.01); *A61B 2017/2946* (2013.01)

(58) Field of Classification Search
USPC ...................................................... 606/143
See application file for complete search history.

(56) References Cited

U.S. PATENT DOCUMENTS

| | | |
|---|---|---|
| 3,552,626 A | 1/1971 | Astafiev et al. |
| 3,638,847 A | 2/1972 | Noiles et al. |
| 3,740,994 A | 6/1973 | DeCarlo, Jr. et al. |
| 3,819,100 A | 6/1974 | Noiles et al. |
| 4,086,926 A | 5/1978 | Green et al. |
| 4,289,133 A | 9/1981 | Rothfuss |
| 4,331,276 A | 5/1982 | Bourque |
| 4,396,139 A | 8/1983 | Hall et al. |
| 4,407,286 A | 10/1983 | Noiles et al. |
| 4,430,997 A | 2/1984 | DiGiovanni et al. |
| 4,456,161 A | 6/1984 | Russell |
| 4,485,817 A | 12/1984 | Swiggett |
| 4,489,875 A | 12/1984 | Crawford et al. |
| 4,505,273 A | 3/1985 | Braun et al. |
| 4,509,518 A | 4/1985 | McGarry et al. |
| 4,522,207 A | 6/1985 | Klieman et al. |
| 4,624,254 A | 11/1986 | McGarry et al. |
| 4,648,542 A | 3/1987 | Fox et al. |
| 4,662,373 A | 5/1987 | Montgomery et al. |
| 4,669,647 A | 6/1987 | Storace |
| 4,671,445 A | 6/1987 | Barker et al. |
| 4,700,703 A | 10/1987 | Resnick et al. |
| 4,850,355 A | 7/1989 | Brooks et al. |
| 4,874,122 A | 10/1989 | Froelich et al. |
| 4,899,745 A | 2/1990 | Laboureau |
| 5,032,127 A | 7/1991 | Frazee et al. |
| 5,156,609 A | 10/1992 | Nakao et al. |
| 5,158,567 A | 10/1992 | Green |
| 5,242,457 A | 9/1993 | Akopov et al. |
| 5,312,023 A | 5/1994 | Green et al. |
| 5,312,024 A | 5/1994 | Grant et al. |
| 5,333,772 A | 8/1994 | Rothfuss et al. |
| 5,350,400 A | 9/1994 | Esposito et al. |
| 5,392,978 A | 2/1995 | Velez et al. |
| 5,413,584 A * | 5/1995 | Schulze ..................... 606/219 |
| 5,439,468 A | 8/1995 | Schulze et al. |
| 5,465,567 A | 11/1995 | Schmolke et al. |
| 5,465,894 A | 11/1995 | Clark et al. |
| 5,484,095 A | 1/1996 | Green et al. |
| 5,544,802 A | 8/1996 | Crainich |
| 5,564,615 A | 10/1996 | Bishop et al. |
| 5,626,585 A | 5/1997 | Mittelstadt et al. |
| 5,630,540 A | 5/1997 | Blewett |
| 5,645,567 A | 7/1997 | Crainich |
| 5,692,668 A | 12/1997 | Schulze et al. |
| 5,715,987 A | 2/1998 | Kelley et al. |
| 5,725,554 A | 3/1998 | Simon et al. |
| 5,732,871 A | 3/1998 | Clark et al. |
| 5,762,255 A | 6/1998 | Chrisman et al. |
| 5,465,895 A | 11/1998 | Knodel et al. |
| 5,829,662 A | 11/1998 | Allen et al. |
| 6,102,922 A | 8/2000 | Jakobsson et al. |
| 6,228,098 B1 | 5/2001 | Kayan et al. |
| 6,269,997 B1 | 8/2001 | Balazs et al. |
| 6,277,131 B1 | 8/2001 | Kalikow |
| 6,306,149 B1 | 10/2001 | Meade |
| 6,330,964 B1 | 12/2001 | Kayan et al. |
| 6,352,541 B1 | 3/2002 | Kienzle et al. |
| 6,447,524 B1 | 9/2002 | Knodel et al. |
| 6,450,391 B1 | 9/2002 | Kayan et al. |
| 6,453,780 B2 | 9/2002 | Habermehl |
| 6,530,933 B1 * | 3/2003 | Yeung et al. ................. 606/151 |
| 6,551,333 B2 | 4/2003 | Kuhns et al. |
| 6,572,626 B1 | 6/2003 | Knodel et al. |
| 6,695,854 B1 | 2/2004 | Kayan et al. |
| 6,726,705 B2 | 4/2004 | Peterson et al. |
| 6,767,356 B2 | 7/2004 | Kanner et al. |
| 6,837,895 B2 | 1/2005 | Mayenberger |
| 6,915,937 B2 | 7/2005 | Lat et al. |
| 6,957,756 B2 | 10/2005 | Lat et al. |
| 7,056,330 B2 | 6/2006 | Gayton |
| 7,059,331 B2 | 6/2006 | Adams et al. |
| 7,059,509 B2 | 6/2006 | Brown |
| 7,112,214 B2 | 9/2006 | Peterson et al. |
| 7,153,314 B2 | 12/2006 | Laufer et al. |
| 7,175,638 B2 | 2/2007 | Gannoe et al. |
| 7,179,265 B2 | 2/2007 | Manetakis |
| 7,300,454 B2 | 11/2007 | Park et al. |
| 7,320,692 B1 | 1/2008 | Bender et al. |
| 7,344,544 B2 | 3/2008 | Bender et al. |
| 7,364,060 B2 | 4/2008 | Milliman |
| 7,407,076 B2 | 8/2008 | Racenet et al. |
| 7,458,978 B1 | 12/2008 | Bender et al. |
| 7,473,258 B2 | 1/2009 | Clauson et al. |
| 7,506,791 B2 | 3/2009 | Omaits et al. |
| 7,513,408 B2 | 4/2009 | Shelton, IV et al. |
| 7,533,790 B1 | 5/2009 | Knodel et al. |
| 7,556,647 B2 | 7/2009 | Drews et al. |
| 7,741,520 B2 | 6/2010 | Brueggemeier et al. |
| 7,744,613 B2 | 6/2010 | Ewers et al. |
| 7,753,870 B2 * | 7/2010 | Demarais et al. ................. 604/8 |
| 7,794,475 B2 | 9/2010 | Hess et al. |
| 7,832,408 B2 | 11/2010 | Shelton, IV et al. |
| 7,887,553 B2 | 2/2011 | Lehman et al. |
| 7,914,543 B2 | 3/2011 | Roth et al. |
| 7,954,684 B2 | 6/2011 | Boudreaux |
| 8,006,167 B2 | 8/2011 | Lapstun et al. |
| 8,066,720 B2 | 11/2011 | Knodel et al. |
| 8,142,450 B2 | 3/2012 | Harris et al. |
| 8,216,236 B2 | 7/2012 | Heinrich et al. |
| 8,342,376 B2 | 1/2013 | Surti |
| 8,439,244 B2 | 5/2013 | Holcomb et al. |
| 8,469,252 B2 | 6/2013 | Holcomb et al. |
| 8,602,286 B2 | 12/2013 | Crainich et al. |
| 8,728,119 B2 | 5/2014 | Cummins |
| 8,801,732 B2 | 8/2014 | Harris et al. |
| 8,858,579 B2 | 10/2014 | Suyker et al. |
| 2004/0097971 A1 | 5/2004 | Hughett |
| 2004/0210243 A1 | 10/2004 | Gannoe et al. |
| 2004/0215216 A1 | 10/2004 | Gannoe et al. |
| 2004/0225305 A1 | 11/2004 | Ewers et al. |
| 2005/0080454 A1 | 4/2005 | Drews et al. |
| 2005/0085830 A1 | 4/2005 | Lehman et al. |
| 2005/0116009 A1 | 6/2005 | Milliman |
| 2005/0256533 A1 | 11/2005 | Roth et al. |
| 2006/0020276 A1 | 1/2006 | Saadat et al. |
| 2006/0060630 A1 | 3/2006 | Shelton, IV |
| 2006/0217749 A1 | 9/2006 | Wilson, Jr. et al. |
| 2007/0185504 A1 | 8/2007 | Manetakis et al. |
| 2008/0045598 A1 | 2/2008 | Brueggemeier et al. |
| 2008/0078805 A1 | 4/2008 | Pmaits et al. |
| 2008/0082124 A1 | 4/2008 | Hess et al. |
| 2008/0217376 A1 | 9/2008 | Clauson et al. |
| 2008/0249566 A1 | 10/2008 | Harris et al. |
| 2008/0314957 A1 | 12/2008 | Boudreaux |
| 2008/0319455 A1 | 12/2008 | Harris et al. |
| 2009/0072006 A1 | 3/2009 | Clauson et al. |
| 2009/0112233 A1 | 4/2009 | Xiao |
| 2009/0112304 A1 | 4/2009 | Weadock et al. |
| 2009/0134198 A1 | 5/2009 | Knodel et al. |
| 2009/0134199 A1 | 5/2009 | Heinrich et al. |
| 2009/0206127 A1 | 8/2009 | Danielson et al. |
| 2009/0318936 A1 * | 12/2009 | Harris et al. ................. 606/139 |
| 2010/0187283 A1 | 7/2010 | Crainich et al. |

(56) References Cited

U.S. PATENT DOCUMENTS

| | | | |
|---|---|---|---|
| 2010/0187284 A1 | 7/2010 | Crainich et al. | |
| 2010/0191255 A1 | 7/2010 | Crainich et al. | |
| 2010/0191282 A1 | 7/2010 | Harris et al. | |
| 2010/0237132 A1 | 9/2010 | Measamer et al. | |

FOREIGN PATENT DOCUMENTS

| | | |
|---|---|---|
| DE | 29720952 U1 | 1/1998 |
| EP | 0068046 A2 | 1/1983 |
| EP | 0864297 A2 | 9/1998 |
| EP | 1908423 A2 | 4/2008 |
| JP | 2009-502 | 1/1990 |
| JP | 2004-508091 | 3/2004 |
| JP | 2004-520154 | 7/2004 |
| JP | 2005-530567 | 10/2005 |
| JP | 2006-307874 | 11/2006 |
| JP | 2008-279260 | 11/2008 |
| JP | 2008-543371 | 12/2008 |
| JP | 2009-236245 | 10/2009 |
| WO | WO 01/76489 A1 | 10/2001 |
| WO | WO 02/98302 | 12/2002 |
| WO | WO 2008/109876 A1 | 9/2008 |
| WO | WO 2008/112942 | 9/2008 |
| WO | WO 2008/118928 A2 | 10/2008 |
| WO | WO 2009/137517 A1 | 11/2009 |
| WO | WO 2012/103286 A1 | 8/2012 |
| WO | WO 2012/103291 A1 | 8/2012 |

OTHER PUBLICATIONS

International Search Report dated Apr. 10, 2012 (PCT/US2012/022651).
International Search Report dated Apr. 10, 2012 (PCT/US2012/022656).
International Search Report dated Aug. 13, 2010 (PCT/US2010/021953).
International Search Report dated Apr. 5, 2011 (PCT/US2011/020476).
European Search Report, dated Oct. 1, 2012, Application No. 12172811.7.
European Search Report, dated Oct. 1, 2012, Application No. 12172808.3.
European Search Report, dated Oct. 1, 2012, Application No. 12172816.6.
Co-pending U.S. Appl. No. 12/359,351, filed Jan. 26, 2009, first named inventor Jason L. Harris.
Co-pending U.S. Appl. No. 12/359,354, filed Jan. 26, 2009, first named inventor Jason L. Harris.
Co-pending U.S. Appl. No. 12/359,357, filed Jan. 26, 2009, first named inventor Jason L. Harris.
Co-pending U.S. Appl. No. 12/609,336, filed Oct. 30, 2009, first named inventor Lawrence Crainich.
Co-pending U.S. Appl. No. 12/690,285, filed Jan. 20, 2010, first named inventor Lawrence Crainich.
Co-pending U.S. Appl. No. 13/015,966, filed Jan. 28, 2011, first named inventor Matthew D. Holcomb.
Co-pending U.S. Appl. No. 13/015,977, filed Jan. 28, 2011, first named inventor Matthew D. Holcomb.
Co-pending U.S. Appl. No. 13/164,949, filed Jun. 21, 2011, first named inventor Matthew D. Holcomb.
Co-pending U.S. Appl. No. 13/164,954, filed Jun. 21, 2011, first named inventor Matthew D. Holcomb.
Co-pending U.S. Appl. No. 13/164,960, filed Jun. 21, 2011, first named inventor Matthew D. Holcomb.
Co-pending U.S. Appl. No. 13/164,963, filed Jun. 21, 2011, first named inventor Jason L. Harris.
Co-pending U.S. Appl. No. 13/362,172, filed Jan. 31, 2012, first named inventor Jason L. Harris.
Co-pending U.S. Appl. No. 13/371,678, filed Feb. 13, 2012, first named inventor Matthew D. Holcomb.
Co-pending U.S. Appl. No. 13/371,684, filed Feb. 13, 2012, first named inventor Matthew D. Holcomb.
Talebpour M, Amoli BS. Laparoscopic total gastric vertical plication in morbid obesity. J Laparoendosc Adv Surg Tech A 2007;17:793-8.
Sales Puccini, CE. Surset gástrico de Sales: una alternative para cirugia Bariátrica restrictive. Rev Colomb Cir 2008;23(3):131-5.
Fusco PEB, Poggetti RS, Younes RN, Fontes B, Birolini D. Evaluation of gastric greater curvature invagination for weight loss in rats. Obes Surg 2006;16:171-7.
Fusco PEB, Poggetti RS, Younes RN, Fontes B, Birolini D. Comparison of anterior gastric wall and greater gastric curvature invaginations for weight loss in rats. Obes Surg 2007;17:1340-5.
Brethauer SA, Harris JL, Chand B, Kroh M, Rogula T, Schauer PR. Initial results of vertical gastric plication for severe obesity. Society of American Gastrointestinal and Endoscoplc Surgeons. Phoenix, Arizona. Apr. 22-25, 2009.
Ramos AC, Galvao M, Behrens E, Montufar F, Zundel N. Tubular sleeve gastroplasty (TSG) as a new approach to bariatric treatment. 14th World Congress of the International Federation for the Surgery of Obesity—Paris, France—Aug. 26-29, 2009.
Crainich, L. 'Forming a 90 deg Bend' Metal Forming Magazine (1991) vol. 25, No. 8 pp. 59-60.
Crainich, L. 'Fractures in Metal Stampings' Metal Forming Magazine (1996) pp. 84-85.
Brethauer, et al 'Laparoscopic gastric plication for the treatment of severe obesity' Surg Obest Relat Dis 2011; 7:15-22.
Fusco PEB, Poggetti RS, Younes RN, Fontes B, Birolini D. Evaluation of Gastric Greater Curvature Invagination for Weight Loss in Rats. Obes Surg 2006; 16:172.
Huang et al 'Novel bariatric technology: laparoscopic adjustable gastric banded plication: technique and preliminary results' Surg Obes Relat Dis epub Mar. 2011.
Menchaca et al 'Gastric plication: preclinical study of durability of serosa-to-serosa apposition' Surg Obes Relat Dis 2011; 7: 8-14.
International Preliminary Report dated Jul. 24, 2012, International Application No. PCT/US2011/020472.
International Preliminary Report dated Jul. 24, 2012, International Application No. PCT/US2011/020476.
International Preliminary Report dated Jul. 26, 2011, International Application No. PCT/US2010/021929.
International Preliminary Report dated Jul. 26, 2011, International Application No. PCT/US2010/021953.
International Preliminary Reoprt dated Jul. 30, 2013, International Application No. PCT/US2012/022656.
International Preliminary Report dated Jul. 30, 2013, International Application No. PCT/US2012/022651.
Co-pending U.S. Appl. No. 11/779,314, filed Jul. 18, 2007, first named inventor Mark S. Zeiner.
Co-pending U.S. Appl. No. 11/779,322, filed Jul. 18, 2007, first named inventor Mark S. Zeiner.
Co-pending U.S. Appl. No. 12/113,829, filed May 1, 2008, first named inventor Mark S. Zeiner.
Co-pending U.S. Appl. No. 12/179,600, filed Jul. 25, 2008, first named inventor Mark S. Zeiner.
Co-pending U.S. Appl. No. 12/608,860, filed Oct. 29, 2009, first named inventor Jason L. Harris.
Co-pending U.S. Appl. No. 12/690,311, filed Jan. 20, 2010, first named inventor Lawrence Crainich.
International Preliminary Report dated Jul. 26, 2011, International Application No. PCT/US2010/021955.
International Preliminary Report dated May 1, 2012, International Application No. PCT/US2010/053736.
International Search Report dated Jun. 1, 2010 (PCT/US2010/021929).
International Search Report dated Jun. 4, 2010 (PCT/US2010/021955).
International Search Report dated Jan. 25, 2011 (PCT/US2010/053736).
Co-pending U.S. Appl. No. 13/911,337, filed Jun. 6, 2013, U.S. Publication No. US-2014-0151435-A1.

* cited by examiner

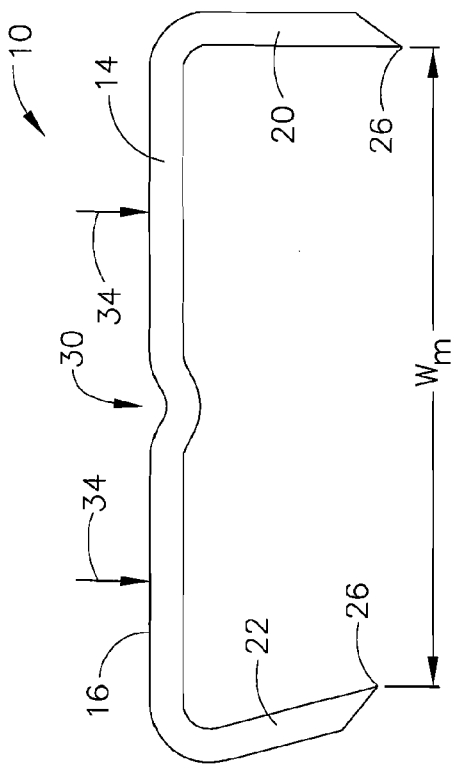
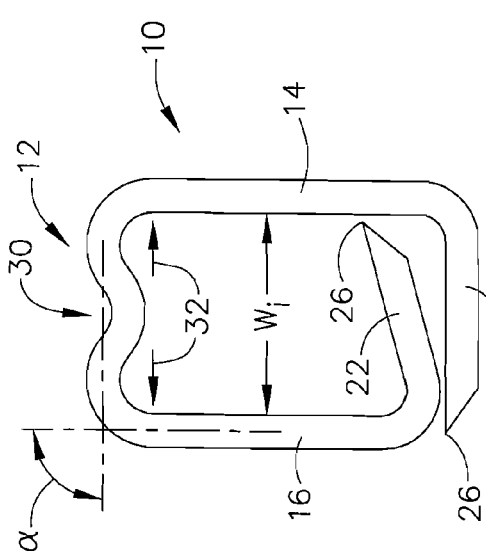
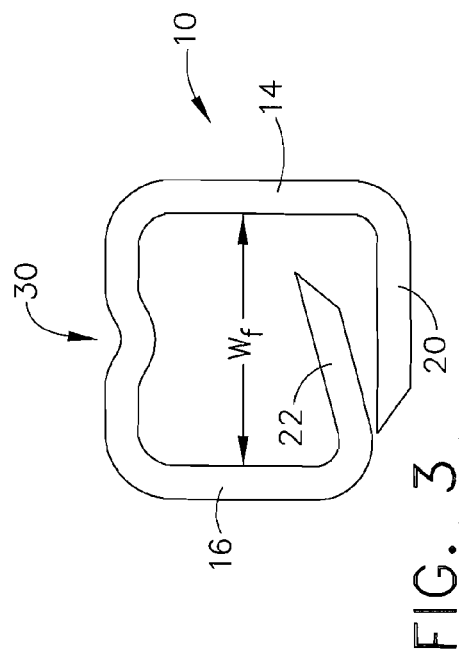
FIG. 1
FIG. 2
FIG. 3

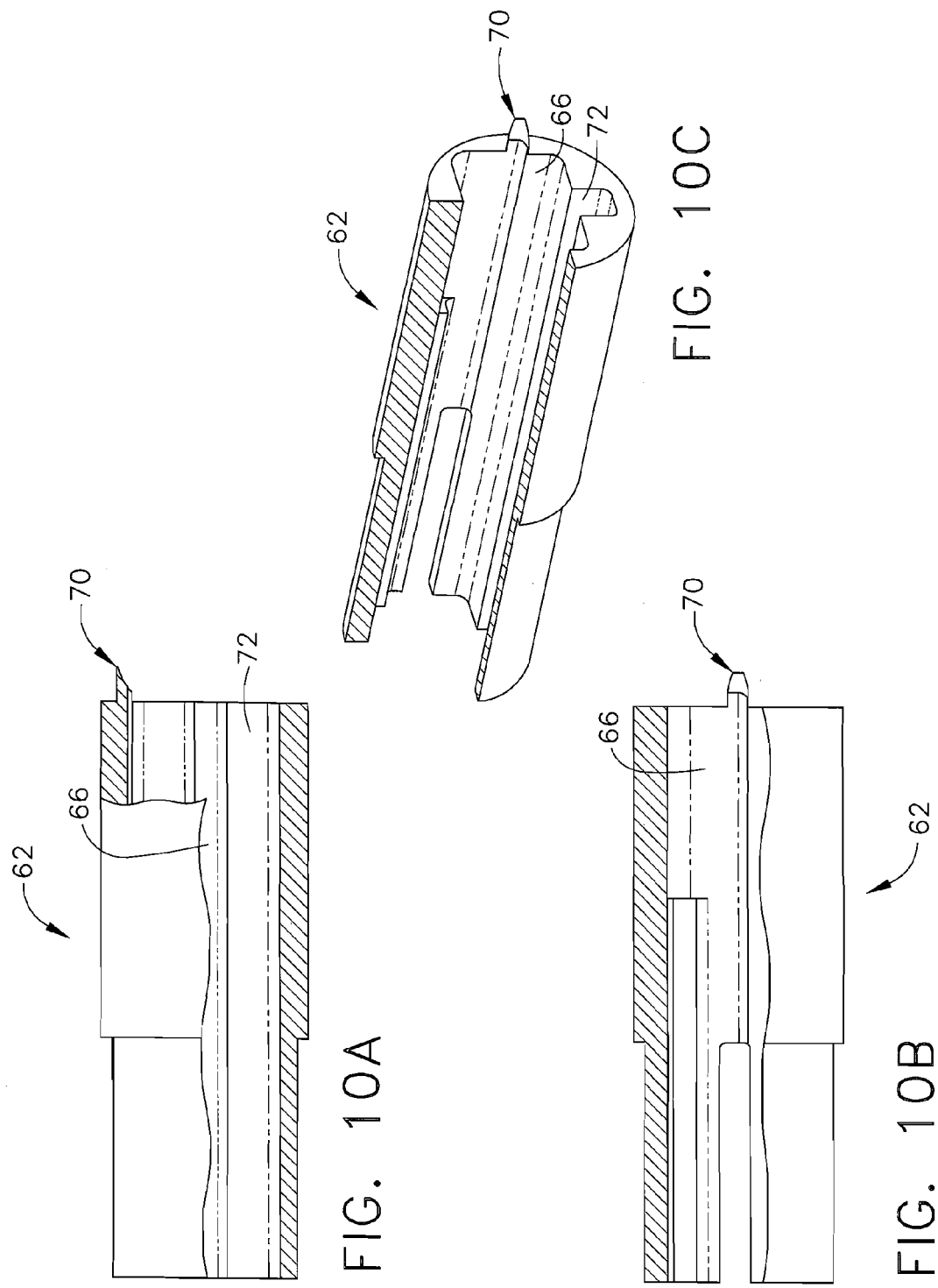

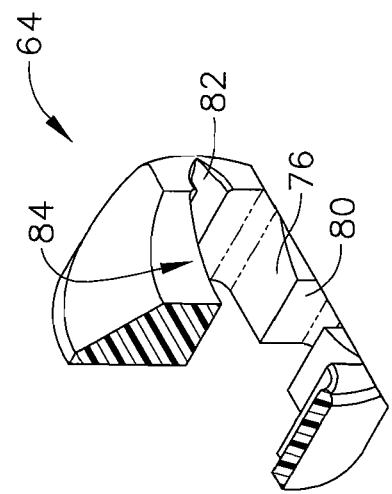
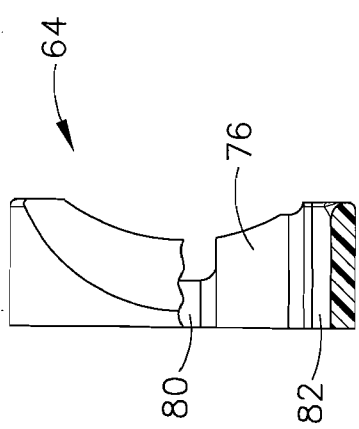
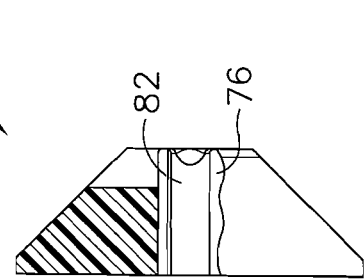

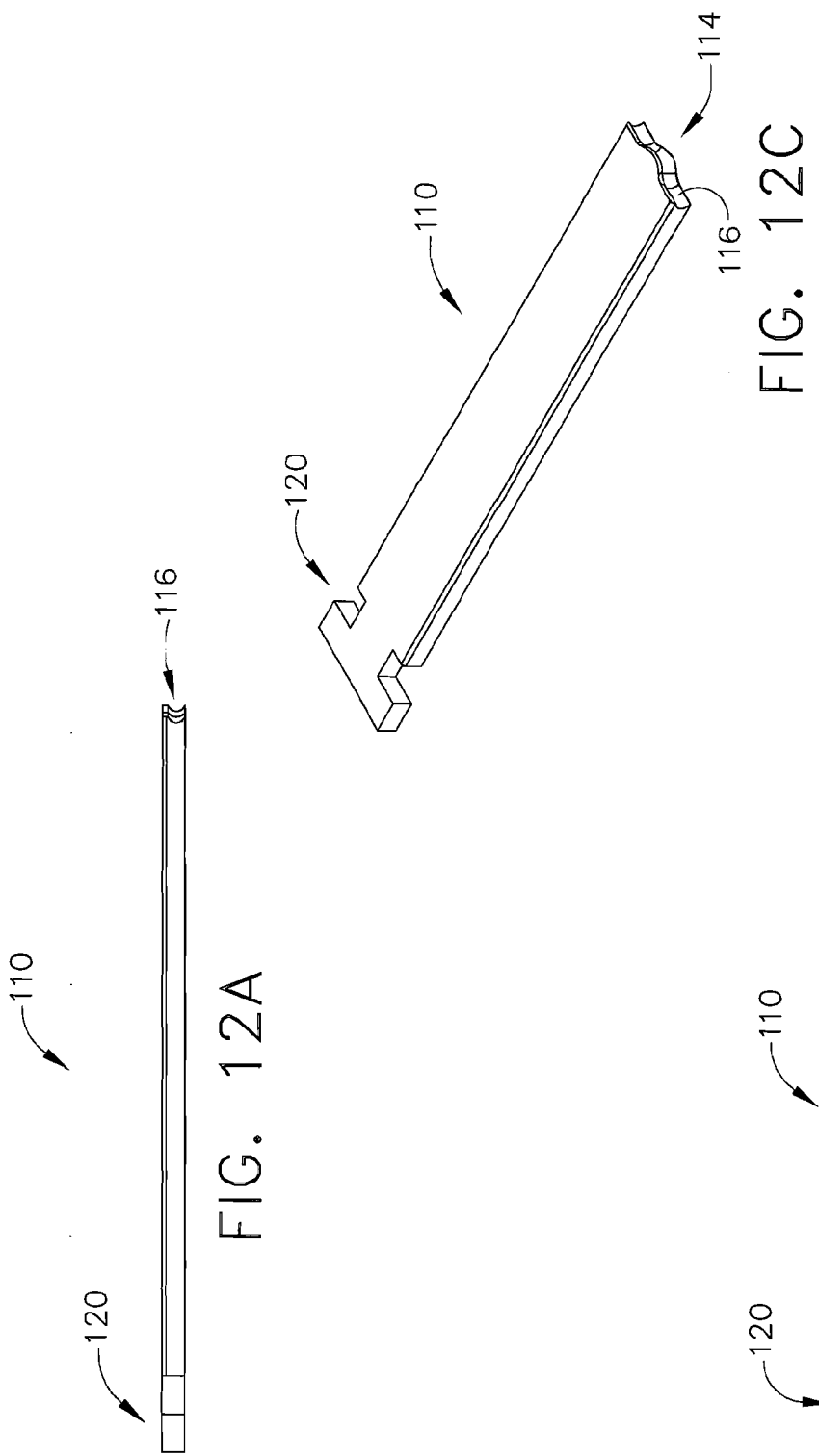

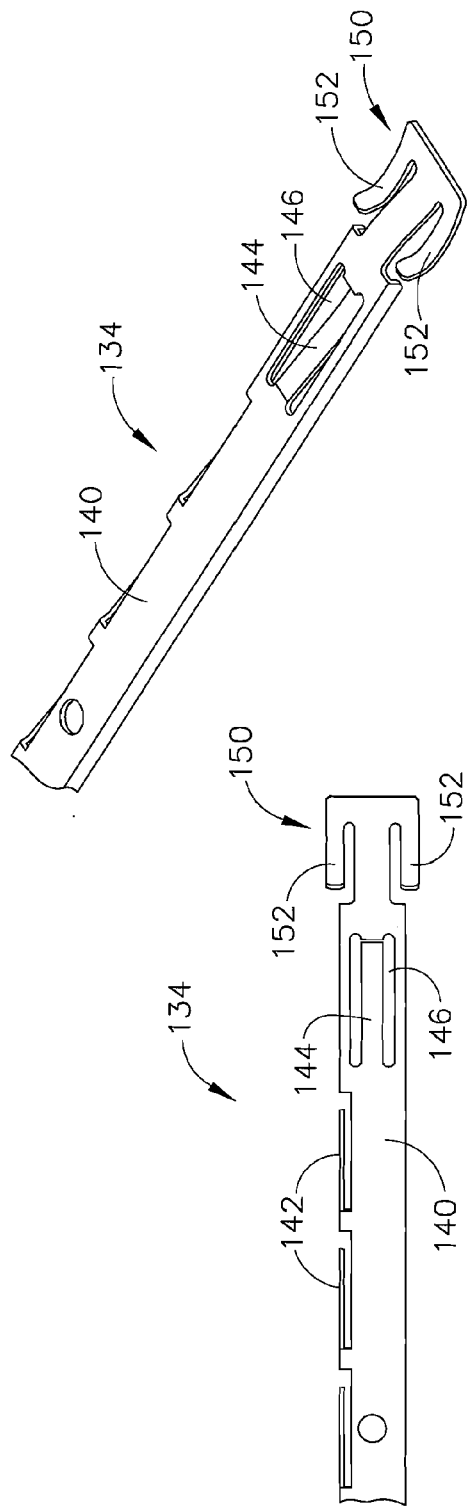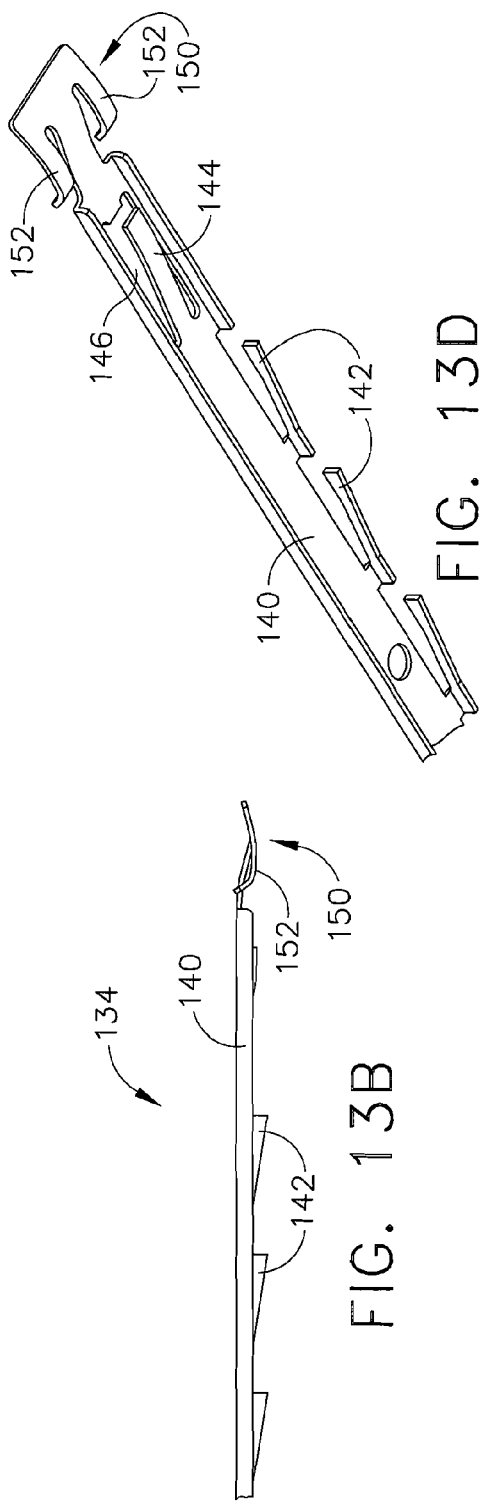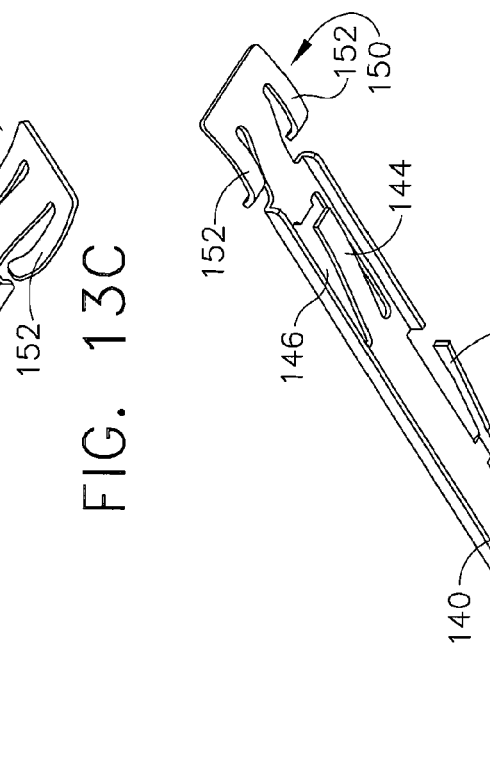

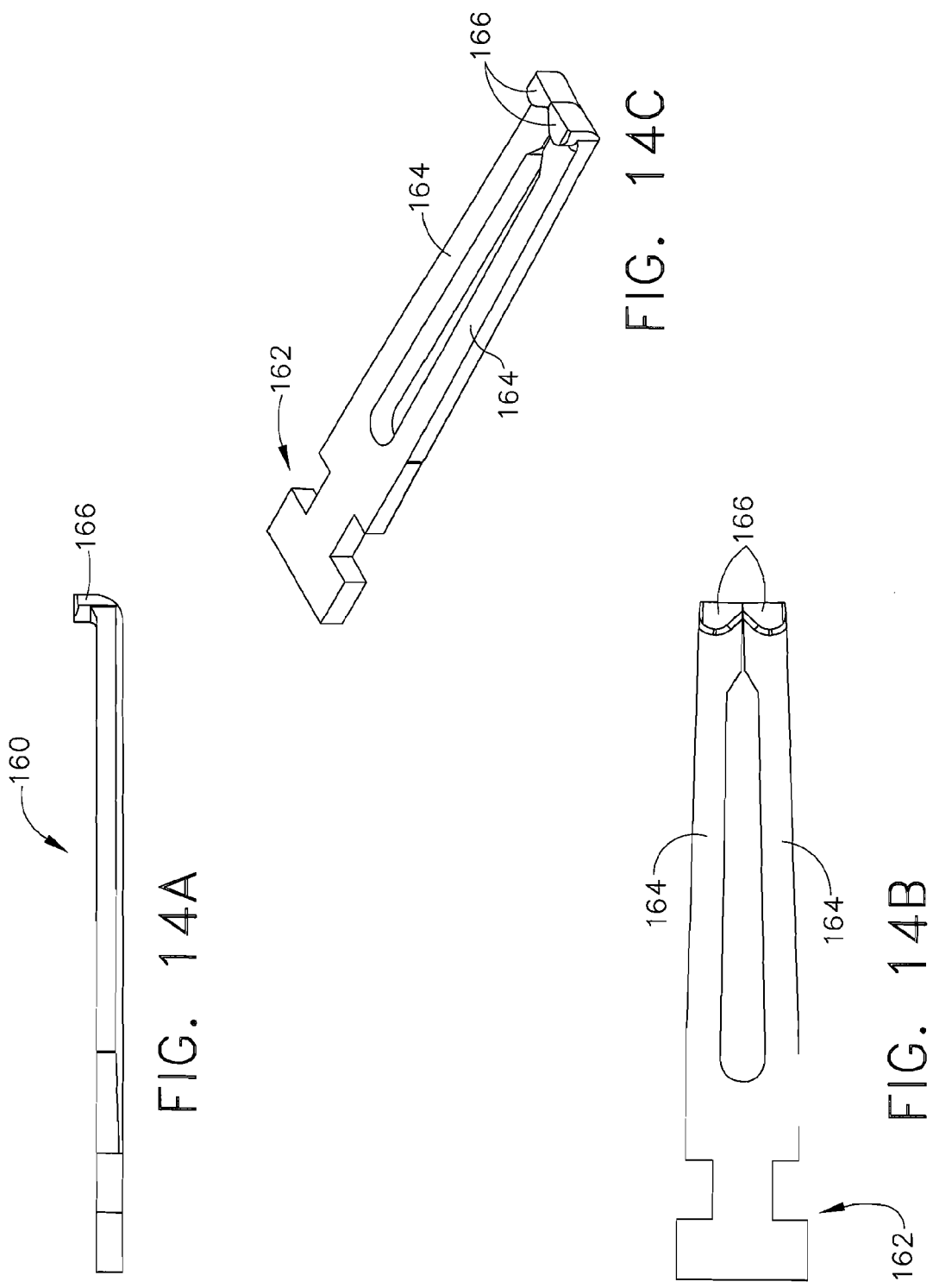

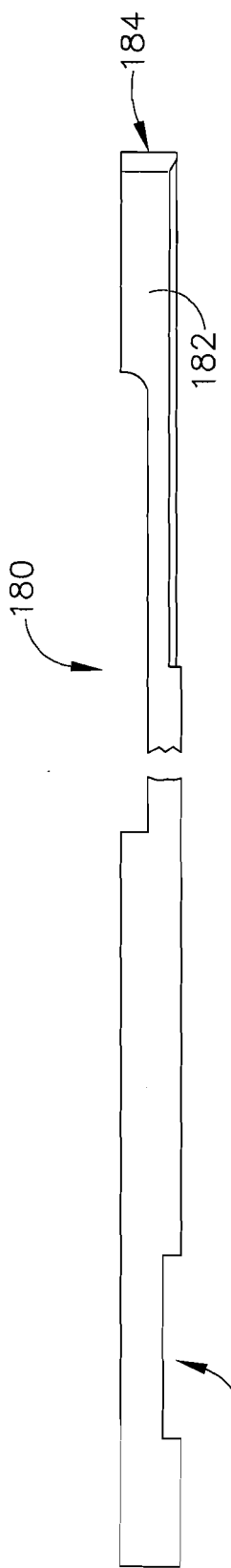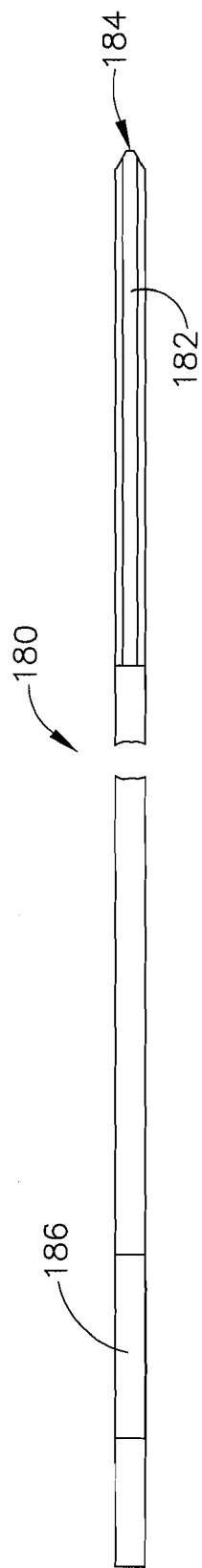

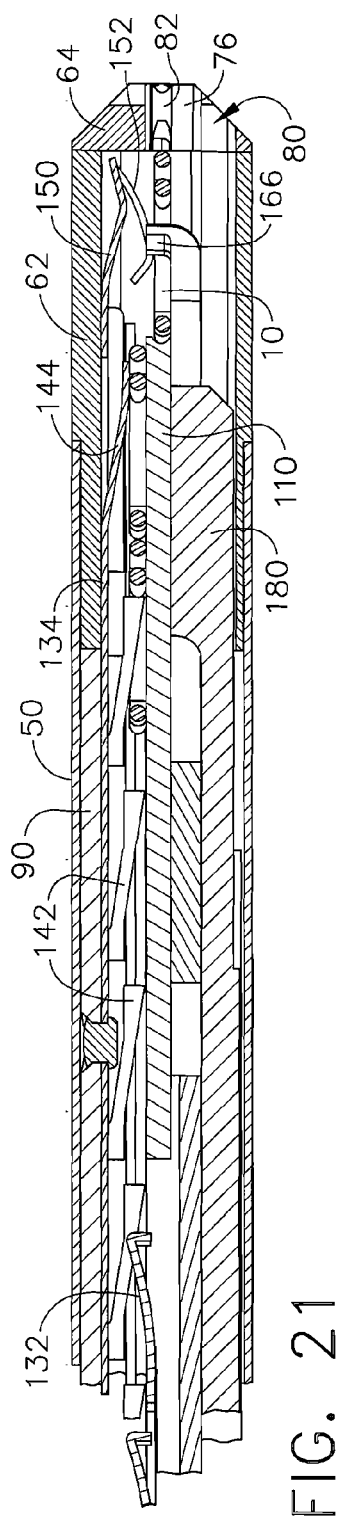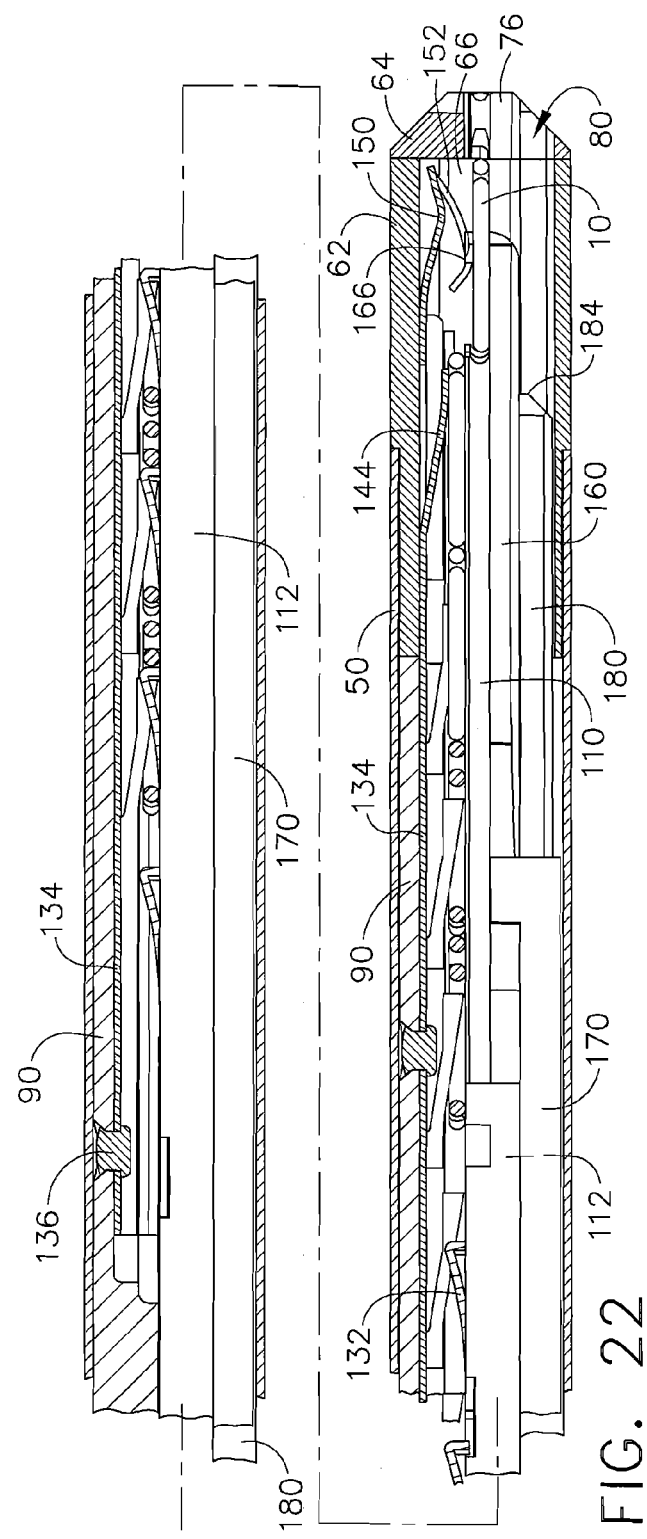

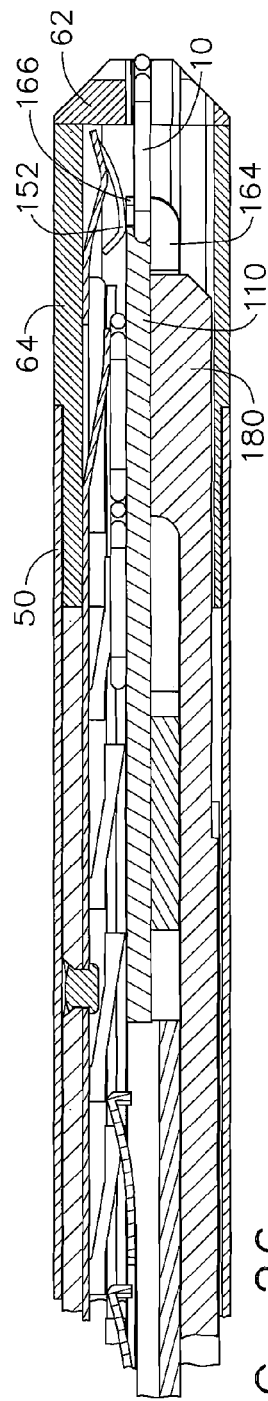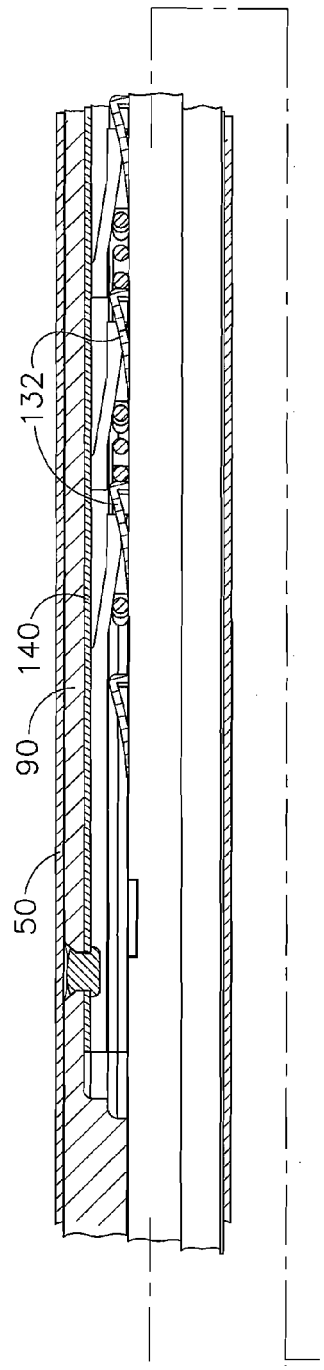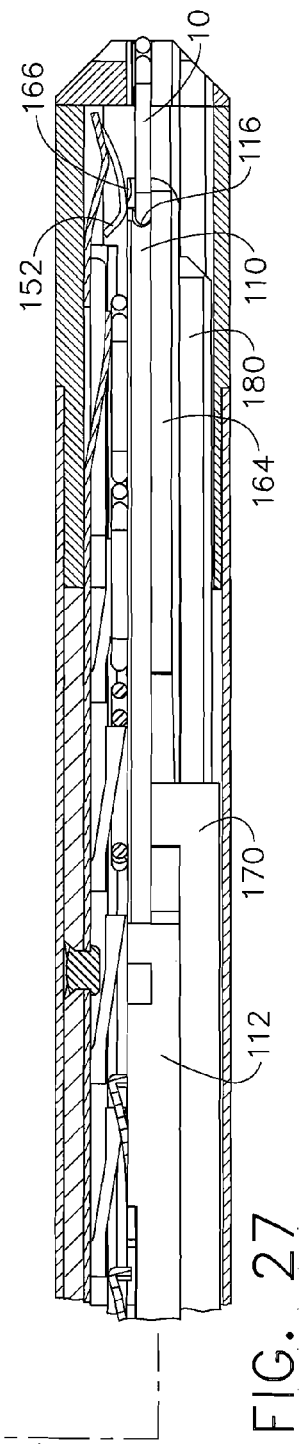
FIG. 26
FIG. 27

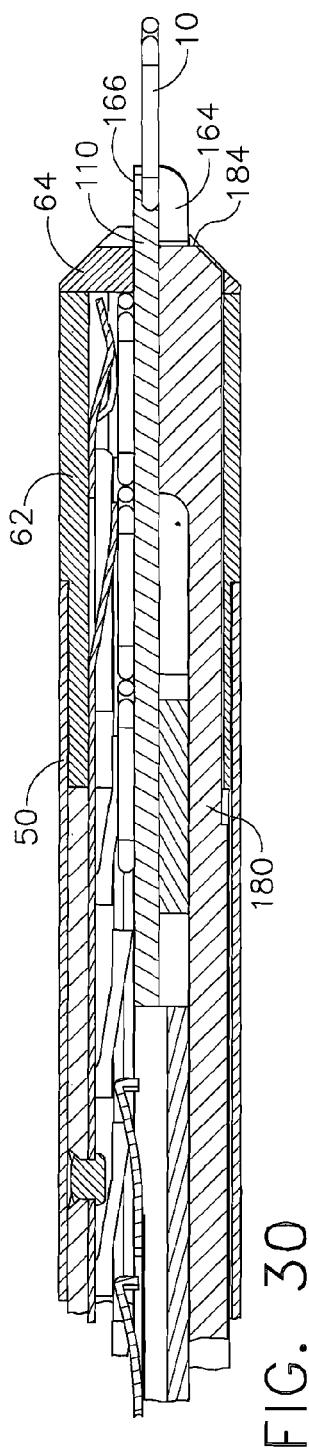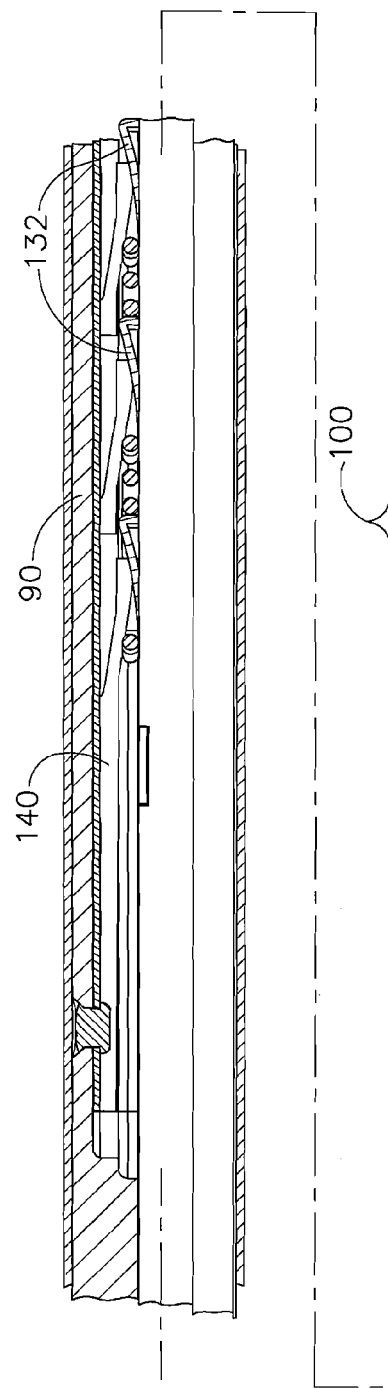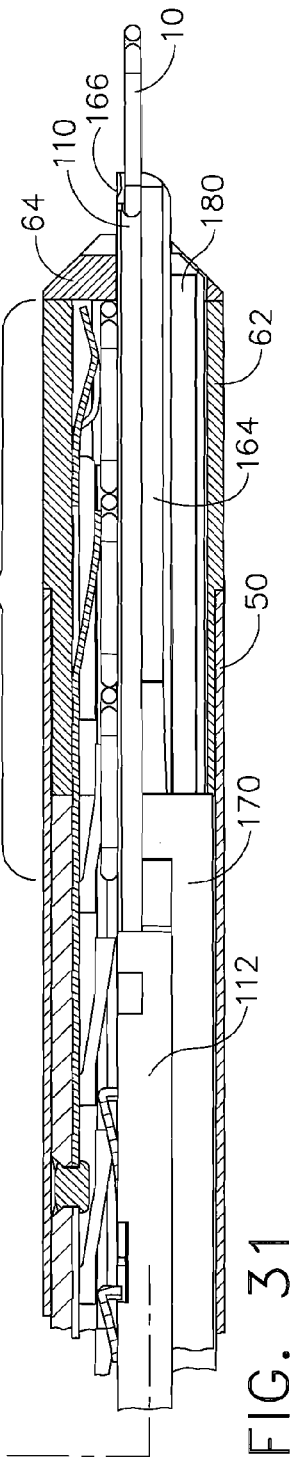

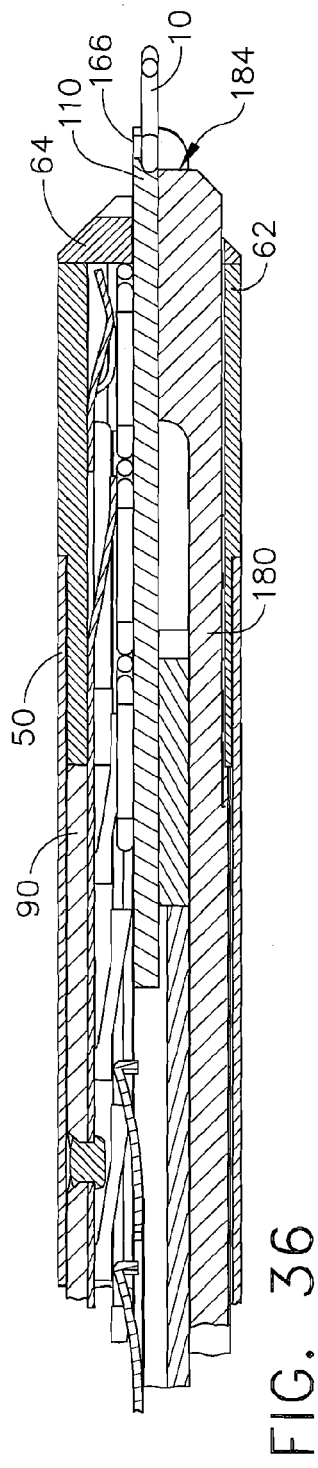
FIG. 36
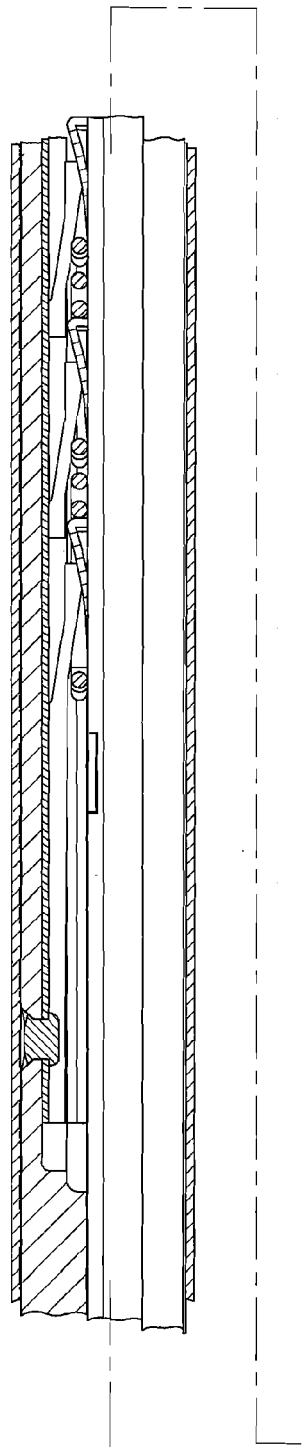
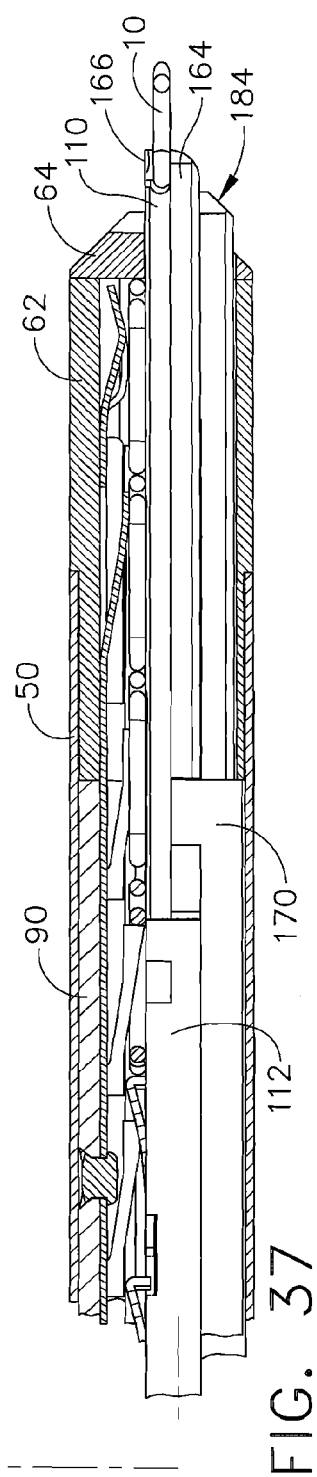
FIG. 37

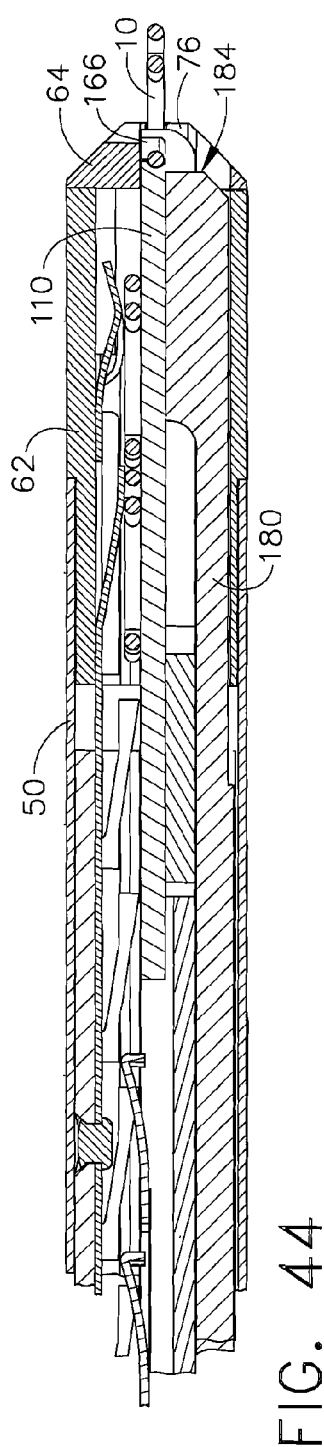
FIG. 44
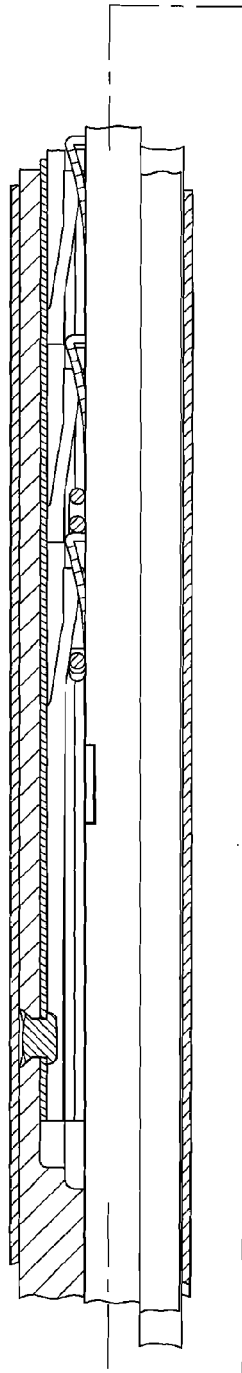
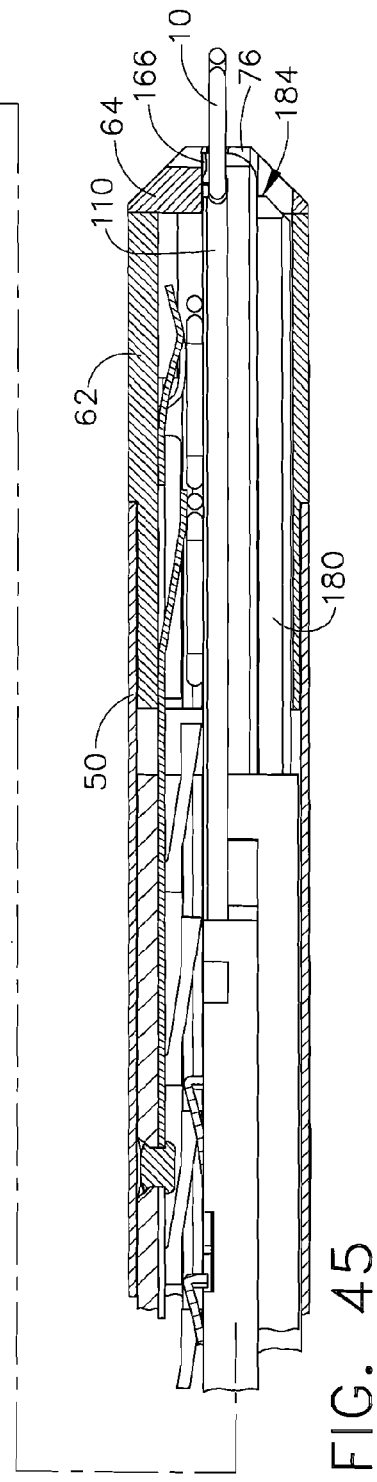
FIG. 45

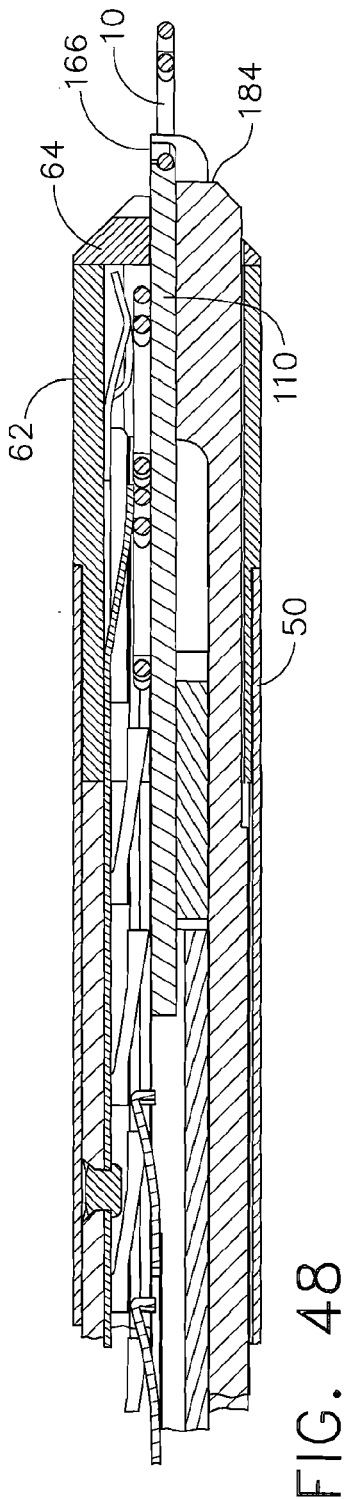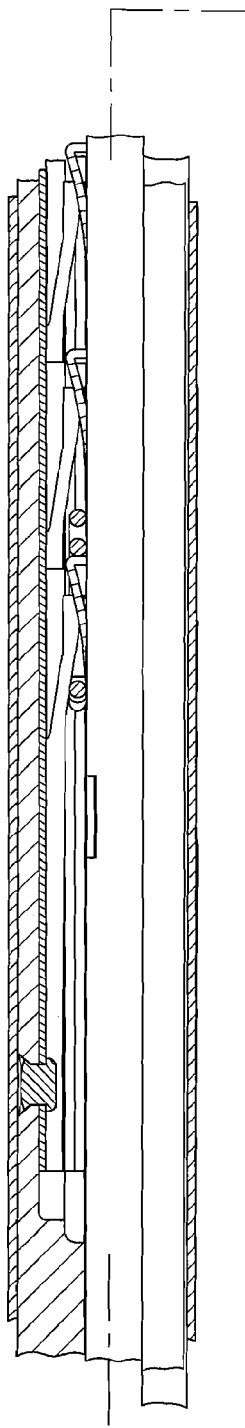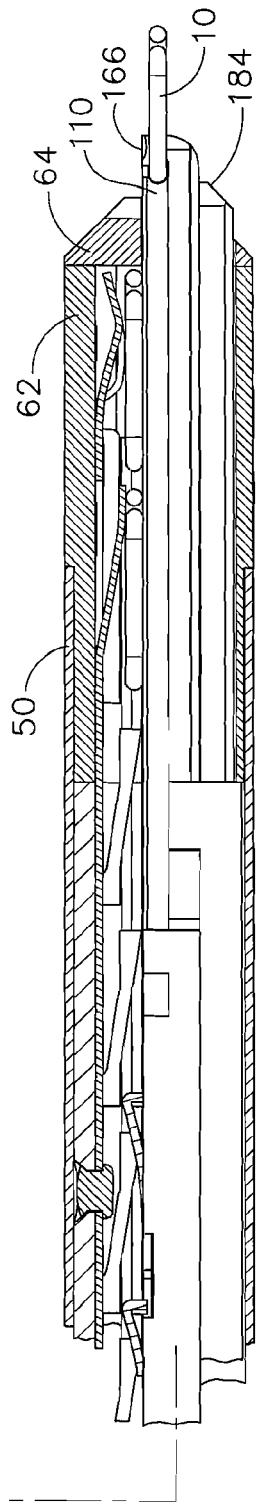
FIG. 48
FIG. 49

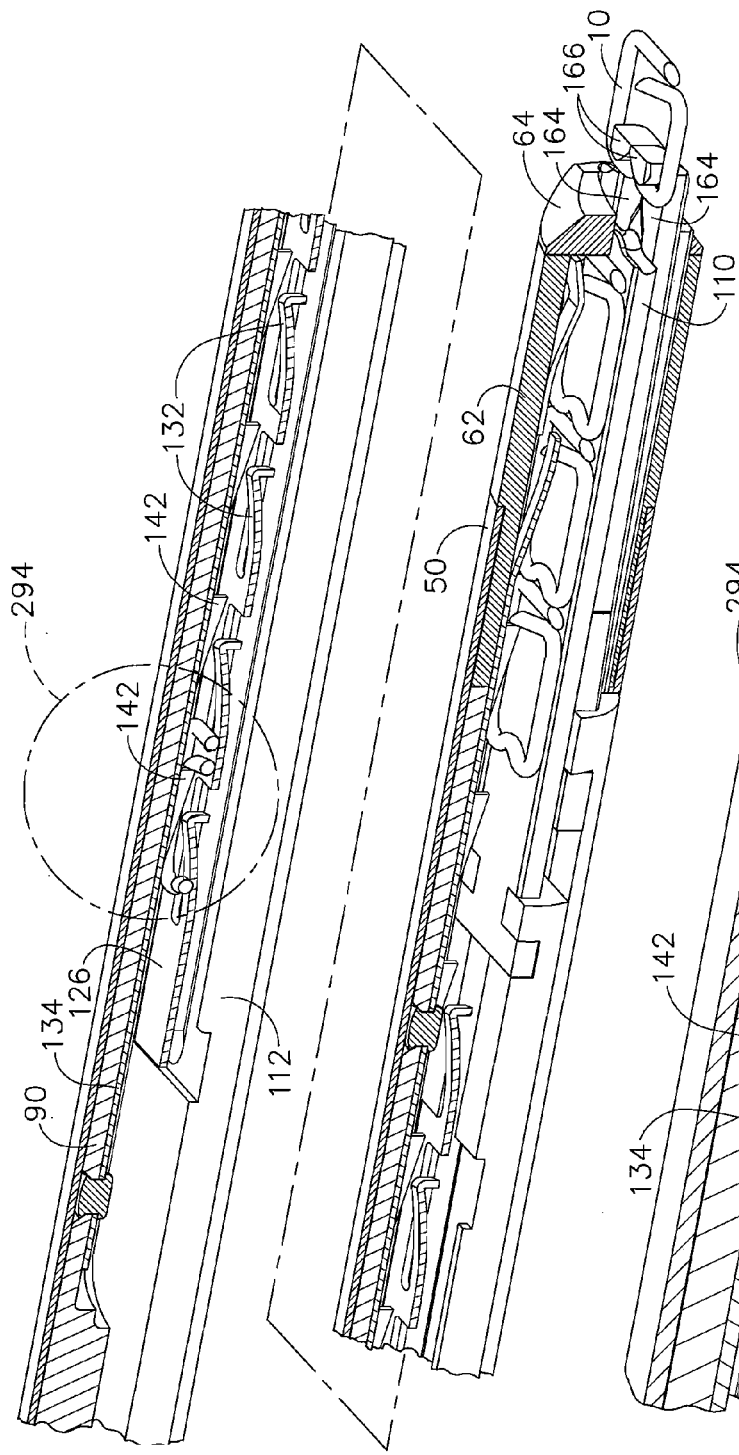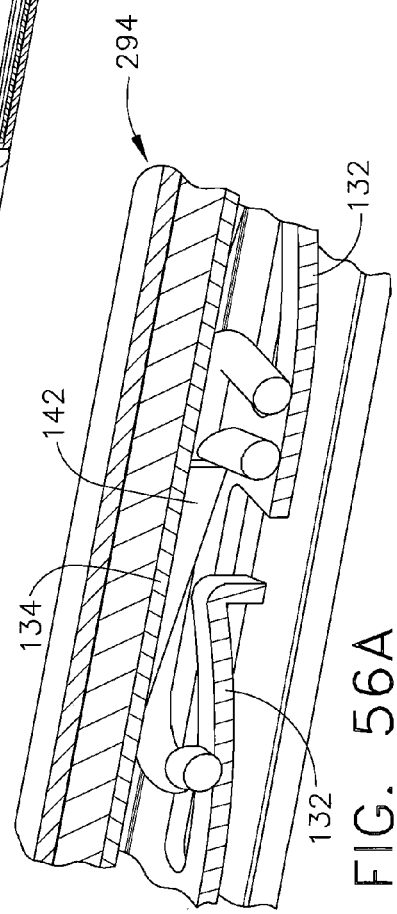

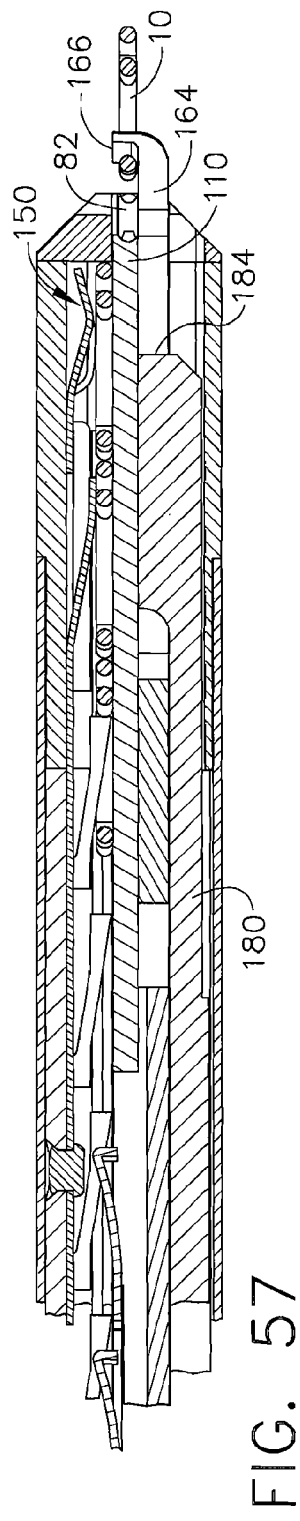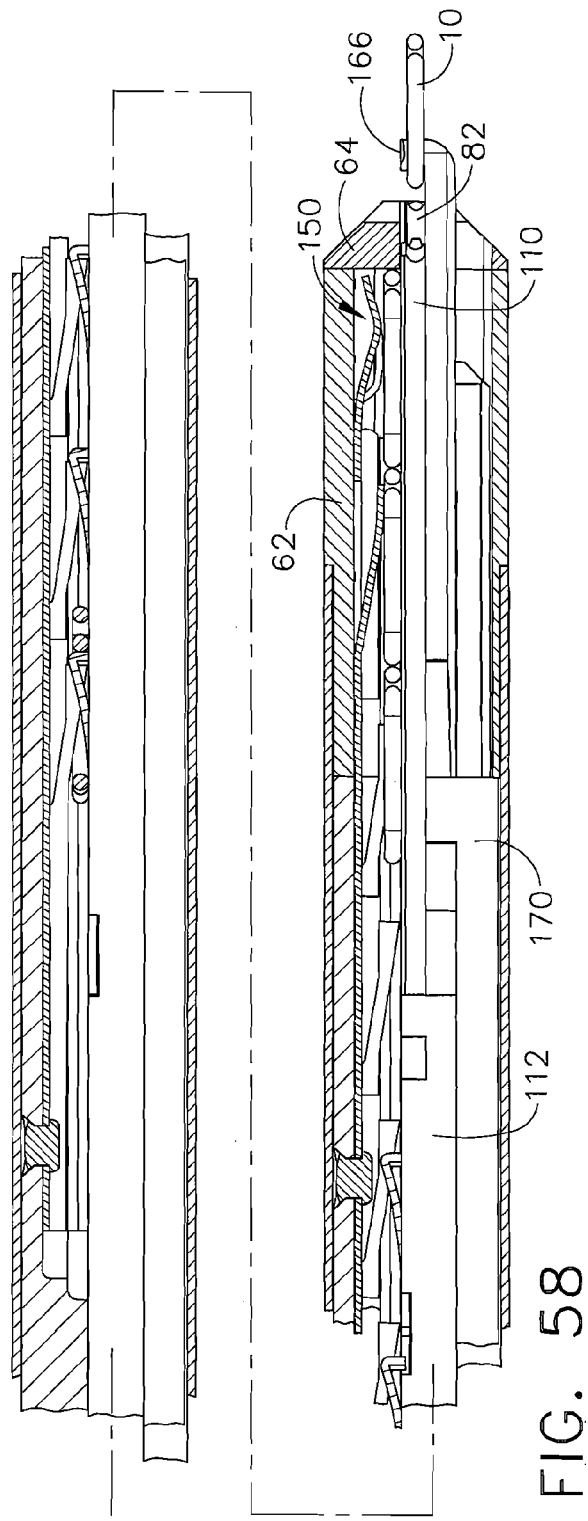

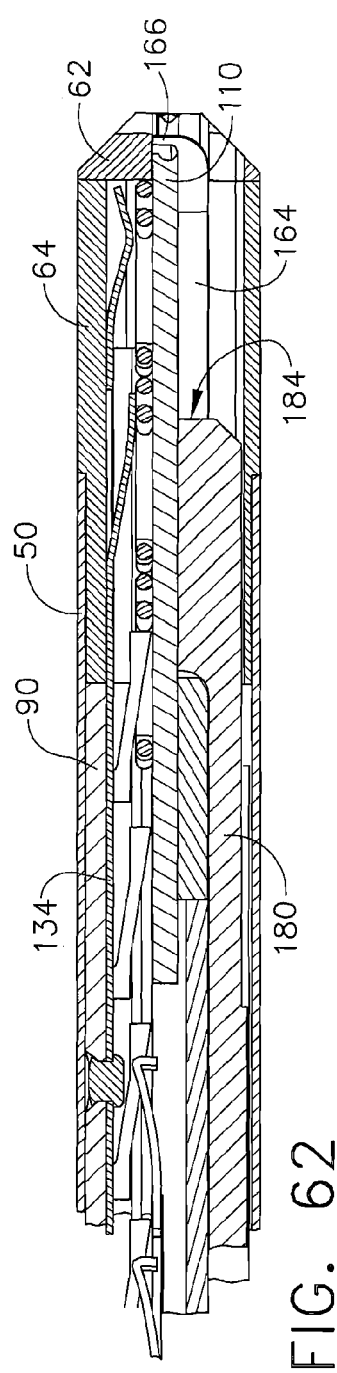
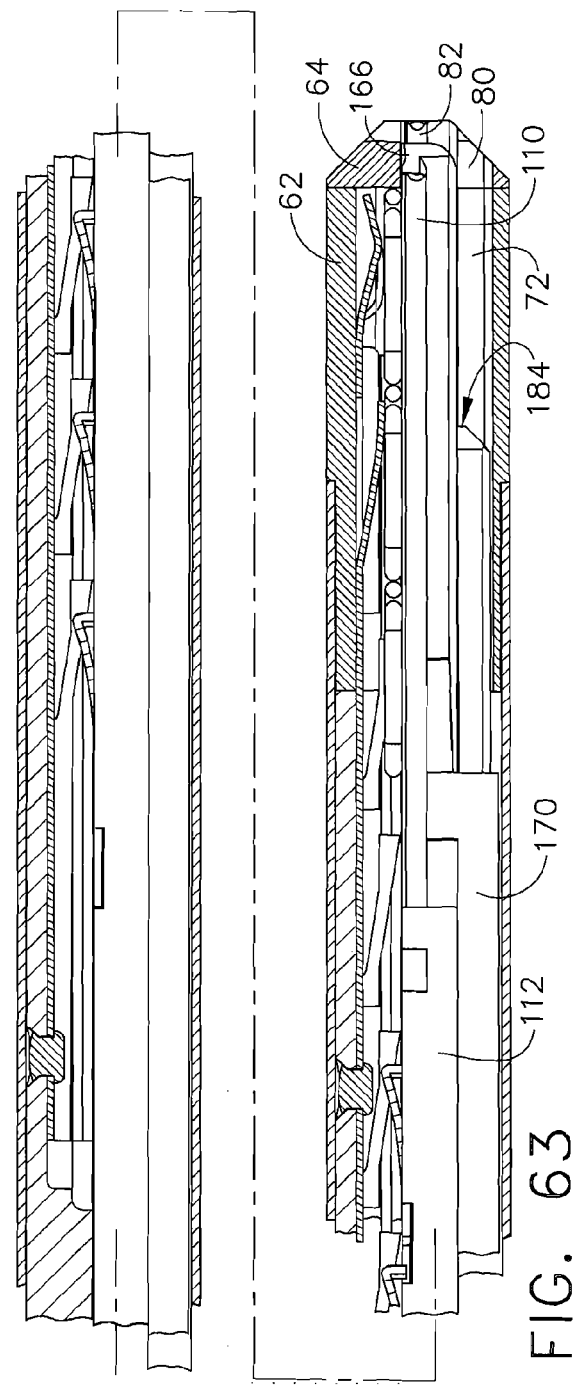
FIG. 62
FIG. 63

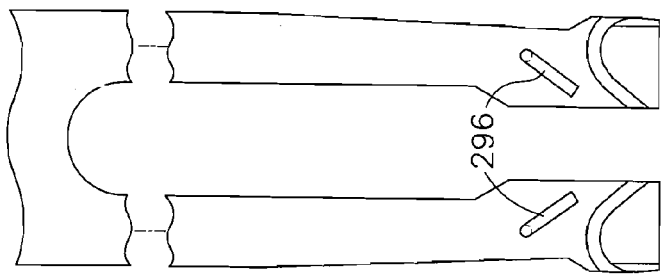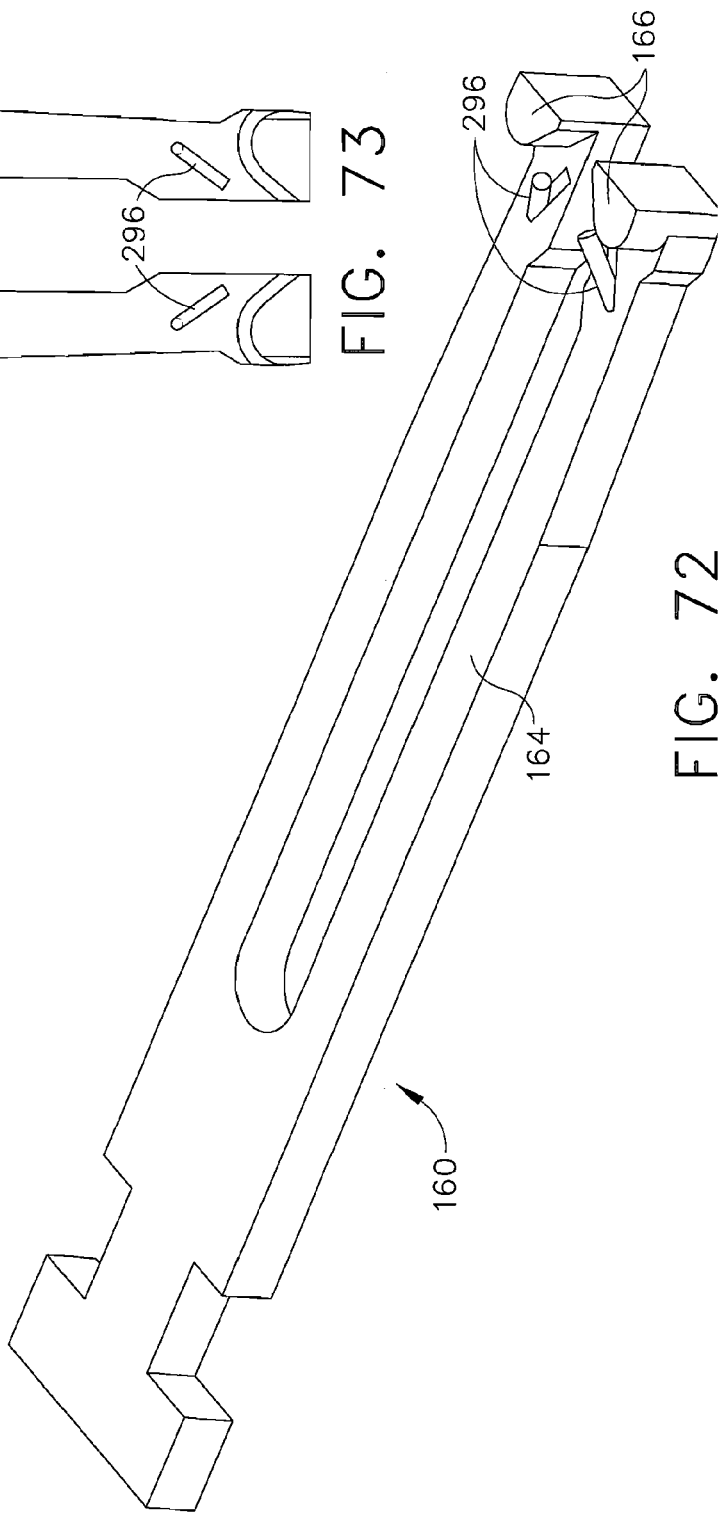

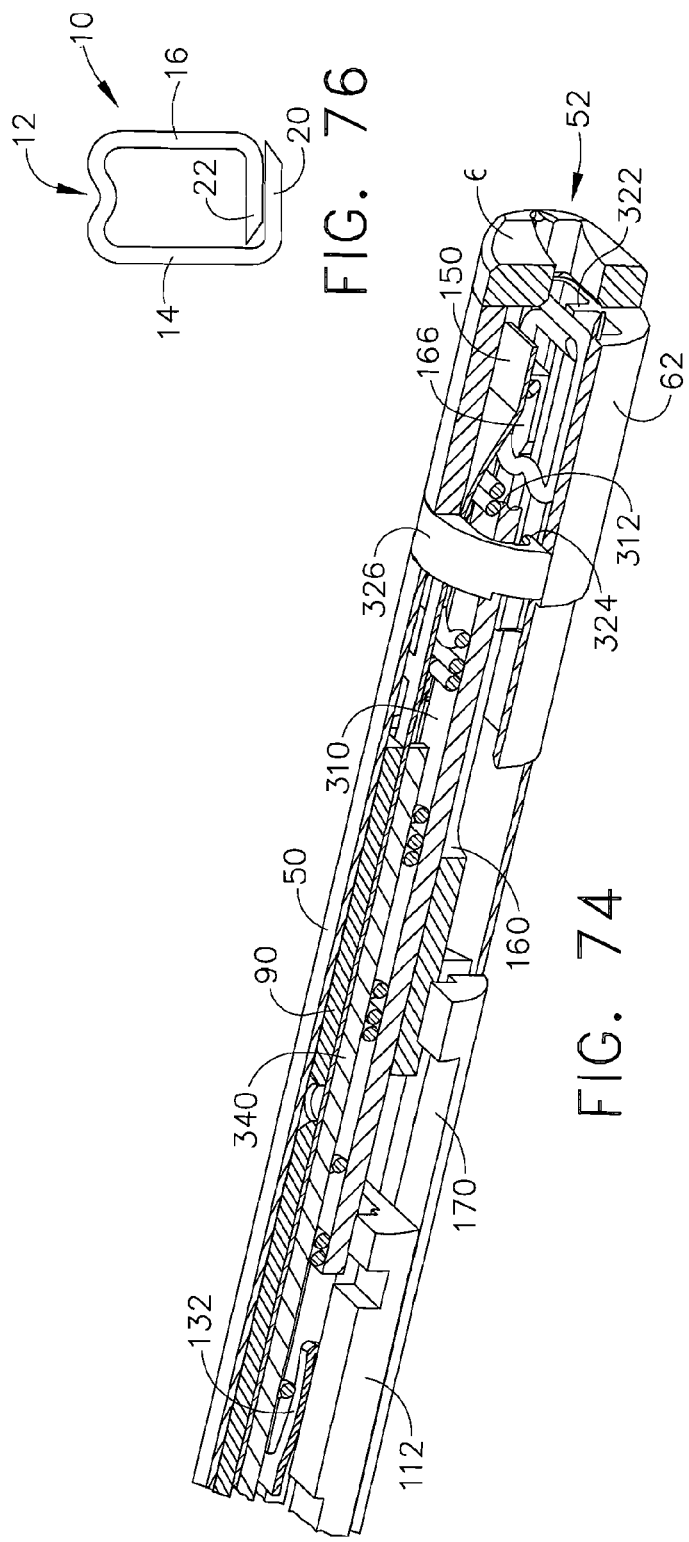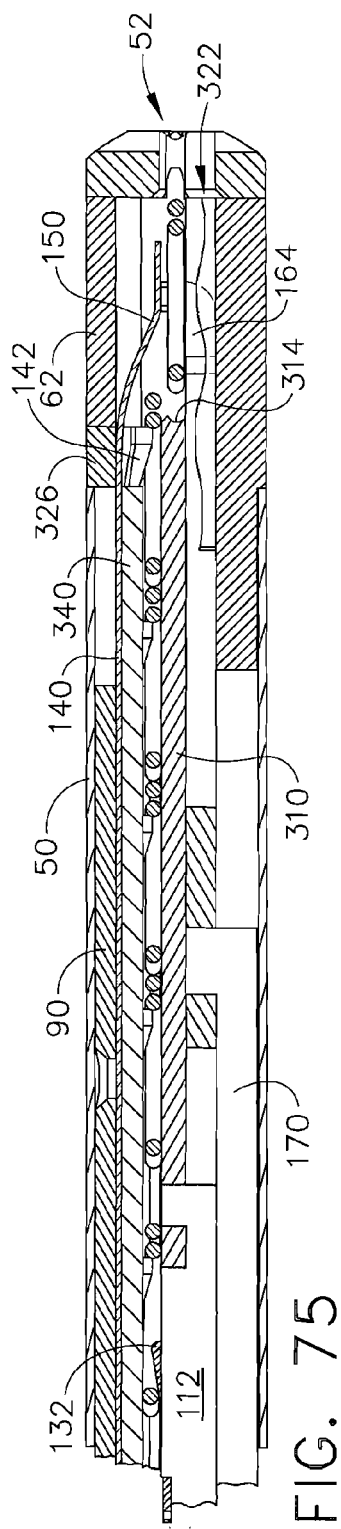

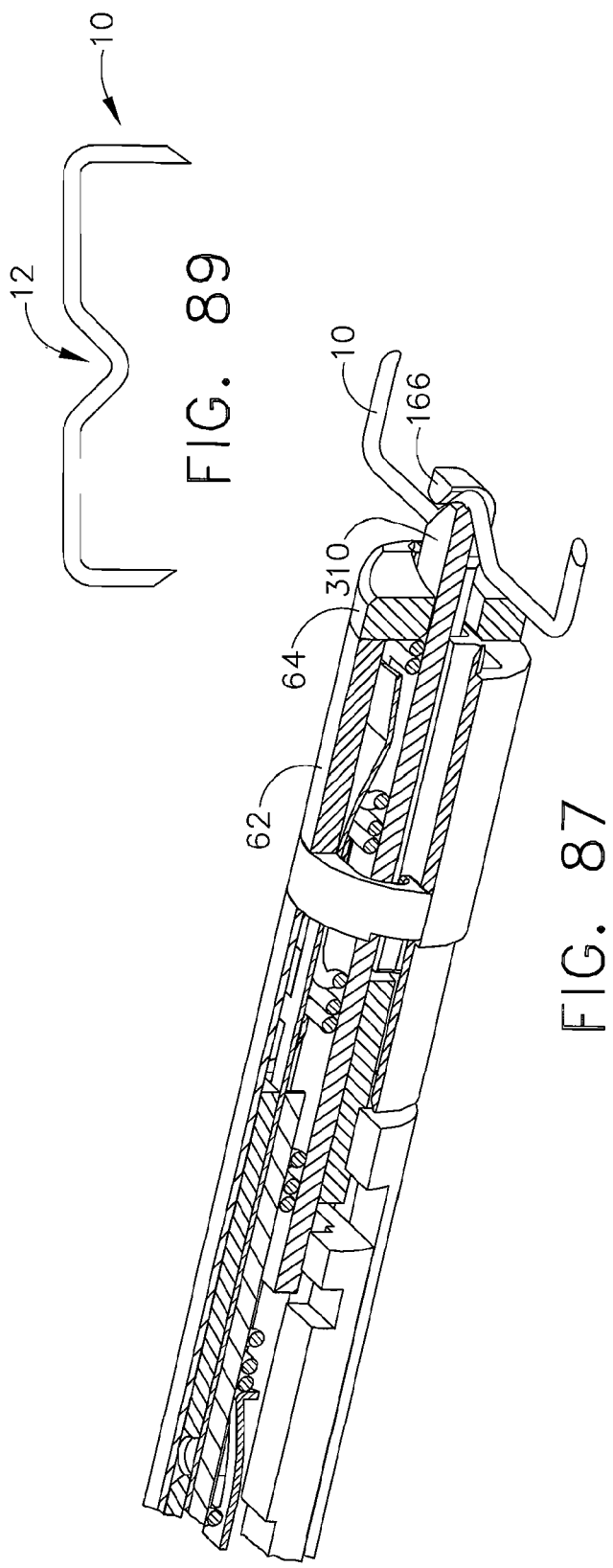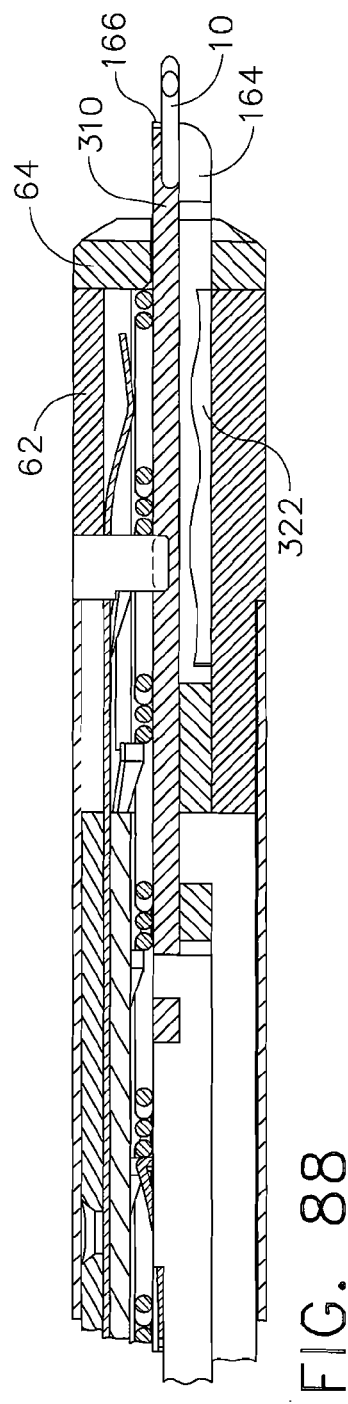

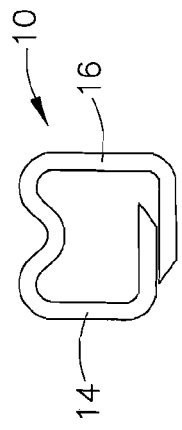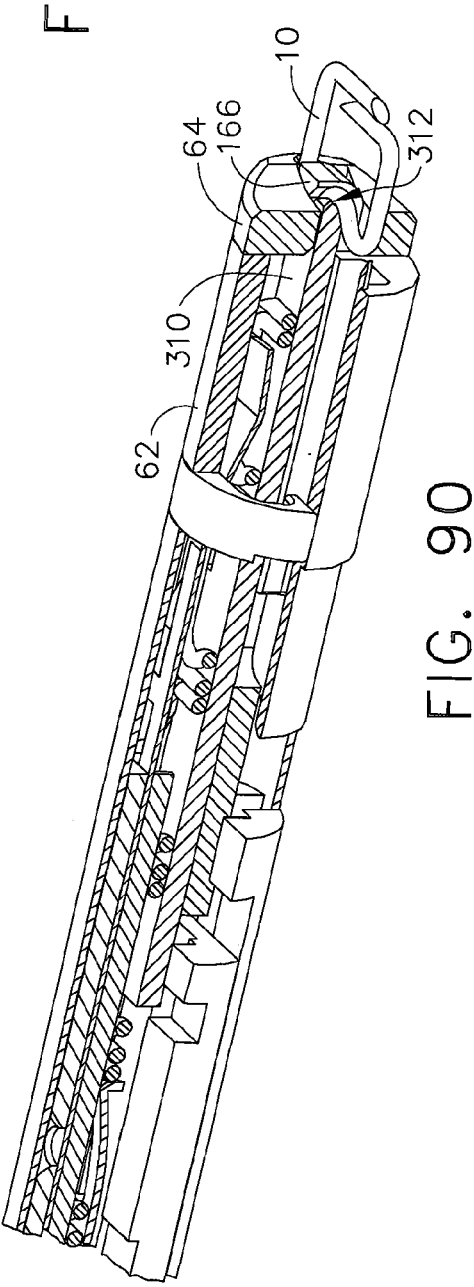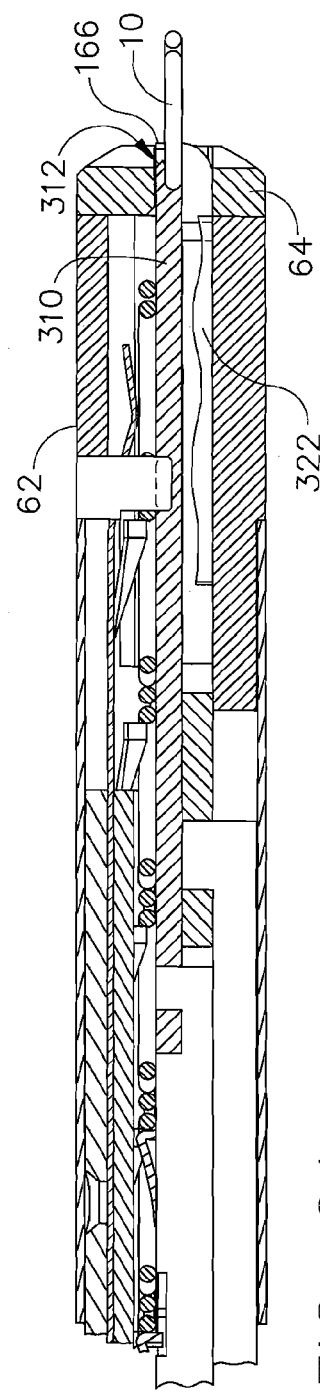

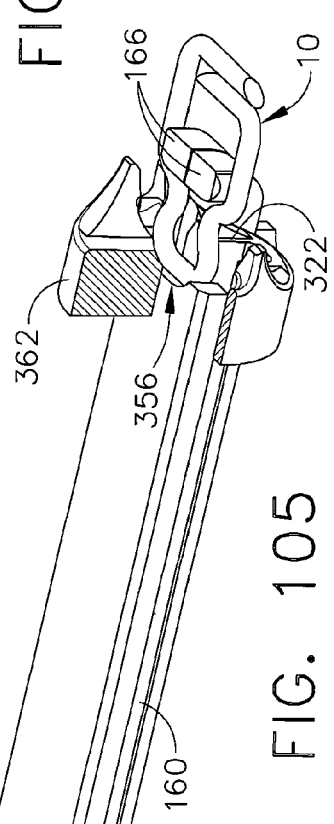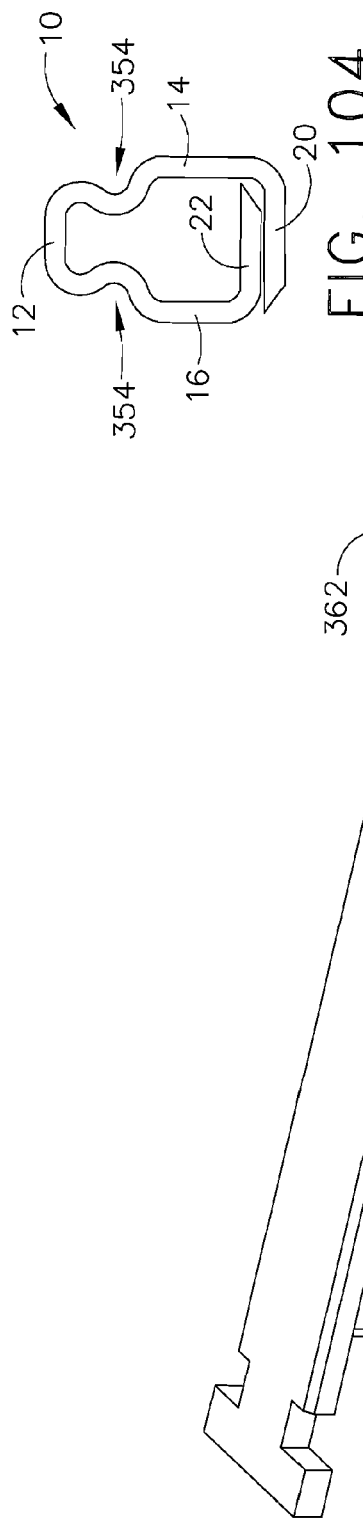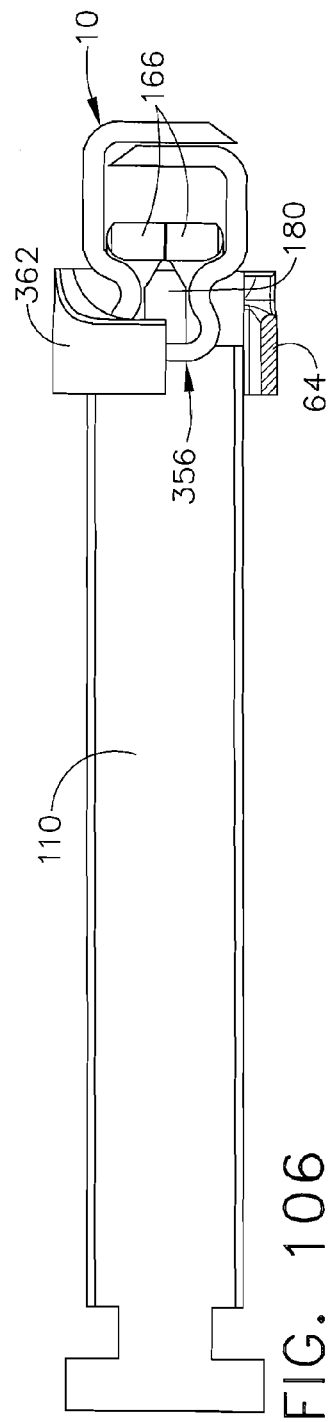

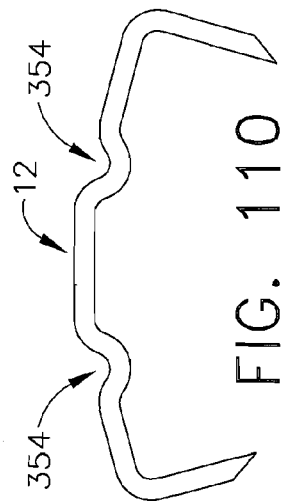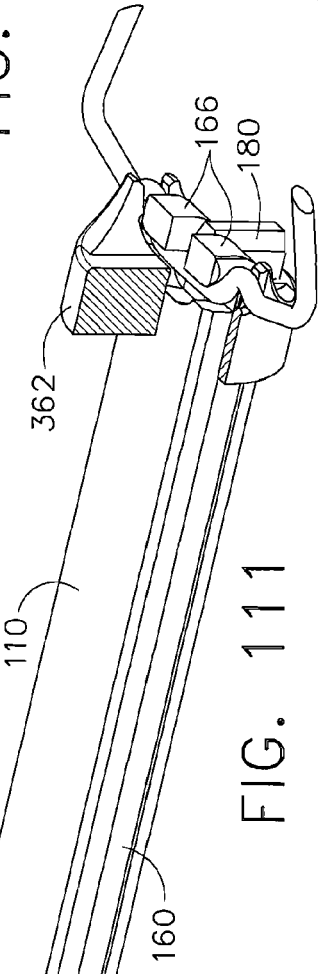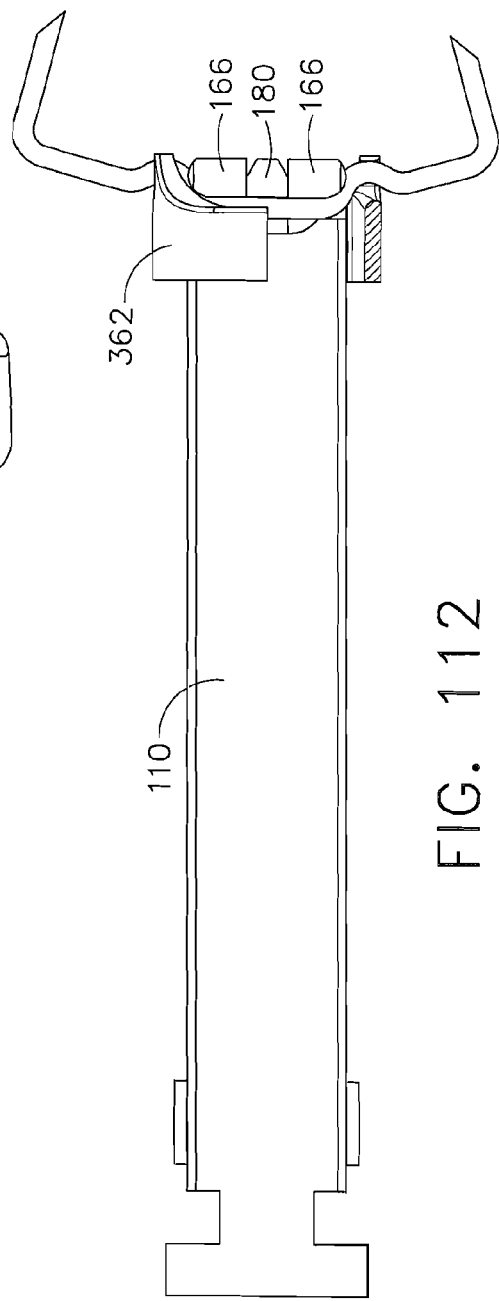

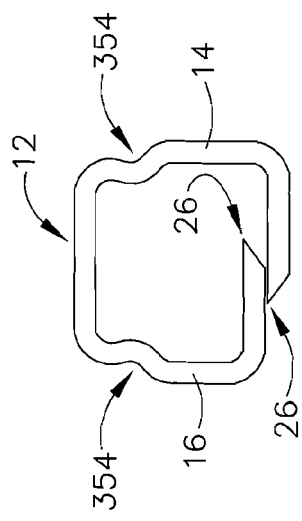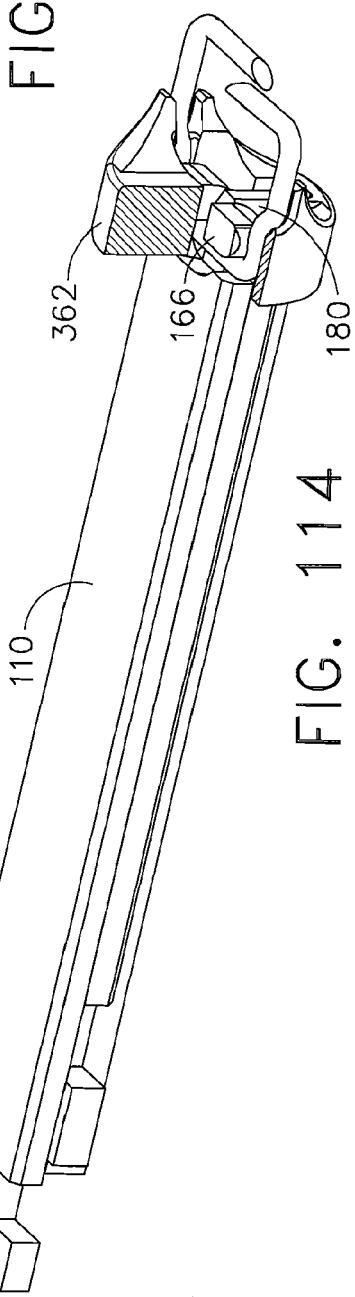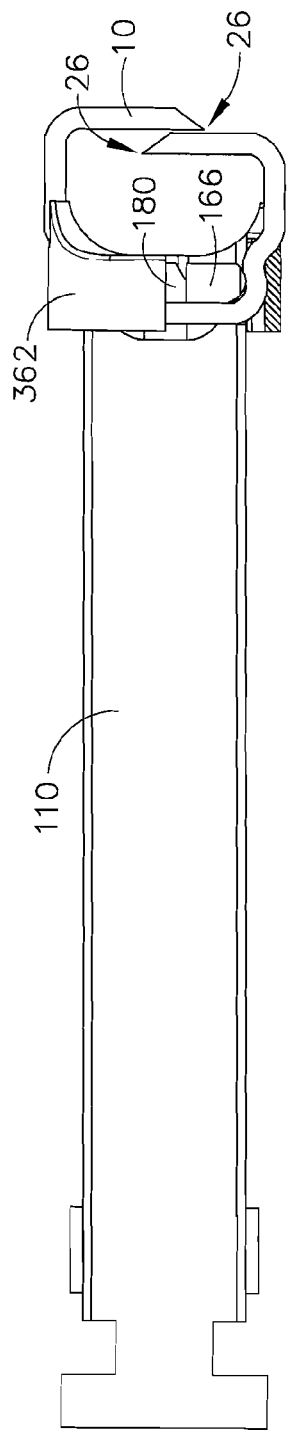

SURGICAL STAPLER FOR APPLYING A LARGE STAPLE THROUGH A SMALL DELIVERY PORT AND A METHOD OF USING THE STAPLER TO SECURE A TISSUE FOLD

This application is a continuation-in-application of, and claims priority of Pending U.S. patent application Ser. No. 12/359,351 filed Jan. 26, 2009; Pending U.S. patent application Ser. No. 12/359,354 filed Jan. 26, 2009 and Pending U.S. patent application Ser. No. 12/359,357 filed Jan. 26, 2009.

FIELD OF THE INVENTION

The present invention relates in general to the joining of cavity wall tissue with a surgical stapler and, more particularly, to a low profile stapler for delivering multiple large-sized box staples to a body cavity through a small delivery port. The low profile stapler enables large areas of tissue to be joined together inside a body cavity through a small access port. The present invention also pertains to methods of using the low profile stapler to approximate tissue within a body cavity during a minimally invasive surgical procedure, such as a gastric volume reduction procedure. The present invention also pertains to the closure of defects on or within the body through secure tissue apposition. The present invention also pertains to the reinforcement of fastened tissues through imbrication of the fastened region secured with the low profile stapler. The present invention also pertains to the attachment of prosthetics to tissue, such as mesh for the repair of a hernia.

BACKGROUND OF THE INVENTION

Obesity is a medical condition affecting more than 30% of the population in the United States. Obesity affects an individual's quality of life and contributes significantly to morbidity and mortality. Obesity is most commonly defined by body mass index (BMI), a measure which takes into account a person's weight and height to gauge total body fat. It is a simple, rapid, and inexpensive measure that correlates both with morbidity and mortality. Overweight is defined as a BMI of 25 to 29.9 kg/m2 and obesity as a BMI of 30 kg/m2. Morbid obesity is defined as BMI≥40 kg/m2 or being 100 lbs. overweight. Obesity and its co-morbidities are estimated to cost an excess of $100 billion dollars annually in direct and indirect health care costs. Among the co-morbid conditions which have been associated with obesity are type 2 diabetes mellitus, cardiovascular disease, hypertension, dyslipidemias, gastroesophageal reflux disease, obstructive sleep apnea, urinary incontinence, infertility, osteoarthritis of the weight-bearing joints, and some cancers. These complications can affect all systems of the body, and dispel the misconception that obesity is merely a cosmetic problem. Studies have shown that conservative treatment with diet and exercise alone may be ineffective for reducing excess body weight in many patients.

A surgical procedure has been developed for involuting the gastric cavity wall to reduce stomach volume as a treatment for obesity. In the gastric volume reduction (GVR) procedure (e.g., reduction gastroplasty, gastric plication, greater curvature plication, etc.), multiple pairs of suture anchoring devices, such as T-Tag anchors, are deployed through the gastric cavity wall. Preferably, the suture anchors are deployed through a small diameter port in a minimally invasive surgical procedure to reduce trauma to the patient. Following deployment of the T-Tag anchors, the suture attached to each individual pair of anchors is cinched to approximate the tissue and secured to involute the cavity wall between the anchors. This procedure is described in greater detail in co-pending U.S. patent application Ser. Nos. 11/779,314 and 11/779,322, which are hereby incorporated herein by reference in their entirety. Procedure variations of particular interest include the case where the involution occurs about the midline of the anterior surface of the stomach and the case where the involution occurs about the greater curvature of the stomach following the removal or relaxing of attachment points along the greater curve (e.g., dissection of the short gastric vessels, dissection of the omentum from the gastric wall, etc.). A sizing device such as a bougie may be used to help determine the appropriate amount of capacity to be reduced. An exemplary bougie size for a greater curvature plication is in the range of 30-40 French, but sizes up to 60 French may be used. Sizes less than 30 French may be used at the surgeons discretion. Improvements to traditional bougies providing steerability, adjustable sizing that is targeted (e.g., at the angularis incisura, antrum, etc.) or broadly along the treatment length, on-board visualization, etc. may be used to facilitate placement and fold creation.

One effect of the procedure is to more rapidly induce feelings of satiation defined herein as achieving a level of fullness during a meal that helps regulate the amount of food consumed. Another effect of this procedure is to prolong the effect of satiety which is defined herein as delaying the onset of hunger after a meal which in turn regulates the frequency of eating. By way of a non-limiting list of examples, positive impacts on satiation and satiety may be achieved by a GVR procedure through one or more of the following mechanisms: reduction of stomach capacity, rapid engagement of stretch receptors, alterations in gastric motility, pressure induced alteration in gut hormone levels, and alterations to the flow of food either into or out of the stomach. As an example, a stomach with a reduced capacity will distend more quickly for a given volume of food. This distension of the stomach may trigger stretch receptors which in turn trigger a sense of satiation. In another example, the procedure will limit the stomach's ability to expand, effectively reducing its capacity or fill volume. Additionally, the procedure may induce a beneficial hormonal effect due either to the more rapid triggering of stretch receptors in certain regions of the stomach or the prevention of hormone release by eliminating triggering mechanisms from being engaged in the infolded region that no longer experiences stretch in the same manner. In yet another example, the procedure may alter gastric emptying by preventing efficient antral contractions. Additionally, the infolded region may provide a restrictive inlet into the stomach just distal to the esophago-gastric junction.

The GVR procedures described in these applications require individual placement of each suture anchor pair into the cavity wall tissue, and subsequent tensioning of the suture between the anchor pairs in order to involute the tissue. This individual placement of the T-Tag anchors and manual suture tensioning is time intensive; increasing the duration, complexity and cost of the GVR procedure. Accordingly, it is desirable to have a simpler, faster, and less expensive means for forming a tissue fold within the peritoneal cavity.

It is known to use surgical staples for binding and holding body tissues together following an anastomosis, skin closure, or other surgical procedure. Traditionally, these staples have had a wide U-shape in the undeformed state, requiring a large incision site or wide diameter trocar cannula to accommodate the staples and stapler. Staples and staplers having a lower profile have been developed for use in smaller diameter (i.e. 5 mm or 10 mm) trocars. However, these devices suffer from a number of deficiencies which make them impractical for use in the GVR procedure. In particular, such staplers require bending the staple a full 180° from the predeployment, stacked condition in the stapler to the closed, deployed condition in the tissue. Obtaining this degree of plastic deformation requires that the staple be composed of a soft, ductile material, such as soft titanium. However, the use of a soft ductile material decreases the strength and holding power of the formed staple, thus making the staple unsuitable for the pressures associated with involuting the gastric cavity wall without an impractical number of staples. Staples having a triangular prefiring configuration have also been developed for deployment through a low profile stapler. However, the triangular shape of these staples prevents the staples from being stacked and fed longitudinally through the stapler shaft. Instead, the staples are stacked and fed vertically within the stapler, which reduces the number of staples that can be deployed from the stapler while still maintaining a low profile diameter. Since some versions of the GVR procedure may require a large number of staples to involute the cavity wall, vertical stacking would necessitate using more than one stapler to complete a procedure. Additionally, previous staplers have bent staples at three or fewer points during formation and deployment, which reduces the amount of work hardening and, thus, strengthening within the formed staple.

Accordingly, to facilitate GVR and other surgical procedures, it is desirable to have an improved surgical staple and deploying stapler for fastening layers of tissue within the peritoneal cavity. It is desirable that the stapler has a low profile for use through a small diameter laparoscopic port, a single trocar containing multiple small laparoscopic ports, or through a semi-rigid or flexible endoscopic platform (e.g., for use in natural orifice surgical procedures, single site laparoscopy, etc.), yet be capable of deploying staples with a large tissue purchase. Further, it is desirable that the staples have a folded, box shape, and that a large quantity of the staples be deliverable by a single stapler during a procedure. Additionally, it is desirable to have a stapler which alters the configuration of a staple from a low profile, reduced width prior to deployment to a wider, operable width following deployment. Furthermore, it is desirable that the staple be comprised of a strong material having a high yield stress, and that the forming process includes greater than 3 bending points to increase the strength of the formed staple. The present invention provides a surgical staple and stapler which achieves these objectives.

SUMMARY OF THE INVENTION

The present invention provides a low profile surgical stapler for deploying staples during a tissue apposition procedure, such as gastric volume reduction surgery. The stapler includes a handle containing at least one actuator. The handle is connected to an elongated stapler housing having distal and proximal ends. A stack of staples is fed longitudinally through the housing to an open stapler end. The staples are individually advanced outside of the stapler and expanded open in response to the actuator. After the staple pierces or otherwise engages the tissue sections to be joined, the stapler draws the expanded staple legs back inward to form the staple through the tissue.

The present invention also provides a staple having a small profile for feeding through a low profile stapler. The staple has a small width, closed loop condition during feeding. During deployment, the staple transforms to a second, condition with a larger width opening for gripping tissue. After gripping onto one or more tissue sections, the staple is transformed to a third, distinct, closed condition, in which the tissue is held firmly by the staple legs. The regions of plastic deformation in transitioning between the different conditions differ to distribute the work hardening over a longer length of the staple back span, thereby increasing the strength of the staple.

Additionally, the present invention provides a method for involuting and securing tissue within the peritoneal cavity. This method includes advancing a staple out an open end of a low profile stapler and opening the staple to an expanded condition, in which the staple prongs face in the direction of a tissue area to be connected. Separate, spaced sections of the tissue are gripped and apposed by the staple prongs. The stapler forms the staple through the tissue between the prongs to hold the apposed tissue together.

BRIEF DESCRIPTION OF THE DRAWINGS

FIG. 1 is a top view of an exemplary staple embodiment of the present invention shown in an initial, undeployed condition;

FIG. 2 is a top view of the staple of FIG. 1 shown in an intermediate deployment condition;

FIG. 3 is a top view of the staple of FIG. 1, showing the staple in a final, deployed condition;

FIG. 10A is a top, fragmentary view, partially in section, of the former body;

FIG. 10B is a side, fragmentary view, partially in section, of the former body;

FIG. 10C is an isometric view, partially in section, of the former body;

FIG. 11A is a top, fragmentary view, partially in section, of the former end cap;

FIG. 11B is a side, fragmentary view, partially in section, of the former end cap;

FIG. 11C is an isometric view, partially in section, of the former end cap;

FIG. 12A is a side view of the clamp;
FIG. 12B is a top view of the clamp;
FIG. 12C is an isometric view of the clamp;
FIG. 13A is a top view of the staple indexer;
FIG. 13B is a side view of the staple indexer;
FIG. 13C is an isometric view of the staple indexer;
FIG. 13D is a bottom perspective view of the staple indexer;
FIG. 14A is a side view of the anvil;
FIG. 14B is a top view of the anvil;
FIG. 14C is an isometric view of the anvil;

FIG. 15A is a fragmentary, side view of the anvil separator;

FIG. 15B is a fragmentary, top view of the anvil separator;

FIG. 21 is a side sectional view of the distal end of the stapler, taken along the longitudinal stapler axis, showing the staple deploying assembly in an initial deployment condition;

FIG. 22 is a side, fragmentary, partially sectional view of the distal stapler end showing the staple deploying assembly in an initial deployment condition;

FIG. 26 is a side sectional view of the distal end of the stapler, taken along the longitudinal stapler axis, showing the clamp advanced distally against the staple and anvil during a second stage in the deployment process;

FIG. 27 is a side, fragmentary, partially sectional view of the distal stapler end, similar to FIG. 26, showing the clamp and staple advanced distally against the anvil;

FIG. 30 is a side sectional view of the stapler, taken along the longitudinal stapler axis, showing the staple held outside the open stapler end by the anvil and clamp during an intermediate stage in the deployment process;

FIG. 31 is a side, fragmentary, partially sectional view of the distal stapler end, showing the clamp, staple and anvil tines in a fully advanced position outside the open stapler end;

FIG. 36 is a side sectional view of the distal stapler end, taken along the longitudinal stapler axis, showing a staple expanded open outside the open stapler end by the anvil and separator;

FIG. 37 is a side, fragmentary, partially sectional view of the distal stapler end showing a staple expanded open outside the open stapler end by the anvil and separator;

FIG. 44 is a side, sectional view of the distal stapler end, taken along the longitudinal stapler axis, showing a staple being formed;

FIG. 45 is a side, fragmentary, partially sectional view of the distal stapler end showing the same deployment stage as FIG. 44;

FIG. 48 is a side sectional view of the distal stapler end, taken along the longitudinal stapler axis, showing the same deployment stage as FIG. 47;

FIG. 49 is a side, partially sectional view of the distal stapler end showing the same deployment stage as FIG. 47;

FIG. 56 is a fragmentary, isometric view, partially in section, of the distal end of the stapler showing the same deployment stage as FIG. 55;

FIG. 57 is a side sectional view of the distal stapler end, taken along the longitudinal stapler axis, showing the same deployment stage as FIG. 55;

FIG. 58 is a side, fragmentary, partially sectional view of the distal stapler end showing the same deployment stage as FIG. 55;

FIG. 62 is a side sectional view of the distal stapler end, taken along the longitudinal stapler axis, showing the same deployment stage as FIG. 61;

FIG. 63 is a side, fragmentary, partially sectional view of the distal stapler end showing the same deployment stage as FIG. 61;

FIG. 72 is an isometric view of the anvil showing the addition of optional staple ejecting members;

FIG. 73 is a top view of the distal anvil end showing the optional staple ejecting members;

FIG. 74 is an isometric view, partially in section, of the distal end of the stapler showing an alternative stapler embodiment in an initial deployment position;

FIG. 75 is a side, partially sectional view of the distal stapler end, similar to FIG. 74, showing a staple deposited by the shoe into the discharge channel at the beginning of the deployment sequence;

FIG. 76 is a top view of an exemplary staple for deployment from the alternative stapler embodiment of FIGS. 74 and 75, shown in an initial, undeployed condition;

FIG. 87 is an isometric view, partially in section, of the stapler of FIG. 74 shown with the spreader advanced to expand open the staple outside of the stapler;

FIG. 88 is a side, partially sectional view of the distal stapler end showing the same deployment stage as FIG. 87;

FIG. 89 is a top view of the staple of FIG. 76, showing the staple in an intermediate, fully open condition;

FIG. 90 is an isometric view, partially in section, of the stapler of FIG. 74 shown with the former advanced to close the staple;

FIG. 91 is a side, partially sectional view of the distal stapler end showing the same deployment stage as FIG. 90;

FIG. 92 is a top view of the staple of FIG. 76, showing the staple in an final, closed condition;

FIG. 104 is a top view of an alternative staple embodiment shown in an initial, undeployed condition;

FIG. 105 is a partial, isometric view of the distal end of the stapler showing another alternative stapler embodiment with a staple over the anvil tines and the clamp engaging the staple back span prior to opening;

FIG. 106 is a partial, top view of the alternative stapler embodiment and deployment stage shown in FIG. 105;

FIG. 110 is a top view of the alternative staple of FIG. 104 showing the staple in a fully open condition;

FIG. 111 is a partial, isometric view of the stapler of FIG. 105 showing the clamp driving the staple back span against the anvil tines to fully open the staple;

FIG. 112 is a partial, top view of the alternative stapler embodiment and deployment stage shown in FIG. 111;

FIG. 113 is a top view of the alternative staple of FIG. 104 showing the staple in a final, closed condition;

FIG. 114 is a partial, isometric view of the stapler of FIG. 105 showing the former advanced against the staple legs to close the staple; and FIG. 115 is a partial top view of the alternative stapler embodiment and deployment stage shown in FIG. 114.

DETAILED DESCRIPTION OF THE INVENTION

Figure 4:
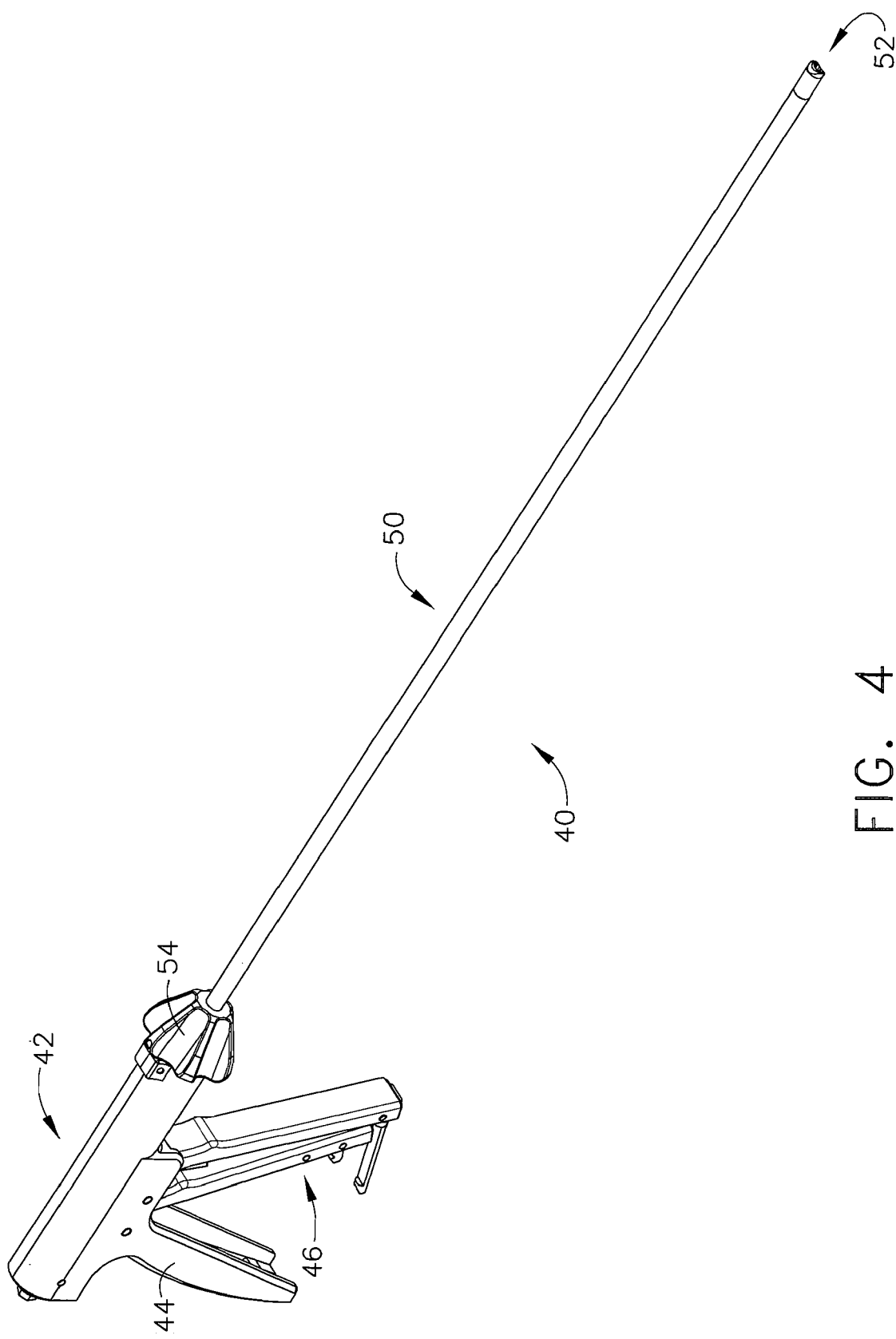
FIG. 4 is an isometric view of an exemplary low profile surgical stapler of the present invention.

Referring now to the drawing figures, in which like numerals indicate like elements throughout the views, FIG. 1 illustrates a first exemplary fastener or staple 10 of the present invention in an initial, undeployed configuration. As shown in FIG. 1, staple 10 comprises a length of wire formed into a back span 12 and first and second leg portions 14, 16 that intersect with opposite ends of the back span. The wire has a cylindrical cross-section, but may have other shapes (e.g., rectangular, elliptical, etc.) to provide optimal strength for the application or to aid in the feeding of the staples and may or may not be uniform along the length of the wire. Leg portions 14, 16 intersect with back span 12 at an approximate angle α of 90° and extend in a substantially parallel fashion forward of the back span. In an embodiment wherein the deploying device contains multiple staples, substantially parallel leg portions are able to slide through a channel of uniform rectangular cross section while strictly maintaining their orientation, allowing for repeatable firing of the device without jamming. In one embodiment, the angle α is chosen to be greater than 90° to aid in the feeding of staples by increasing friction in the system to eliminate unintended staple movements. In an alternative embodiment, the angle α is chosen to be less than 90° to aid in the feeding of staples by reducing friction in the system thus minimizing force transmission requirements within the handle. Leg portions 14, 16 need not be straight for leg portions to be substantially parallel. The distance between staples legs 14, 16 describes an initial width dimension $w_i$ for the staple 10. The staple wire may have a cylindrical or other shape (e.g., rectangular, elliptical, etc.) cross-section to provide optimal strength for the application, and the cross-sectional shape may or may not be uniform along the length of the wire. In one embodiment regions of a circular wire have been altered to contain flat surfaces, or have had their cross-section modified to a more oval or elliptical shape providing a more flat surface to push on. Such surfaces include but are not limited to back span 12 or end segment 22.

Opposite back span 12, leg portions 14, 16 are bent inward to form staple end segments 20, 22. In an initial configuration (for feeding), the staple may have a closed-form, loop shape with each side of the loop having at least one portion of the length of wire forming the shape. In a loop shape, two lengths of wire may be disposed across one side of the shape to enclose the shape, as demonstrated by the end segments 20, 22. The tips of end segments 20, 22 are angled to form sharp prongs 26 for piercing tissue. Prongs 26 may be formed on end segments 20, 22 in any desired manner and may have features incorporated to aid in penetration or to aid in hooking (e.g., barbed, etc.) tissue that has been penetrated. However, it is preferable that prongs 26 be formed by a sloping surface tapering inward from an outer edge of the end segment towards an inner edge thereof. Back span 12 is preferably non-linear between leg portions 14, 16. The back span can be made non-linear by providing a shallow depression at a midpoint of the span, such as indicated by reference number 30, or other type of deformation of the wire at one or more points along the length of the span. A non-linear back span aids in the feeding and alignment of the staples during deployment. One skilled in the art will recognize that other features may be added to staple 10 to aid in the feeding and alignment of the staples without departing from the spirit of this invention.

Staple legs portions 14, 16 are bent at end segments 20, 22 to make one of the leg portions at least one wire diameter longer in length than the other leg portion. The longer length of one leg portion (i.e. staple leg 14 in FIG. 1) enables the end segments 20, 22 to lie in a common plane with back span 12. Lengthening one staple leg portion relative to the other staple leg portion minimizes the vertical profile of the staple in the undeployed condition, allowing the staples to be fed through a smaller area within the stapler. In the undeployed condition, end segments 20, 22 are bent to a length that is less than or equal to the length of back span 12. The lengths of the end segments 20, 22 can be made equal by changing the angle defined by one of the leg portions and end segments (as shown by leg 16 and segment 22 in FIG. 1) to less than 90° while keeping the end segment substantially straight. In an alternative embodiment (not shown), this is accomplished by providing a curve or bend to end segment 22. Both of these configurations still maintain the closed-form shape and are asymmetric. Further, the angulation of end segment 22 may help prevent rotation of the staple once implanted in tissue. In yet another alternative embodiment, staple leg portions 14, 16 may also be slightly curved or bowed in the outward direction so that in its final formed position the tissue tension generally will keep the back span 12 of the staple parallel to the fastened tissue. In some applications, this may be advantageous to help secure the staple and keep the leg from rotating out of the fastened tissue. End segment 22 may also be substantially parallel to end segment 20 (and therefore of a shorter length) without departing from the scope of the overall invention.

Staples used in this application are preferably biocompatible, implantable, and may optionally be absorbable. A non-limiting list of candidate materials includes: metals such as titanium and its numerous alloys, stainless steel, nitinol, magnesium, and iron; plastics such as PEEK, Prolene™; absorbable materials such as PDS™, Vicryl™, and polylactic acid (PLA); and combinations of these classes of materials. Further, these fasteners may contain therapeutic agents that are selectively or immediately released over time to aid in healing, prevent infection (e.g., triclosan), reduce swelling or edema, etc.

FIG. 2 shows staple 10 in a second, intermediate deploying condition. In this intermediate state, staple legs portions 14, 16 are bent outward to describe a maximum width $w_m$ between the distal tips of the staple legs. In FIG. 2, staple legs 14, 16 are shown expanded open approximately 180° into substantially lateral alignment with the initial back span position, with end segments 20, 22 projecting distally.

However, it should be understood that staple legs 14, 16 can be expanded open to an angle less than or greater than 180°. Staple legs 14, 16 are bent outward by applying a deploying force (indicated by arrows 32 in FIG. 1) to the inside of each staple leg 14, 16, adjacent the intersection between the leg and back span 12. The outward deploying forces 32 are applied to staple legs 14, 16 while back span 12 is held fixed. The application of forces 32 against the fixed staple legs 14, 16 pulls the staple legs outward, expanding open the staple. As staple legs 14, 16 are bent outward, back span 12 retains a non-linear characteristic. The outward bending of staple legs 14, 16 creates an enlarged opening into the staple 10 that is preferably in the range of twice the width of the stapler housing.

Staple 10 is transformed to a third, fully deployed form, shown in FIG. 3, by the application of force to laterally spaced points along staple legs 14, 16. This force application is indicated by arrows 34 in FIG. 2. It will be appreciated that the force application points in transitioning from the intermediate to fully deployed conditions differ from the force application points in transitioning from the initial to intermediate deployment conditions. The separate force application or bending points in the deployment process increase the length of wire subject to work hardening, thereby increasing the strength of the staple. In the final deployment condition, staple leg portions 14, 16 are drawn back towards the center of the staple, with prongs 26 again pointing inward through the intervening tissue (not shown) to penetrate and hold the tissue. The length of staple 10 decreases between the initial and final deployment conditions, with an ensuing increase in the staple width, so that the final width dimension $W_f$ of the formed staple (described by the distance between staple legs 14, 16) is greater than the initial width dimension $W_i$. During deployment, staple 10 transitions between the initial, intermediate and final, formed conditions in a series of steps which may be substantially simultaneous, but which are preferably carried out sequentially, so as to first open staple 10 to the intermediate condition of FIG. 2, and then bend each of the staple legs 14, 16 back around into the formed condition shown in FIG. 3. Note that the asymmetric configuration of the staple ends 20, 22 will be transformed into a similarly asymmetric shape in the formed staple as depicted in FIG. 3. During staple transformation the staple back span maintains substantially the same size and shape. The staple shown in FIGS. 1-3 is intended to be one non-limiting example of a closed-form staple with substantially parallel legs. Additional staple designs, applicators, procedure applications, and methods of use are disclosed in co-pending U.S. patent application Ser. No. 12/359,351 filed Jan. 26, 2009 entitled "A SURGICAL STAPLER FOR APPLYING A LARGE STAPLE THROUGH A SMALL DELIVERY PORT AND A METHOD OF USING THE STAPLER TO SECURE A TISSUE FOLD", which is hereby incorporated herein by reference in its entirety. In applying the staple designs disclosed in U.S. patent application Ser. No. 12/359,351 to the present invention, the staple designs would preferably include a non-linear back span. In addition to the staple designs disclosed herein, it is anticipated that other alternative staple designs may also be conceived and used with the present invention without departing from the scope of the invention.

Turning now to FIG. 4, which shows an exemplary low profile stapler 40 for deploying staples 10 in accordance with the invention. As shown in FIG. 4, stapler 40 includes a handle 42 having a pistol grip 44 shaped for grasping by a surgeon. An actuator assembly 46 is movably coupled to handle 42 to be drawn towards the pistol grip 44 during staple deployment. An elongated staple housing 50 extends distally from handle 42. Housing 50 has sufficient length (on the order of 18") to enable use within an obese patient at numerous trocar access sites. Likewise, housing 50 is sized to allow for passage through a small (3-5 mm) diameter trocar, although functional devices of a larger diameter are also possible without departing from the overall scope of the invention. A staple deploying assembly, described below, is at least partially disposed within the interior of housing 50 for discharging staples from a distal deployment opening 52. Actuator assembly 46 facilitates both the advancement of staples 10 through housing 50, as well as the deployment of the staples from the distal opening 52. Alternatively, separate actuating mechanisms may be incorporated into stapler 40 for conveying staples to the distal stapler opening 52 and deploying the staples externally from the stapler into adjacent tissue.

In a surgical application, stapler 40 is manipulated through a trocar containing one or more ports (in a traditional laparoscopic procedure, single site laparoscopic procedure, etc.) or on a flexible endoscopic platform (in natural orifice, endoluminal, transluminal, or single site laparoscopic procedures) so that deployment opening 52 is adjacent the tissue area to be fastened. Staple housing 50 may be rotated relative to handle 42 to change the orientation of deployment opening 52. One manner of rotating housing 50 is by way of a knob 54 connected about the circumference of the housing. Knob 54 includes a flange 56, shown in FIG. 5, which rotates within a slot at the distal end of handle 42. One or more knob pins 58 extend through knob 54 into or through the wall of housing 50. As knob 54 is rotated, housing 50 is in turn rotated by the interaction of pin(s) 58 with the housing. A connection also exists between knob 54 and the staple deploying assembly inside of housing 50, as will be described in more detail below, so that rotation of the knob also produces rotation of the staple deploying assembly about the longitudinal housing axis. Accordingly, as housing 50 rotates, the legs of staple 10 rotate relative to the surrounding tissue, thereby altering the position at which the staple prongs will pierce the tissue during deployment. Stapler 40 is depicted as having a rigid housing 50 for open surgical applications or laparoscopic applications using trocars. In an alternative embodiment for open surgical applications or laparoscopic applications using trocars, housing 50 is substantially rigid, but has at least one articulation joint allowing housing 50 to deflect in a controlled manner from the primary axis of housing 50, increasing the operable range of the stapler, without departing from the scope of the invention. In yet another alternative configuration, housing 50 is substantially flexible and of an increased length allowing for less invasive, natural orifice (e.g., transoral, etc.) access to regions of the patient requiring a treatment (e.g., within the peritoneal cavity of the patient). In each of these configurations, it is conceived that the device may also be compatible with a single trocar containing multiple ports.

Figure 6:
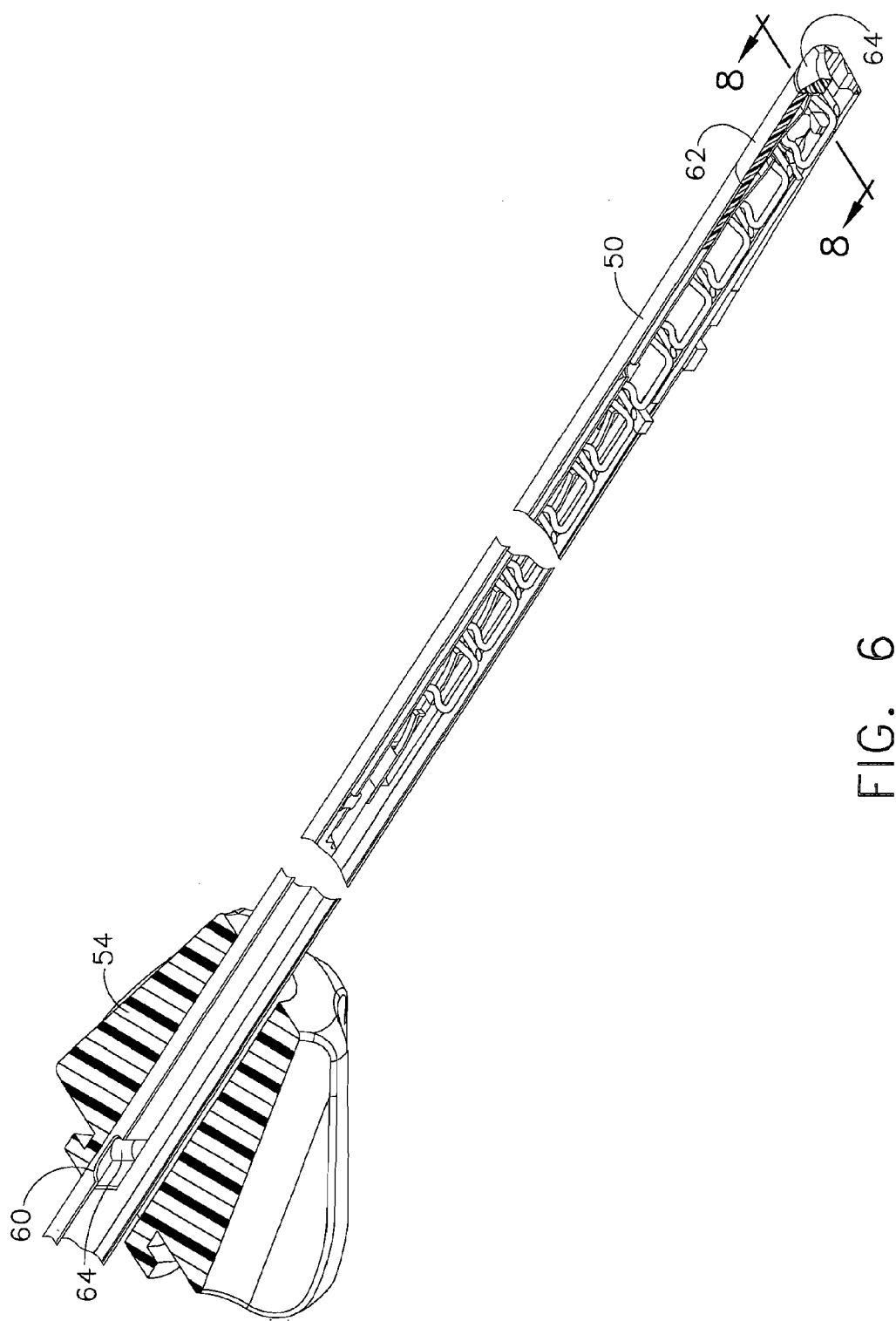
FIG. 6 is an isometric view, partially in section, of the stapler of FIG. 4.
Figure 7:
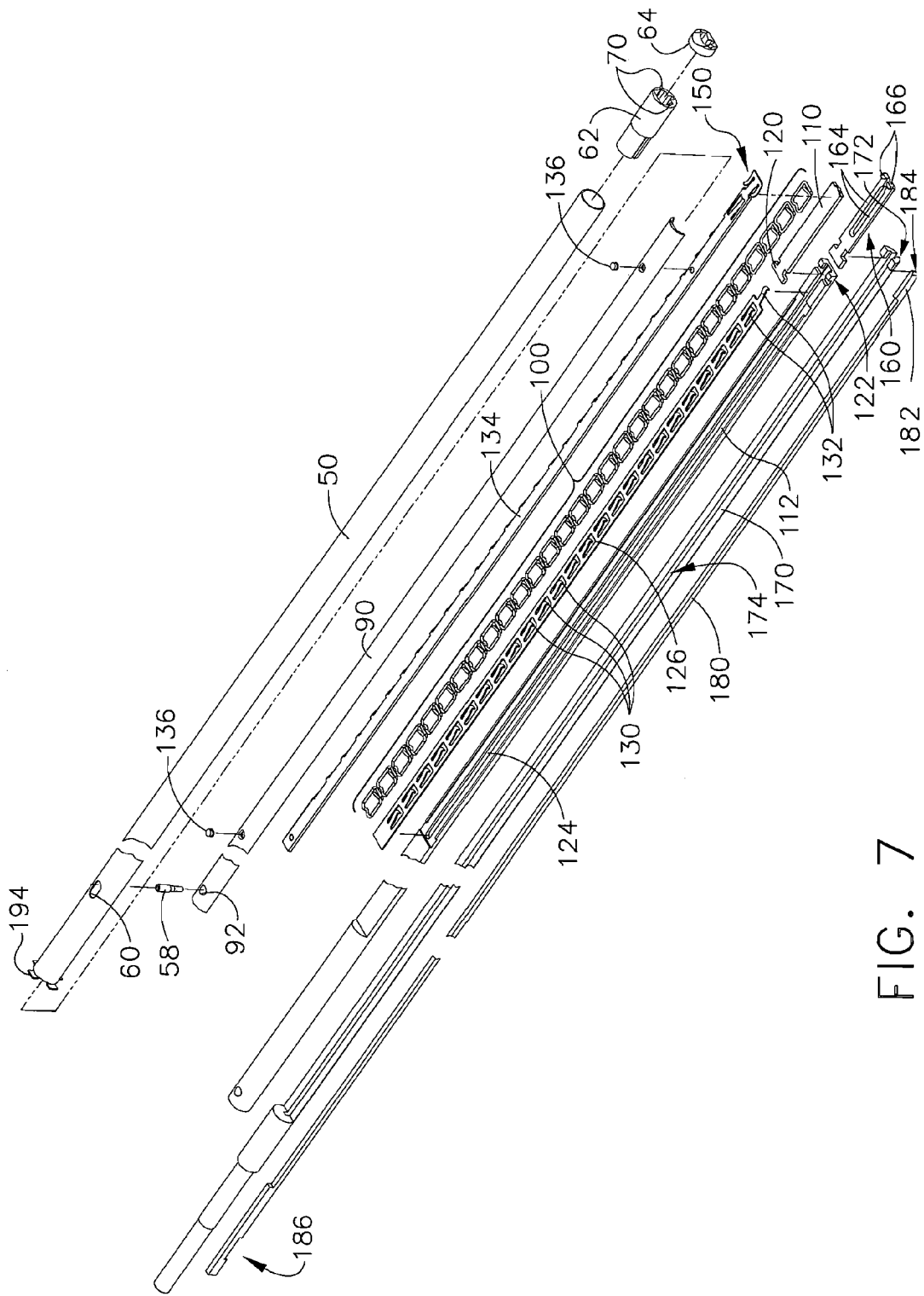
FIG. 7 is an exploded isometric view of the distal end of the stapler of FIG. 4.
Figure 8:
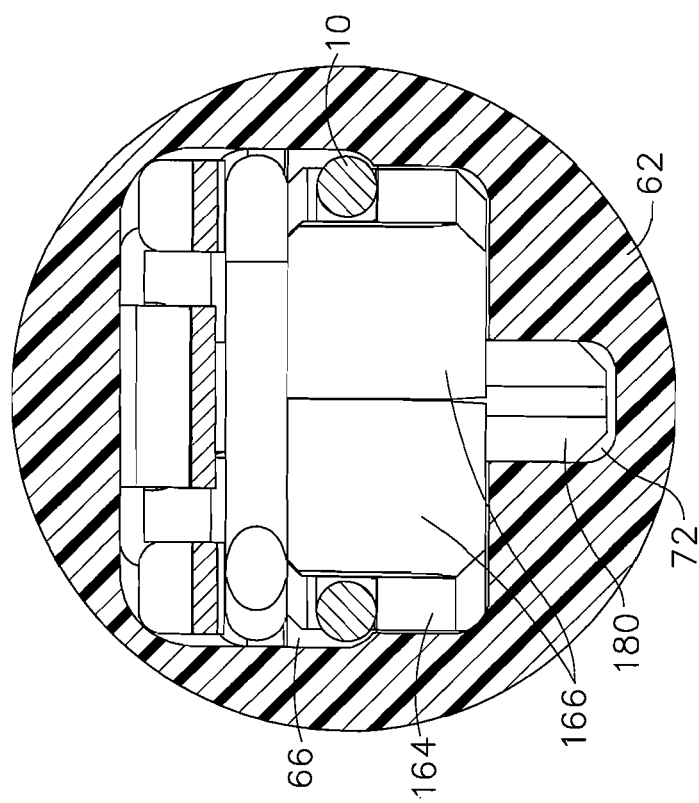
FIG. 8 is a cross-section view of the distal end of the stapler taken along line 9-9 of FIG. 6.

FIGS. 6 through 9 provide several views of an exemplary staple deploying assembly for stapler 40. As shown in these views, the staple deploying assembly includes a staple former attached to and extending from the distal end of housing 50 for forming and closing staples. In the exemplary embodiment, the staple former comprises a cylindrical body 62 and an attached end cap 64. As shown in greater detail in FIGS. 10A-10C, former body 62 includes an interior, longitudinally extending channel 66 having stepped, substantially parallel sidewalls. As shown in FIG. 8, the upper portion of the former body sidewalls are spaced apart a distance substantially equal to the initial width $w_i$ of the staple and the staple leg diameters, to allow unformed staples to pass unobstructed through the former body. The lower portion of the former body sidewalls are spaced apart a distance substantially equal to the width of a pair of anvil arms 164 to allow the anvil arms to pass through the former body.

Diametrically opposed setting radii 70 project forward from the distal end of former body 62. Setting radii 70 have an inwardly concave face that substantially conforms to the outer circumference of the staple wire. Setting radii 70 (one is shown in FIGS. 10A-10C) impact staple 10 during formation, plastically deforming the outer edges of the intersection between back span 12 and staple legs 14, 16. This deformation relieves tension in the outer portion of the staple material in these regions and helps reduce or eliminate the need for overbending helping to eliminate micro fractures that may occur. A general relation for the radius (S) of the setting radii 70 is: S=1.4(WD)+(BR) where (WD) is the wire diameter and (BR) is the inside bend radius of the staple which is defined by the anvil geometry. As shown in FIG. 10C, former body 62 also includes a longitudinally extending recess 72 along the bottom of channel 66 approximately midway across the width of the channel. Recess 72 accommodates an anvil separator as will be described in more detail below.

Figure 9:
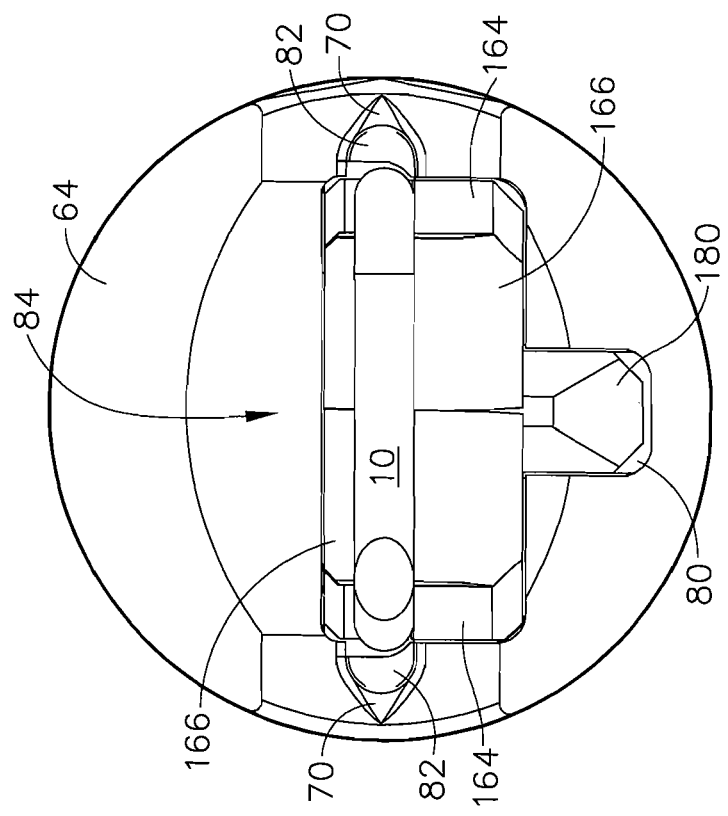
FIG. 9 is a distal end view of the stapler.

Returning to FIG. 7, former end cap 64 is connected to the distal end of former body 62 to extend out coaxially with the former body and staple housing 50. As shown in greater detail in FIGS. 11A-11C, end cap 64 includes a longitudinally extending inner channel 76 and recess 80 which abut against channel 66 and recess 72 of former body 62. The height of end cap channel 76 is reduced from that of former body channel 66 to limit the staple deploying components that can pass through the end cap. End cap 64 also includes diametrically opposite concave grooves 82 formed into the sidewalls of channel 76. As can be seen in FIG. 9, the radius of each groove 82 is substantially the same as the radius of the staple wire to allow the grooves to engage the staple legs 14, 16 as the former advances over the staple during deployment. Setting radii 70 on former body 62 project distally forward into grooves 82. End cap 64 also includes an inwardly curved distal face as indicated at 84. The inward curve 84 and angled faces of the end cap 64 provides better visibility, either laparoscopically or endoscopically, of an exposed, open staple 10. While the staple former is shown and described herein as being composed of two separate yet joined pieces, the former may also be manufactured as a single piece having the described features without departing from the scope of the invention. Aside from traditional or otherwise standard manufacturing techniques for those skilled in the art, it is conceived that a one-piece former would be well suited for Metal Injection Molding (MIM) which would allow this part to made a higher volumes at a reasonable price.

Returning to FIG. 7, a staple guide 90 is located proximal of former body 62 inside staple housing 50. The outer perimeter of staple guide 90 is shaped to conform to the inner circumference of housing 50. Staple guide 90 extends concentrically within staple housing 50 and includes a proximal opening 92 for receiving knob pin 58. Pin 58 extends through staple guide opening 92 and staple housing opening 60 to laterally fix the guide and housing together for rotation. Inserting knob pin 58 into staple guide opening 92 fixes the longitudinal position of the staple guide 90. As shown in FIGS. 6 and 7, staple housing opening 60 has a slotted shape with a greater longitudinal length than staple guide opening 92 and knob pin 58. The longer length of housing slot 60 enables staple housing 50 to reciprocate along the longitudinal stapler axis relative to the fixed staple guide 90. As housing slot 60 slides relative to the fixed pin 58, the staple former is advanced and retracted at the distal end of housing 50. The proximal and distal ends of housing slot 60 can serve as end stops for the advancement and retraction of the staple former.

As shown in FIG. 7, a stack 100 of staples 10 extends longitudinally through housing 50 beneath staple guide 90. Staples 10 are conveyed within stack 100 to the distal end of the stapler prior to deployment. Within stack 100, each staple 10 is oriented such that the abutting end segments 20, 22 of the staple are positioned nearest the open stapler end 52. The back span 12 of the distal-most staple abuts the end segments 20, 22 of the second staple, while the back span of the second staple abuts the end segments of the third staple, and so forth through the length of the stack. The legs 14, 16 of each staple 10 are aligned substantially parallel to and may be in contact with the walls of staple guide 90 to maintain the forward orientation of the staples. Any number of staples 10 can be included within stack 100, with the preferred stapler embodiment capable of holding 20 or more staples.

A staple clamp 110 and clamp extension 112 extend beneath staple stack 100 on the side opposite staple guide 90. As shown in greater detail in FIGS. 12A-12C, staple clamp 110 comprises an elongated strip having substantially planar upper and lower surfaces and a width slightly larger than the initial width $w_i$ of the unformed staples 10. The distal end of clamp 110 is shaped for mating engagement with staple back span 12. In FIGS. 12A-12C, clamp 110 is shown with an arcuate projection 114 extending from the distal end. Arcuate projection 114 fits up against radial depression 30 of the exemplary staple shown in FIG. 1, when the staple is staged for deployment. Arcuate projection 114 mates with radial depression 30 to ensure alignment (centering of the staple on clamp 100 as well as planar alignment) of staple 10 for passage through end cap 64 in the plane of the discharge channel. Additionally, the distal end of clamp 110 includes an inward radius, as indicated at 116, which is substantially equal to the radius of the staple back span 12. Radius 116 aids clamp 110 in engaging and holding staple 10 during the deployment process. FIGS. 12A-12C depict a concave groove 116 and arcuate distal projection 114 on clamp 110, however, it should be appreciated that the distal clamp face may have other shapes (e.g., rectangular, elliptical, angled, etc.) or features to provide optimal and secure contact between the clamp and staple back span during staple deployment.

The distal end of staple stack 100 resides along the surface of clamp 110 prior to the dropping of the individual staples into a discharge channel for deployment. The proximal end of clamp 110 is notched on opposite sides to form a T-connector 120. As can be seen by returning to FIG. 7, clamp extension 112 includes a notched distal end 122 into which T-connector 120 is inserted to attach the clamp to the extension. Proximal of this attachment, clamp extension 112 comprises an elongated strip having upstanding side edges that extend co-axially within staple housing 50, through the proximal open end of the housing. Clamp extension 112 includes a longitudinally extending trough 124, midway across the width of the strip, which extends beneath staple stack 100. While clamp 110 and clamp extension 112 are shown attached by a mating T-connector and notch, it is anticipated that numerous other attachment methods may be utilized for joining the clamp and clamp extension of the present invention without departing from the spirit and scope of the invention.

A staple pusher 126 is located along the surface of clamp extension 112 between the clamp extension and staple stack 100. The upstanding side edges of clamp extension 112 provide a frame for laterally aligning the staple pusher 126 on the clamp extension. The proximal end of staple pusher 126 abuts against a stepped edge on clamp extension 112 to prevent the staple pusher from moving proximally relative to the clamp extension.

Staple pusher 126 advances and retracts with clamp extension 112 inside housing 50 to index staple stack 100 distally. Staple pusher 126 includes a series of longitudinally spaced openings, indicated by numeral 130, with successive openings being spaced a distance greater than or minimally substantially equal to the length of staple legs 14, 16 in an unformed staple 10. It is conceived that uniform, larger distances between successive openings will help increase device reliability allowing for part tolerances. A distally extending spring arm 132 is connected at the proximal end of each staple pusher opening 130, as well as at the distal end of the staple pusher 126. The free end of each spring arm 132 inclines upwardly towards a staple 10 in stack 100. The distal tip each spring arm 132 is bent down substantially perpendicular to the length of the arm to form a staple abutting face. The lower edge of each staple abutting face extends down into clamp extension trough 124. The spring arm faces abut against the inner-most, potentially angled end segments 22 on the unformed staples 10 with each spring arm 132 in contact with a different staple in stack 100. Each spring arm staple face is angled to coincide with the angle of staple end segment 22, so that the spring arm and staple end segment abut across substantially the full width of the spring arm. As clamp extension 112 moves distally, the spring arms 132 apply pressure against the staple end segments 22 to push the staple stack 100 distally within housing 50.

A staple indexer 134 extends longitudinally adjacent staple stack 100, on the side opposite staple pusher 126. Staple indexer 134 combines with staple guide 90, clamp 110, and clamp extension 112 to form a magazine channel through which staple stack 100 is conveyed. Staple indexer 134 is attached to staple guide 90, such as by the proximal and distal rivet pins 136 shown in FIG. 7, to fix the staple indexer in a stationary position within the staple deploying assembly. In the exemplary embodiment shown in greater detail in FIGS. 13A-13D, staple indexer 134 includes a planar body 140 with depending side edges. A series of staple holding arms 142 are formed in one of the side edges. Holding arms 142 are connected at a proximal end to body 140, while the distal end extends below the body and is flexible relative to the longitudinal axis of the staple indexer body. Within the staple deploying assembly, each of the holding arms 142 depends downward into the loop of a different staple in stack 100. Within the folded staple 10, the distal tip of the holding arm 142 contacts the inner folded end segment 22 to form a proximal end stop for the staple. The contact between the stationary holding arms 142 and the stacked staples 10 prevents staple stack 100 from moving proximally within housing 50, particularly during retraction of clamp extension 112 following a staple deployment.

In addition to holding arms 142 along the side of body 140, a center holding arm 144 is formed near the distal end of staple indexer 134. Center holding arm 144 depends through an opening 146 in staple indexer 134 and into contact with the distal-most staple in stack 100. As stack 100 advances distally, holding arms 142, 146 flex in and out of the closed loops of the stacked staples, so that after each deployment the staples in stack 100 are indexed distally one holding arm. A shoe 150 extends in a flexible manner at the distal end of staple indexer 134. Shoe 150 transfers individual staples 10 from stack 100 to the discharge channel during the deployment process, as will be described in more detail below. As an alternative to the staple indexer 134 shown in FIGS. 13A-13D, a staple indexer can be formed with a series of openings 146 along the longitudinal length of the body. In this alternative embodiment, center holding arms 144 depend downwardly from a midpoint of the indexer body, through the openings 146, and into each loop of the folded staples 10, replacing the side holding arms 142 shown in FIGS. 13A-13D. Without departing from the scope of the invention, it is conceived that side holding arms 142 or center holding arms 144 may alternatively engage unformed staples 10 along one or more points of backspan 12. It is also conceived that staple guide 90 and staple indexer 134 may be manufactured as a single component. In a preferred embodiment, the combined guide and indexer are molded out of plastic with holding arms designed to deform during distal indexing of staples 10 while preventing proximal indexing of staples 10.

Returning now to FIG. 7, an anvil body 160 extends longitudinally beneath clamp 110 on the side opposite staple stack 100. As shown in greater detail in FIGS. 14A-14C, anvil 160 includes a T-connector 162 at a proximal end. Distal of connector 162, anvil body 160 forks into a pair of longitudinally extending anvil spring arms 164 separated by a gap. Anvil arms 164 have an inward bias with the gap between the arms decreasing in the distal direction. Anvil arms 164 are angled distally inward towards the longitudinal centerline of the anvil at the distal end of the arm gap. Each of the anvil arms 164 terminates in an upwardly curved, staple holding tine 166. Anvil tines 166 extend substantially perpendicular to the longitudinal length of anvil arms 164. The proximal face of each anvil tine 166 preferably has a radius formed therein, and is rounded about the outer edge and angled distally inward towards the longitudinal centerline of the anvil. The radius formed on the proximal face of each anvil tine 166 helps to securely hold staple 10 in position during the deployment process. Anvil body 160 combines with the distal face of clamp 110 and former body 62 to form the discharge channel of the staple deploying assembly. Clamp 110 extends substantially along the surface of anvil arms 164 and conveys staples at the distal end of stack 100 to the discharge channel. Clamp 110 preferably has as small a length as necessary to cover the anvil arms 164.

Figure 15C:
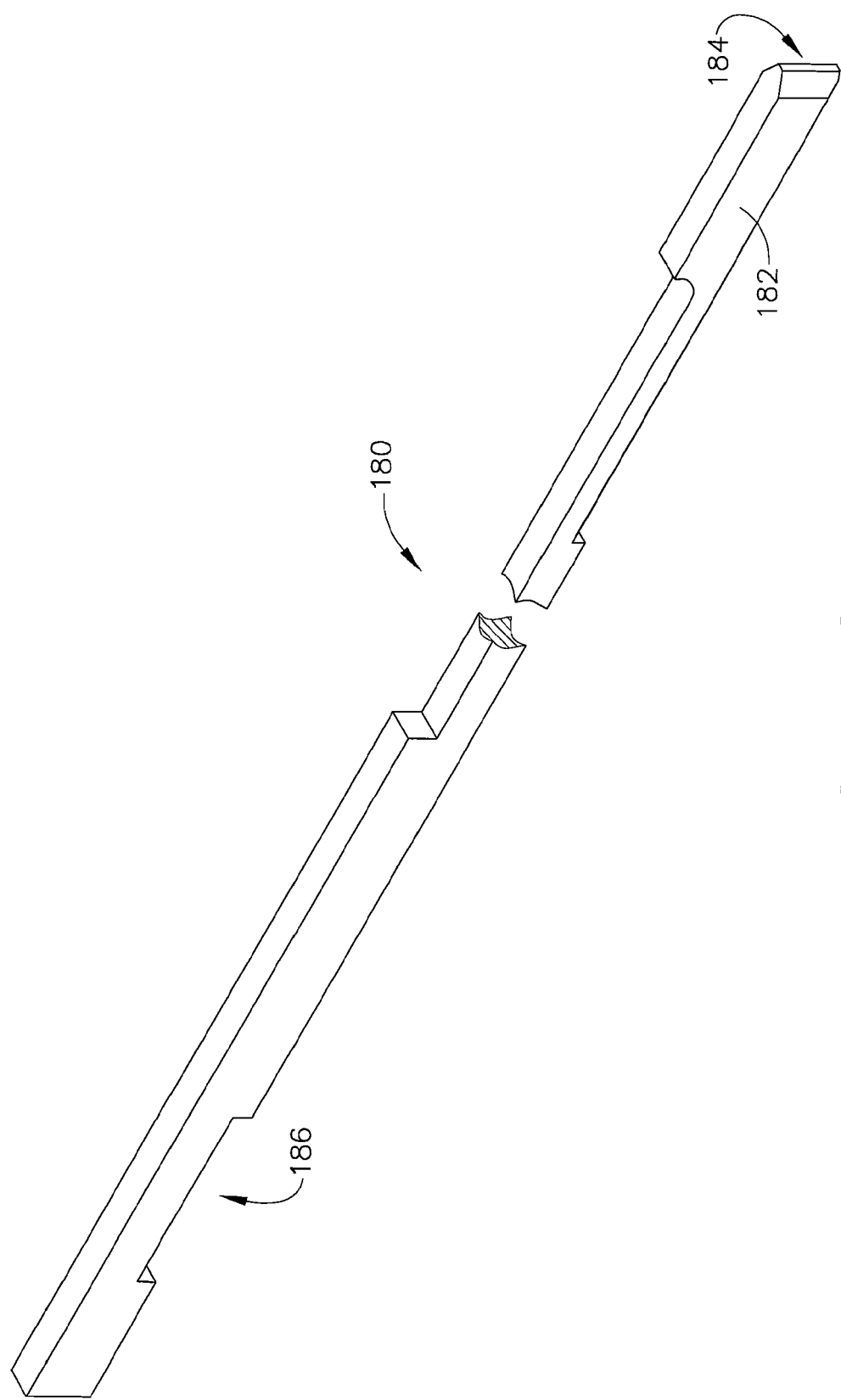
FIG. 15C is a fragmentary, isometric view of the anvil separator.

The proximal end of anvil body 160 is attached to the distal end of an anvil extension 170 by mounting anvil T-connector 162 about a pair of projections 172 on the extension. As shown in FIG. 7, anvil extension 170 extends beneath clamp extension 112 proximally from anvil 160 through the open end of housing 50. Anvil extension 170 is split along the longitudinal centerline of the extension, as indicated at 174, to accommodate an anvil separator 180. Separator 180 extends longitudinally within anvil extension split 174 substantially through the length of housing 50. As shown in greater detail in FIGS. 15A-15C, the distal end of separator 180 has an increased height, as indicated at 182, to enable the separator to extend from beneath anvil body 160 up into the gap between anvil arms 164. Distal separator end 182 includes an inwardly angled tip 184 to facilitate movement of the separator between the anvil arms 164 at the distal end of the anvil arm gap. The proximal end of separator 180 is also of increased height and includes a notch 186 for connecting the separator to a driver, as will be described in more detail below. During the deployment process, separator 180 is advanced and retracted to move the separator tip 184 from a position within the anvil arm gap to a position between anvil tines 166. As separator tip 184 advances between anvil tines 166, the separator pulls the tines apart against the inward bias of the anvil arms 164. The spreading anvil tines 166 apply an outward force 32 (shown in FIG. 1) to the staple legs 14, 16 of a staple held on the tines, expanding open the staple. Preferably, distal separator end 182 has a width sufficient to cause anvil tines 166 to be pulled apart a sufficient distance to bend staple legs 14, 16 back to an angle of approximately 180°, as shown in FIG. 2.

Figure 16:
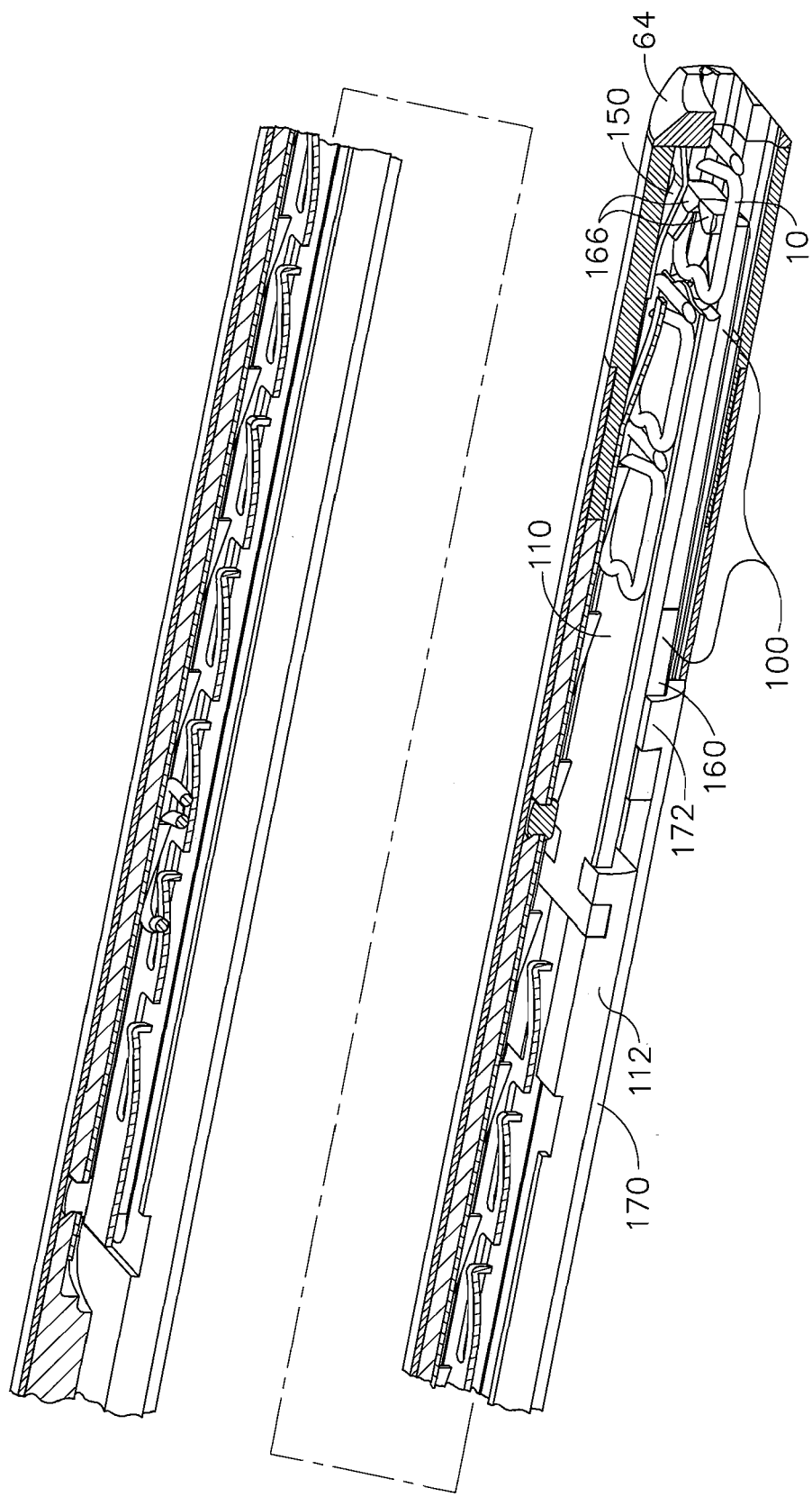
FIG. 16 is a fragmentary, isometric view, partially in section, of the distal end of the stapler shown in an initial deployment position.
Figure 17:
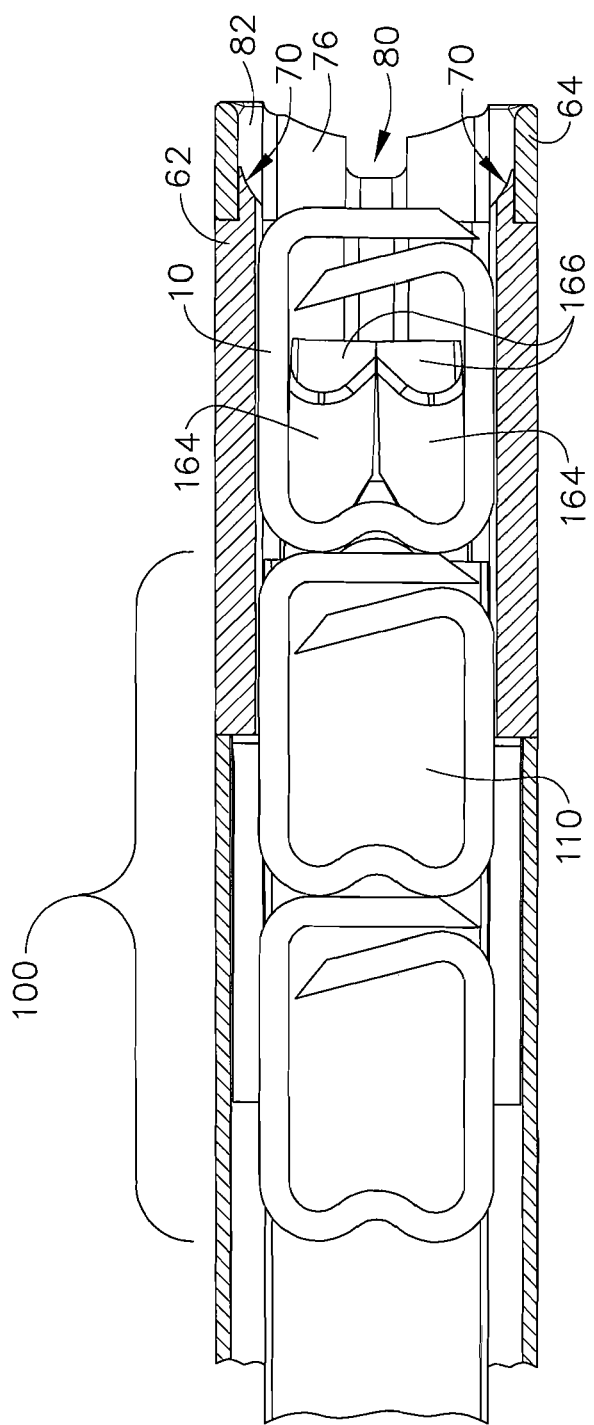
FIG. 17 is a top, partially sectional view of the distal stapler end with the staple guide and staple indexer removed, showing the initial deployment position.

As mentioned above, a shoe 150 flexibly extends from the distal end of staple indexer 134 for transferring staples from stack 100 into the staple discharge channel for deployment. Shoe 150 indexes one staple from stack 100 in the magazine channel into a staging position within the discharge channel during each deployment sequence. As shown in FIGS. 13A-13D, shoe 150 includes a pair of downwardly biased side rails 152. Side rails 152 are spaced apart a distance substantially equal to the width $w_i$ between staple legs 14, 16 in the pre-deployment staples 10. The proximal facing ends of side rails 152 are sloped to facilitate movement of a staple beneath the shoe 150. Once a staple is under the shoe, side rails 152 apply a downward force on the staple legs 14, 16. In an initial, pre-fire position shown in FIG. 16, shoe 150 is just distal of the staple stack 100, and above the individual staple 10 staged within the discharge channel. In this position, shoe side rails 152 push down onto legs 14, 16 of the staged staple to hold the staple in position. As shoe 150 pushes down on staple 10, anvil tines 166, which are in the initial, inwardly-biased position, extend up through the closed loop of the staple. FIG. 17 shows in greater detail a staged staple 10 held by anvil tines 166.

During the deployment process, clamp 110 moves distally through the discharge channel, advancing against the back span of staple 10, and pinning the staple between the clamp and anvil tines 166. As clamp 110 advances, the proximal end of shoe 150 is lifted up against the downward bias by the contact between the advancing clamp and the proximal sloped surfaces of side rails 152. As clamp 110 continues advancing, the distal most staple in stack 100 is pushed under shoe 150 by the force of the moving stack. As the staple moves underneath shoe 150, the shoe side rails 152 push the staple legs 14, 16 down onto clamp 110. The staple remains in this position, between shoe 150 and clamp 110, and against the proximal face of end cap 64, during the opening and forming of the previous staple. As the distal-most staple moves under shoe 150, the remaining staple stack 100 is indexed distally within the magazine channel due to the advancement of staple pusher 126 by clamp extension 112. When clamp 110 retracts following staple forming, shoe 150 pushes the staple downward into the discharge channel between the distal clamp face and retracting anvil tines 166, thereby staging the staple for the next deployment sequence. In the present invention, the staple deploying components within housing 50 are substantially the same size as the pre-deployment staples 10, in order to maximize the staple size and, thus, tissue purchase during deployment, while maintaining a small (3-5 mm) profile for the stapler. The distal deployment opening 52 in end cap 64 is sized to allow clamp 110, anvil tines 166, separator 180 and the deploying staple 10 to pass outside of the former during the deployment process, while the proximal face of the end cap serves as an end stop for staple stack 100.

Turning now to FIGS. 5, 18, 19 and 20, which show the proximal, handle end of stapler 40 in an initial deployment position. Handle 42 comprises a cover 190 formed in sections which are joined together during the manufacturing process by any of a number of suitable means known in the art. As mentioned above, a rotating knob 54 is connected at the distal end of handle cover 190 for rotation relative to the handle. Staple housing 50 extends proximally through knob 54 and into a former bushing 192. A plurality of flanges 194 (shown in FIG. 7) extend from the proximal end of the housing 50. Housing 50 is fixed within former bushing 192 by locking flanges 194 between the bushing end and a housing clamp screw 196. A former distal stop 200 and a former return spring 202 encircle housing 50 just distal of former bushing 192, between the bushing and knob 54.

Clamp extension 112 passes through the open proximal end of housing 50 and into a clamp bushing 204. The proximal end of clamp extension 112 is locked within the clamp bushing 204 by a connector 206. A clamp spring 212 encircles clamp extension 112 between clamp bushing 204 and housing clamp screw 196. Separator 180 and anvil extension 170 extend through clamp bushing 204 beyond the proximal end of clamp extension 112. Proximal of clamp bushing 204, notch 186 in separator 180 engages a similarly sized cutout in a separator driver 214 for attaching the separator to the driver. A separator spring 216 encircles anvil extension 170 and separator 180 between the clamp bushing 204 and separator driver 214 for biasing the separator driver into a proximal, retracted position. Separator spring 216 has a high spring constant relative to the other springs within handle 42 and can be loaded in the device in a partially compressed, preloaded configuration. This higher spring constant and/or preload keeps separator spring 216 from being compressed prior to clamp 110 and anvil 160 having reached distal end stops. After the anvil 160 and clamp 110 have reached distal-most positions, the compressing of separator spring 216 allows separator 180 to continue moving distal relative to anvil 160 and clamp 110 to spread the anvil tines 166. Anvil extension 170 extends proximally through the open end of housing 50, and beyond separator 180 and separator driver 214, to the proximal end of handle 42. An anvil bushing 220 is attached adjacent the proximal end of anvil extension 170 by one or more connectors 222 shown in FIG. 19. An anvil stop 224 is connected to anvil extension 170 proximal of anvil bushing 220 by a nut or other retention member 226. The diameter of anvil stop 224 is less than the inner diameter of anvil bushing 220 to allow the anvil stop to move within the bushing. An anvil spring 230 extends between anvil stop 224 and the distal end of anvil bushing 220 for biasing anvil stop 224 to a proximal position.

An anvil catch 240 is located beneath anvil stop 224 for holding anvil 160 in a forward position during a portion of the deployment process. Anvil catch 240 is pivotally connected between handle covers 190 by a pin 242. Pin 242 enables anvil catch 240 to pivot up and down within the handle 42. An anvil catch spring 244 biases the anvil catch 240 upward into contact with the anvil stop 224. The proximal end of anvil catch 240 extends out the open proximal end of handle cover 190 to allow for manual resetting of the catch. In the initial deployment position shown in FIGS. 18 and 20, anvil stop 224 is in a proximal-most position and a raised tip 248 on the upper surface of anvil catch 240 is biased into contact with the outer side surface of the anvil stop. In this position anvil stop 224 is free to move within handle 42, with the catch tip 248 riding along the outer surface of the stop.

A clamp catch 246 is located just distal of anvil catch 240 for holding clamp 110 in a distal position during the deployment process. Clamp catch 246 is pivotally connected between handle covers 190 by a pin 250. Pin 250 enables clamp catch 246 to pivot up and down within handle 42. A clamp catch spring 252 biases clamp catch 246 in the direction of clamp bushing 204. In the initial deployment position shown in FIGS. 18 and 20, clamp catch 246 is biased up against the outer side surface of clamp bushing 204. Anvil catch 240 and clamp catch 246 each include radially outward extending detents, identified by numerals 254 and 256 respectively. The detents 254, 256 on the two catches extend towards each other into the space between the catches. Detents 254, 256 are sized and spaced to make contact when anvil catch 240 pivots about pin 242 following a manual resetting of the catch. The spacing between the detents 254, 256 produces a time delay between the retraction of anvil 160 and the retraction of clamp 110 during the deployment process. This time delay enables the anvil tines 166 to retract back ahead of the clamp 110 following staple release, to close the gap between the anvil tines and distal clamp face.

Figure 5:
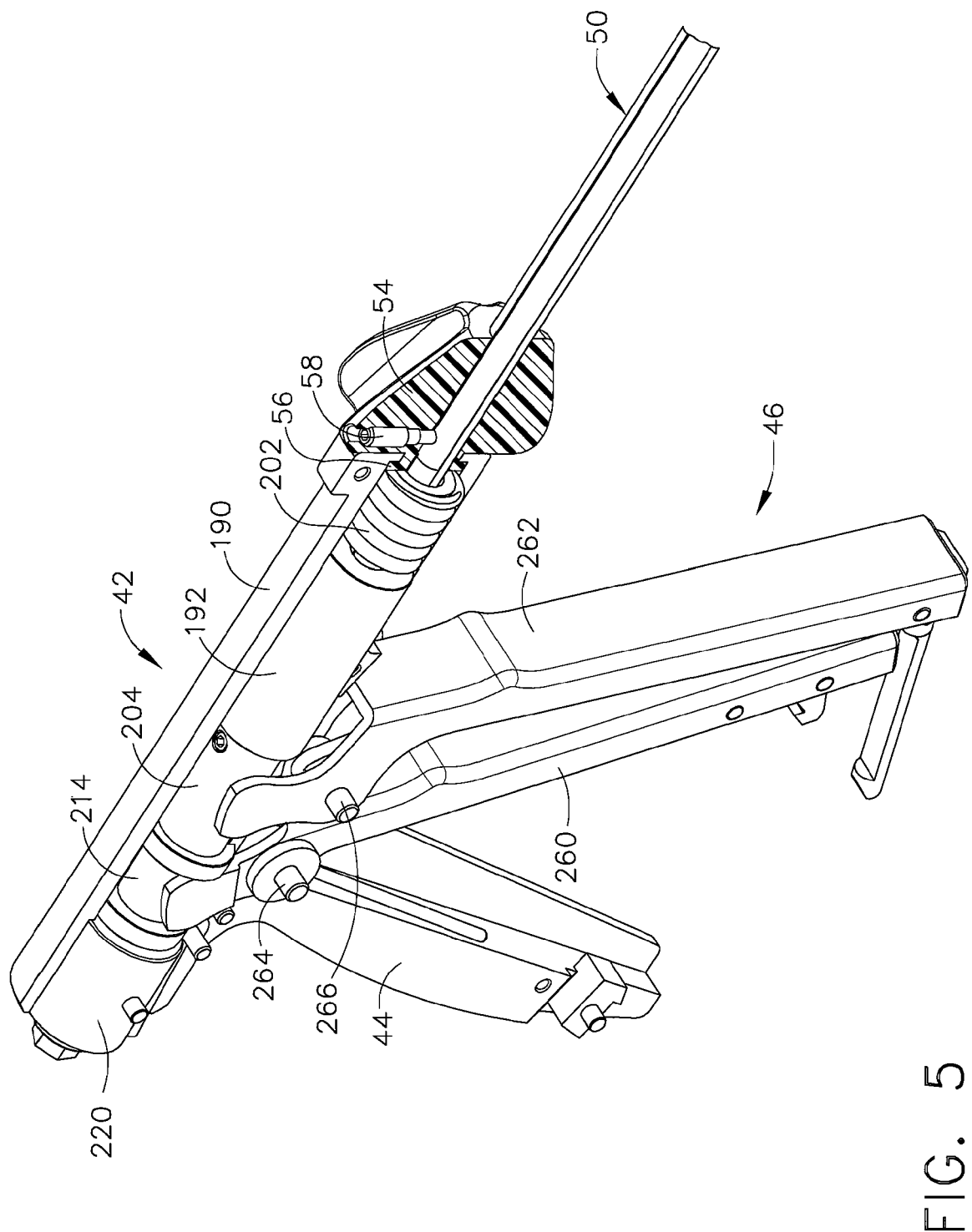
FIG. 5 is an isometric view of the proximal end of the surgical stapler of FIG. 4, shown with the handle cover partially removed.
Figure 18:
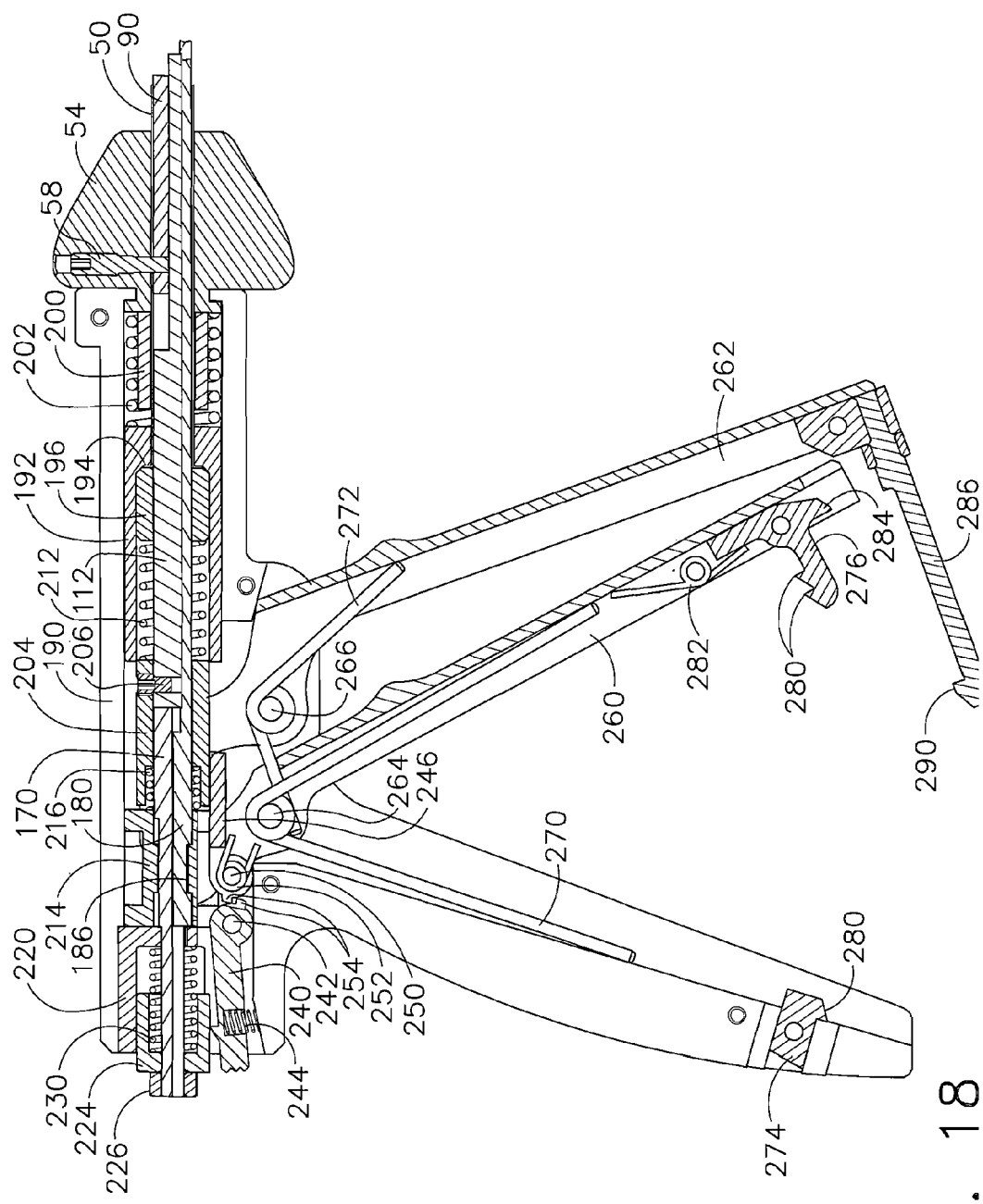
FIG. 18 is a side sectional view of the proximal end of the stapler in an initial deployment condition.
Figure 19:
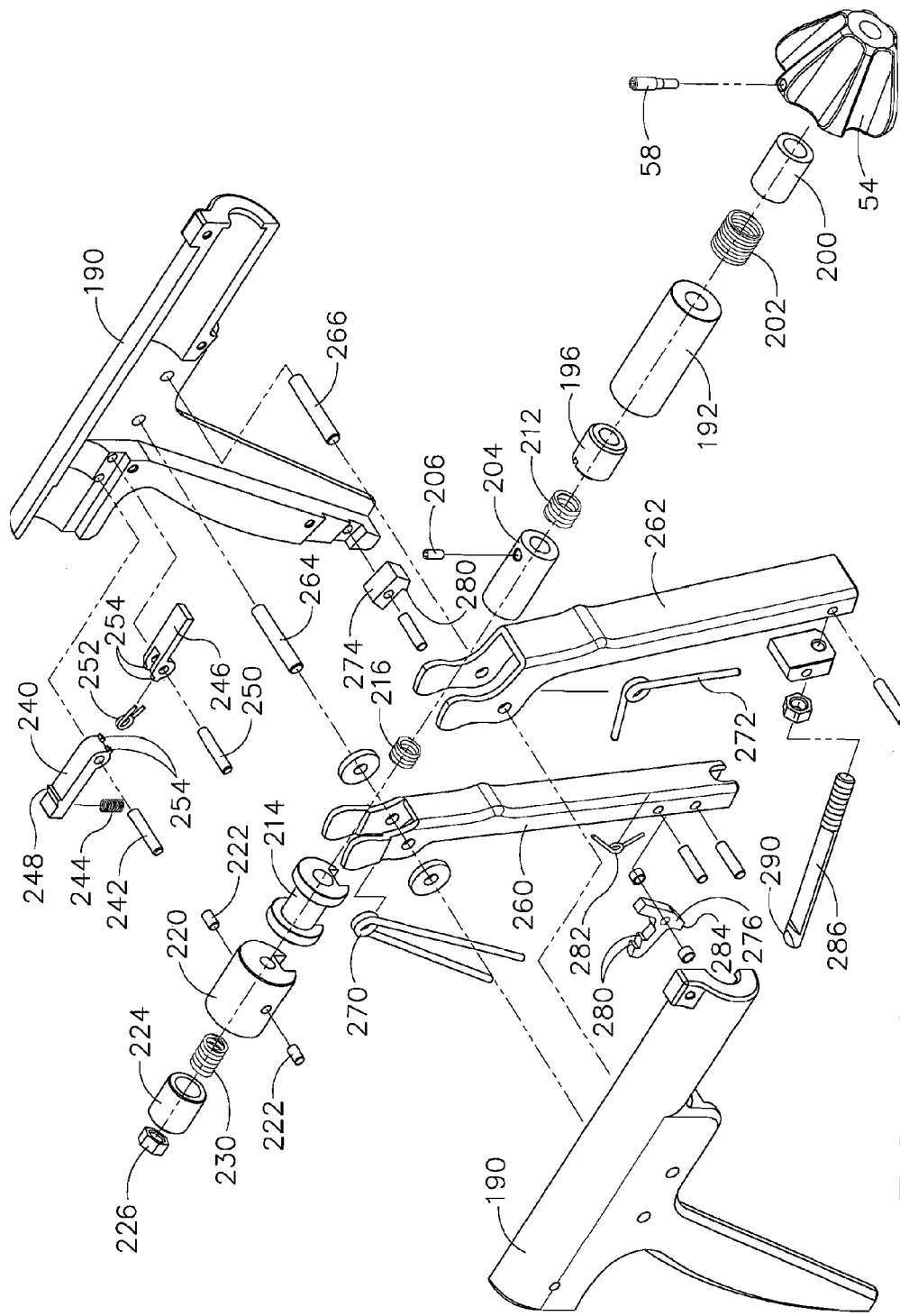
FIG. 19 is an exploded, isometric view of the stapler handle components.
Figure 20:
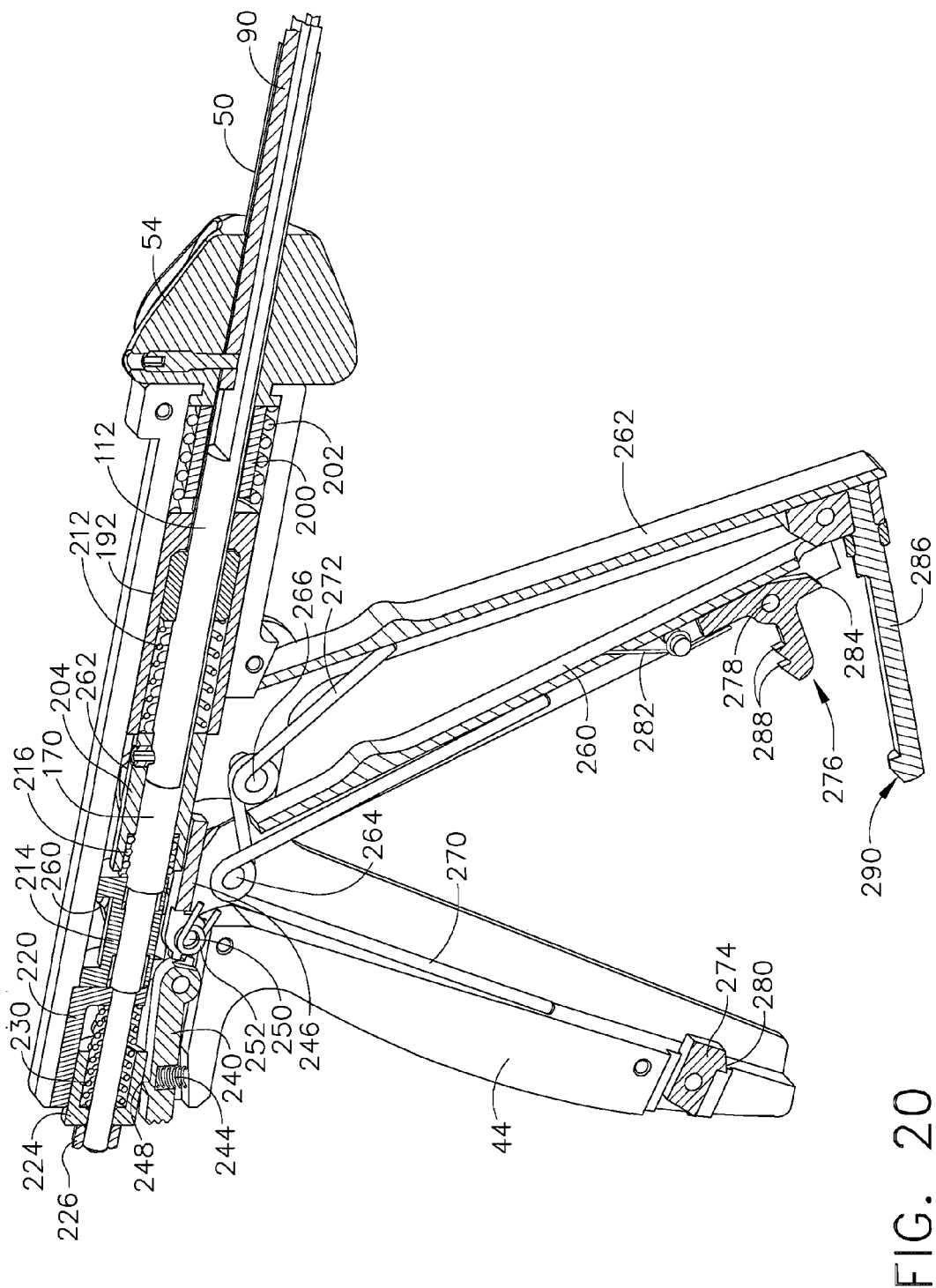
FIG. 20 is an isometric, sectional view of the proximal end of the stapler in an initial deployment condition.

As shown in FIG. 5, actuator assembly 46 includes an initial, separator trigger 260 and a secondary, former trigger 262. Separator and former triggers 260, 262 are comprised of channel-shaped frames that open proximally. The upper lobes of separator trigger 260 and former trigger 262 are rounded and extend up into handle cover 190. The upper lobes of separator trigger 260 are positioned along the sides of separator driver 214, in an opening between the proximal and distal ends of the driver. The upper lobes of former trigger 262 extend on opposite sides of clamp bushing 204, and are proximally spaced from, but aligned to make contact with, the proximal end of former bushing 192 when the trigger grip is pivoted towards pistol grip 44. Pivot pins 264, 266 extend between the sides of handle cover 190 and separately through the separator and former triggers 260, 262 to connect the actuator assembly to the handle. Separator trigger 260 pivots about pin 264, while former trigger 262 pivots about pin 266, in order to separately rotate the triggers relative to handle 42. As shown in FIGS. 18-20, pivot pin 264 also extends through a midsection of a separator leaf spring 270 to attach the spring to the separator trigger 260. The arms of separator leaf spring 270 extend between the inner channel of separator trigger 260 and pistol grip 44, so that the spring compresses as the separator trigger is squeezed closed. A second, former leaf spring 272 is connected about former trigger pivot pin 266. The arms of former leaf spring 272 extend between the inner channel of former trigger 262 and separator trigger 260. Former leaf spring 272 compresses as former trigger 262 is squeezed closed. The compression forces in separator and former leaf springs 270 and 272 return the separator and former triggers 260, 262 to the initial, open condition shown in FIGS. 18 and 20 when squeezing forces on the triggers are released.

A trigger latch 274 is affixed near the end of pistol grip 44, while a pawl 276 is attached near the lower end of separator trigger 260. Pawl 276 is pivotally attached to the separator trigger 260 by a pin 278. Latch 274 and pawl 276 include one or more teeth 280, 288 respectively on adjoining inner sides, which are drawn together as the separator trigger 260 is pulled towards pistol grip 44. Teeth 280, 288 on the latch and pawl interlock as separator trigger 260 reaches a fully squeezed condition. A pawl spring 282 is attached inside separator trigger 260, in contact with pawl 276, to bias the pawl into a position for engaging latch 274. Pawl 276 includes a downwardly extending tip 284. A trigger release 286 is attached to the lower end of former trigger 262 to extend back proximally from the trigger. The proximal end of trigger release 286 includes a raised release head 290 pointed in the direction of pawl tip 284. Trigger release 286 is attached to former trigger 262 at a position to allow the release head 290 to contact pawl tip 284 as the former trigger pivots past the latched separator trigger 260 during the deployment process. Pawl tip 284 and release head 290 are angled to allow the trigger release 286 to flex and pass proximally beneath the pawl tip as former trigger 262 is being squeezed closed, but to make driving contact with the pawl as the former trigger pivots back open after the squeezing force is stopped. The contact between the retracting release head 290 and pawl tip 284 rotates pawl 276 about connecting pin 278 against the bias of pawl spring 282. As pawl 276 rotates, pawl teeth 288 disengage from latch teeth 280, separating the pawl from latch 274, and allowing separator trigger 260 to pivot back under the force of separator leaf spring 270 to a fully open position.

To deploy a staple 10, stapler 40 is inserted through a small diameter port or flexible endoscopic platform to reach the desired tissue area inside a body cavity. At the appropriate tissue location, stapler end 52 is placed adjacent the tissue or tissue fold to be stapled, with rotating knob 54 being turned as necessary to position the staple prongs 26. When stapler 40 is appropriately aligned, separator trigger 260 is manually squeezed in the direction of pistol grip 44 to initiate staple deployment. In the initial deployment position shown in FIGS. 18 and 20, the upper lobes of separator trigger 260 contact the distal end of separator driver 214, while the upper lobes of former trigger 262 are spaced proximally from former bushing 192. Housing 50 and the attached staple former are in a proximal, retracted position, with the staged staple 10 located within former body channel 66, just proximal of the former end cap channel 76, as shown in FIGS. 17, 21 and 22. Side rails 152 on shoe 150 push down on the staged staple in the discharge channel, while the next staple in stack 100 is held between holding arm 144 and the upper surface of clamp 110. Within the discharge channel, clamp 110 is in a proximal-most position with the distal clamp face adjacent back span 12 of the staged staple. Anvil 160 is retracted back within the former body 62, with anvil tines 166 drawn inward and up through the loop of the staged staple. Separator 180 is also in a proximal-most position with separator tip 184 retracted back inside the gap between anvil arms 164.

Figure 23:
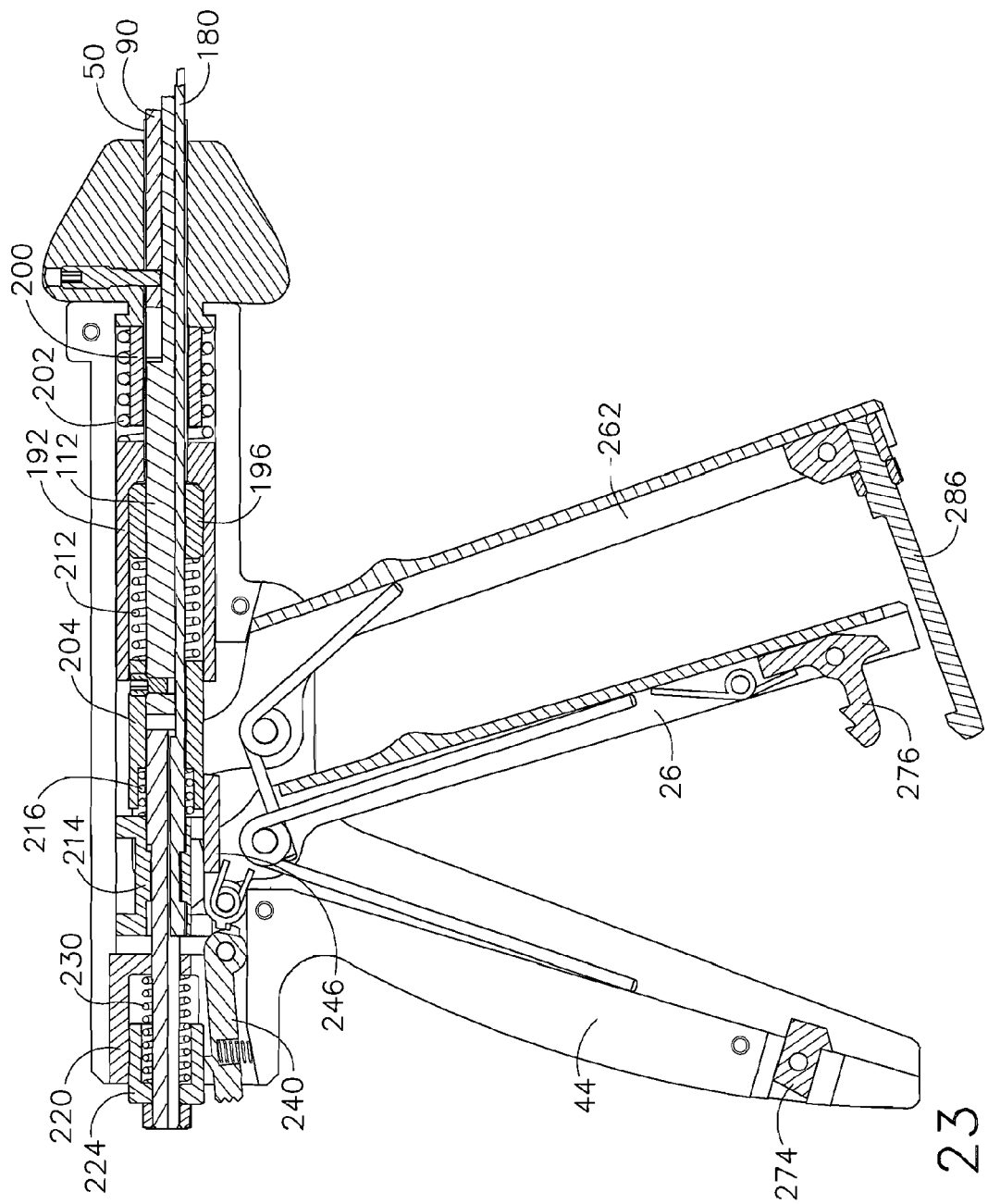
FIG. 23 is a side sectional view of the proximal end of the stapler, shown with the separator driver moved distally to advance the separator and clamp.
Figure 24:
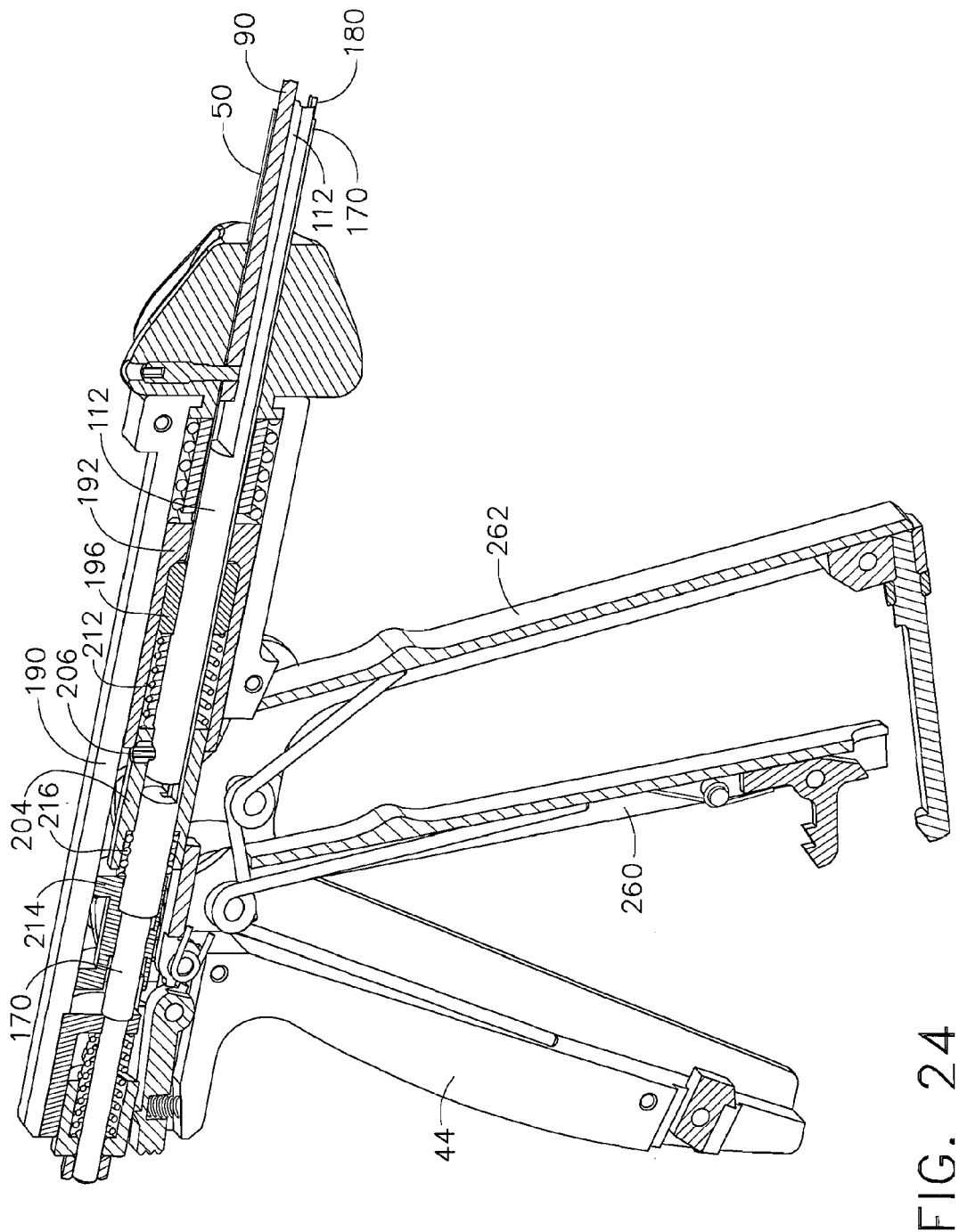
FIG. 24 is an isometric, sectional view of the proximal end of the stapler, similar to FIG. 23, showing the separator driver moved distally to advance the separator and clamp.
Figure 25:
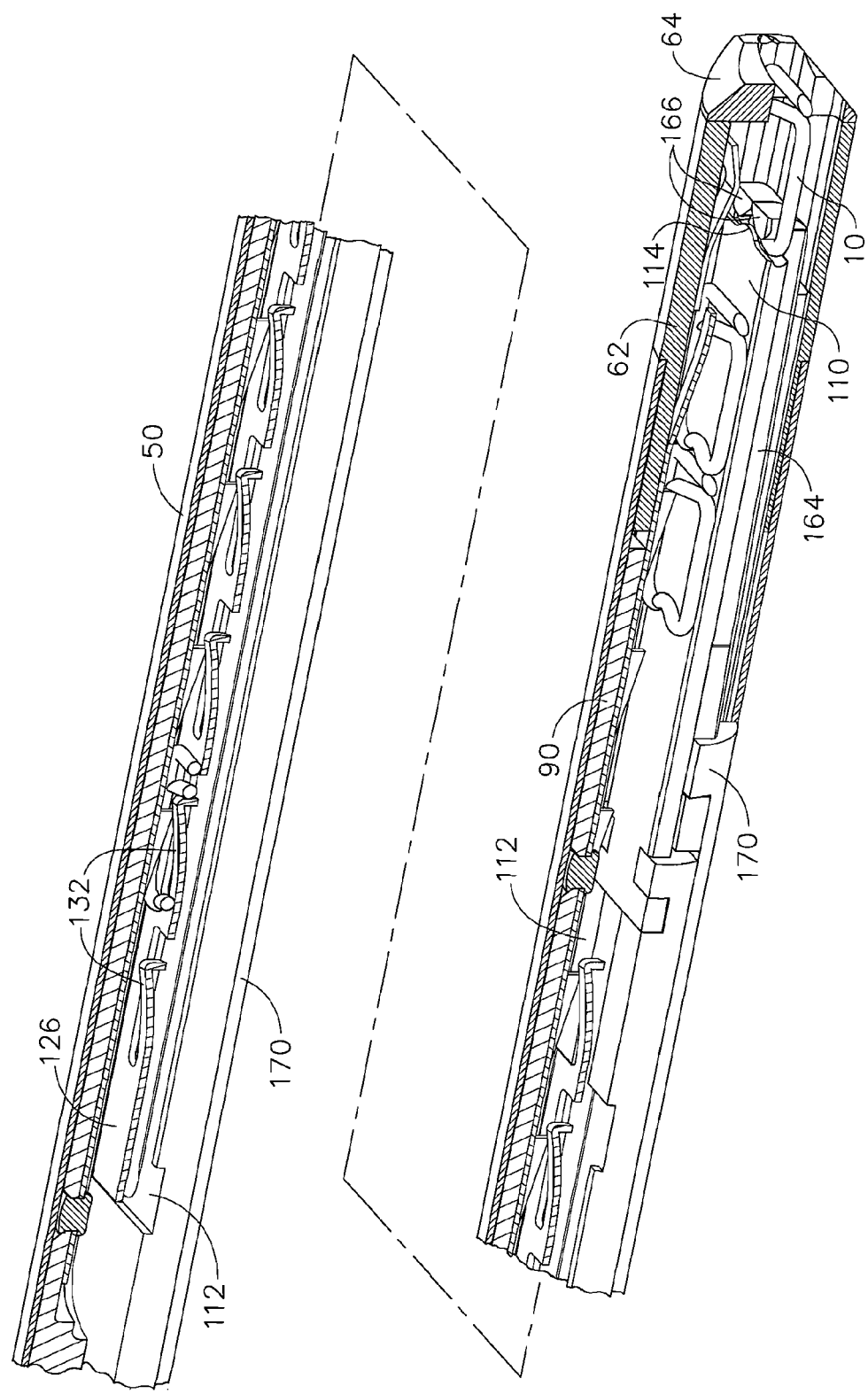
FIG. 25 is an isometric, partial sectional view of the distal end of the stapler showing the clamp and staple advanced distally against the anvil.
Figure 28:
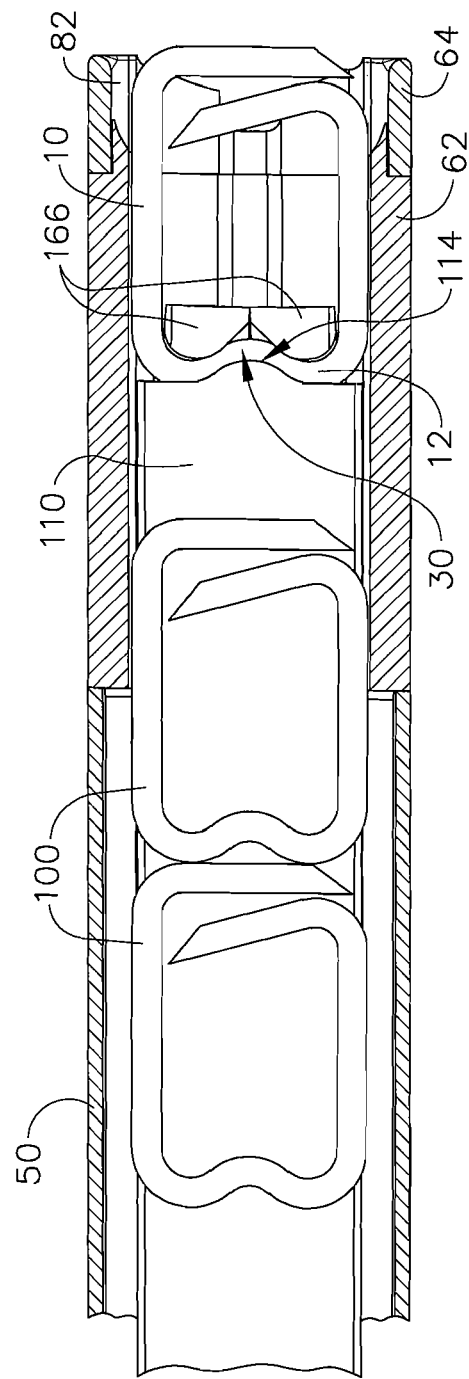
FIG. 28 is a top, partially sectional view of the distal stapler end with the staple guide and staple indexer removed, depicting a similar deployment stage as FIG. 26.

As spreader trigger 260 is squeezed to begin deploying a staple, the trigger pivots about pin 264 causing the upper trigger lobes to push against separator driver 214, moving the driver distally within handle 42, as shown in FIGS. 23 and 24. As separator driver 214 moves, the driver pushes separator 180 distally due to the stepped connection between the driver and separator notch 186. The distal movement of separator driver 214 also applies a force against separator spring 216, which due to the stiff nature of the spring, transfers the force to the proximal end of clamp bushing 204, thereby driving the bushing and attached clamp extension 112 forward. Staple pusher 126, seated within clamp extension 112, also moves distally as separator trigger 260 is squeezed; causing the pusher arms 132 to drive the individual staples in stack 100 (only one is shown in FIG. 25) towards the distal stapler end 52. As clamp extension 112 moves clamp 110 forward within the discharge channel, the gap between the distal clamp face and anvil tines 166 is reduced, drawing the staged staple 10 against the proximal, rounded face of the anvil tines, as shown in FIGS. 25 through 27. As clamp 110 moves staple 10 against anvil tines 166, the staple back span 12 lodges within the inward radius 116 of the distal clamp face, and arcuate projection 114 on the clamp face engages radial depression 30, as shown in FIG. 28.

Figure 29:
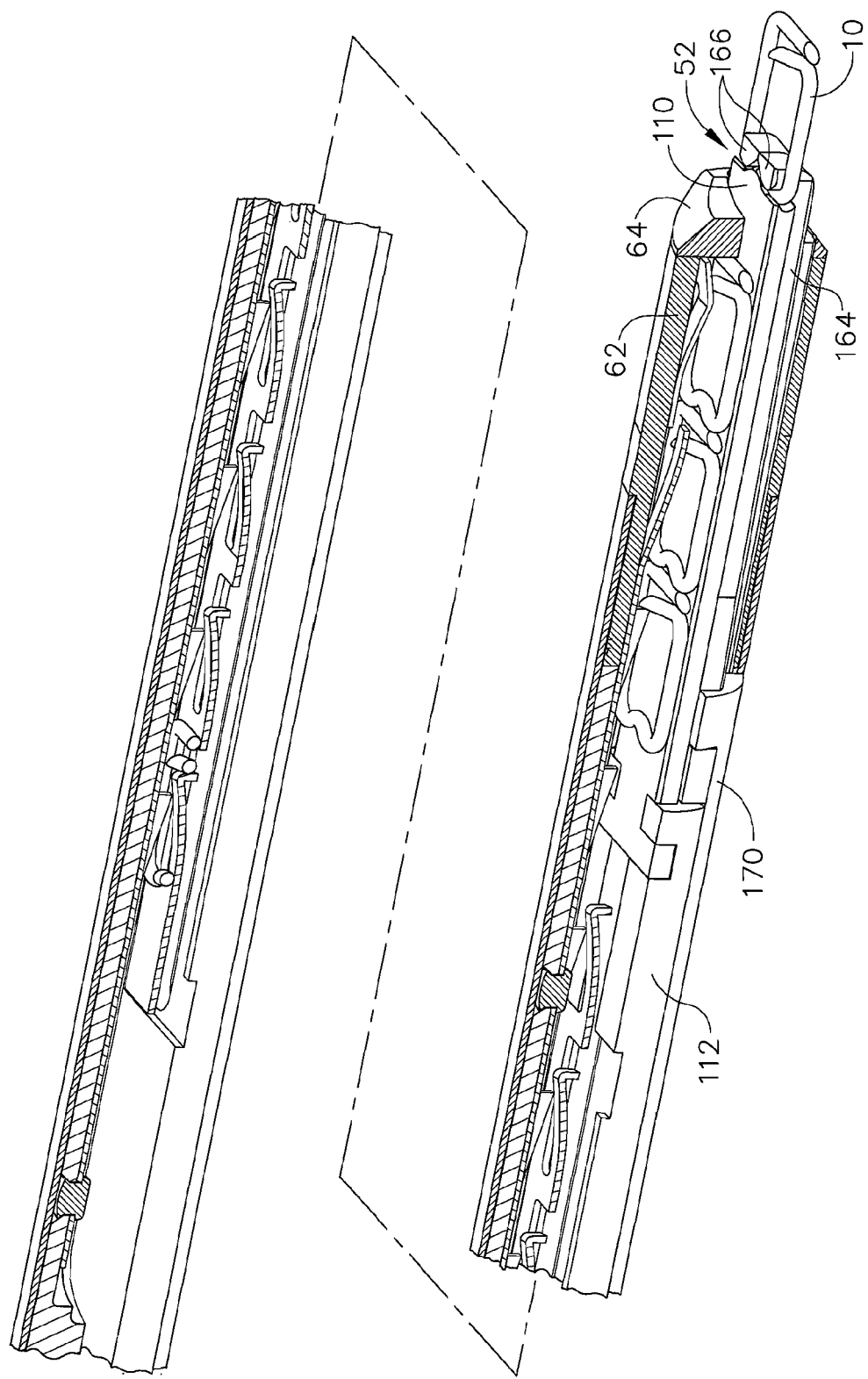
FIG. 29 is an isometric, fragmentary view of the distal end of the stapler showing a staple held by the clamp and anvil tines in a fully advanced position outside the open stapler end.
Figure 32:
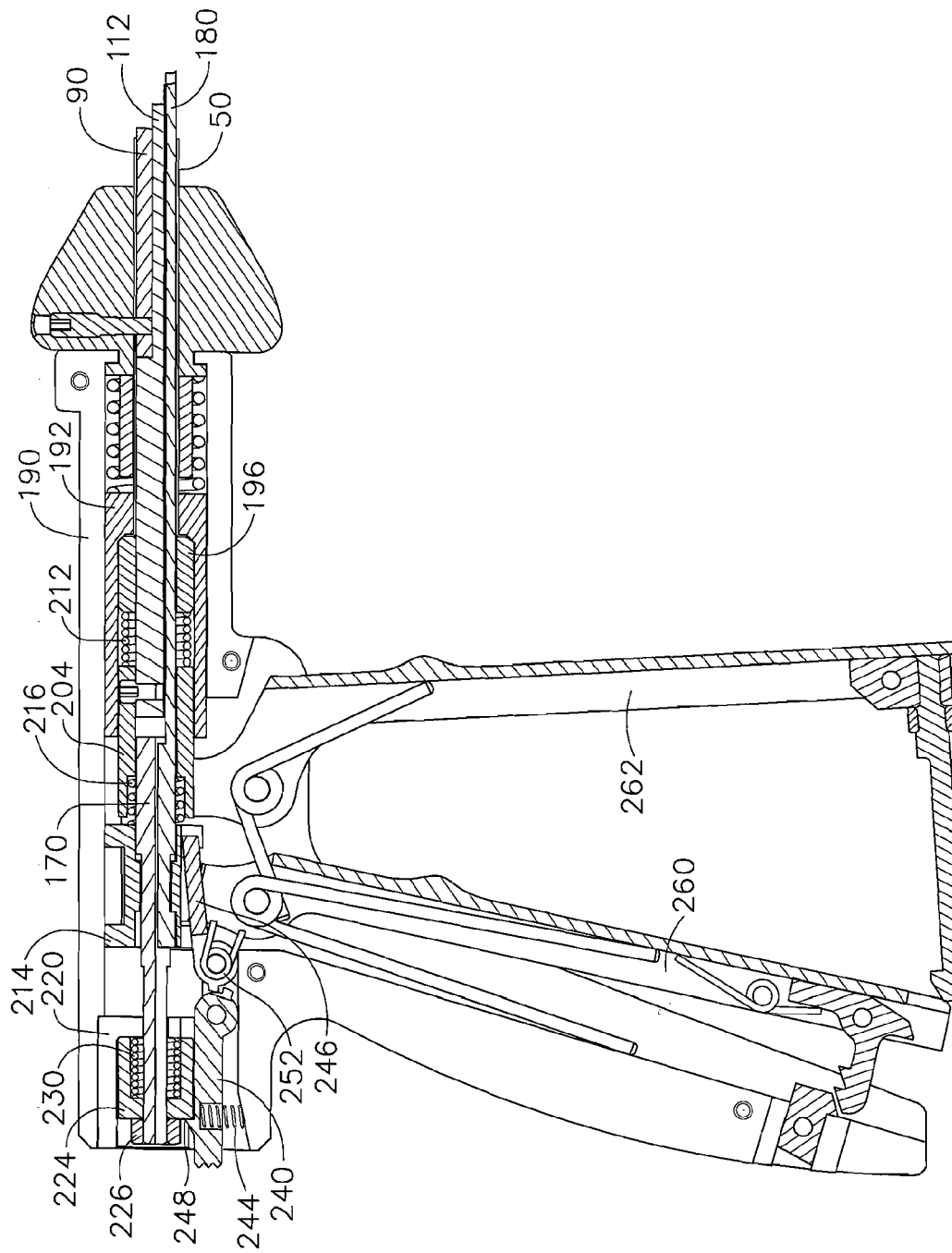
FIG. 32 is a side sectional view of the proximal end of the stapler showing the distal end stops for the anvil and clamp, and the separator trigger driving the anvil separator further distally.
Figure 33:
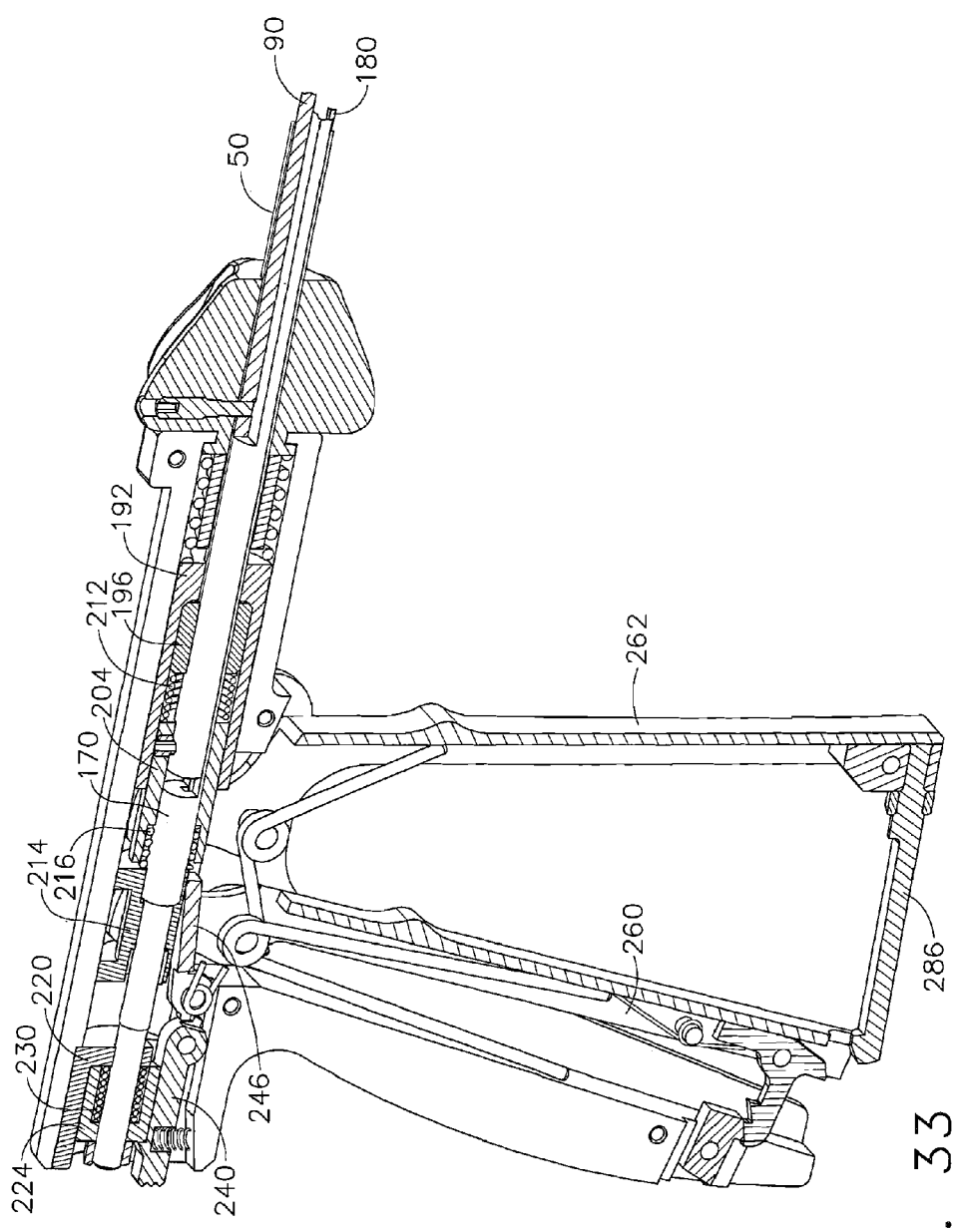
FIG. 33 is an isometric, sectional view of the proximal end of the stapler showing the same deployment stage as FIG. 32.
Figure 34:
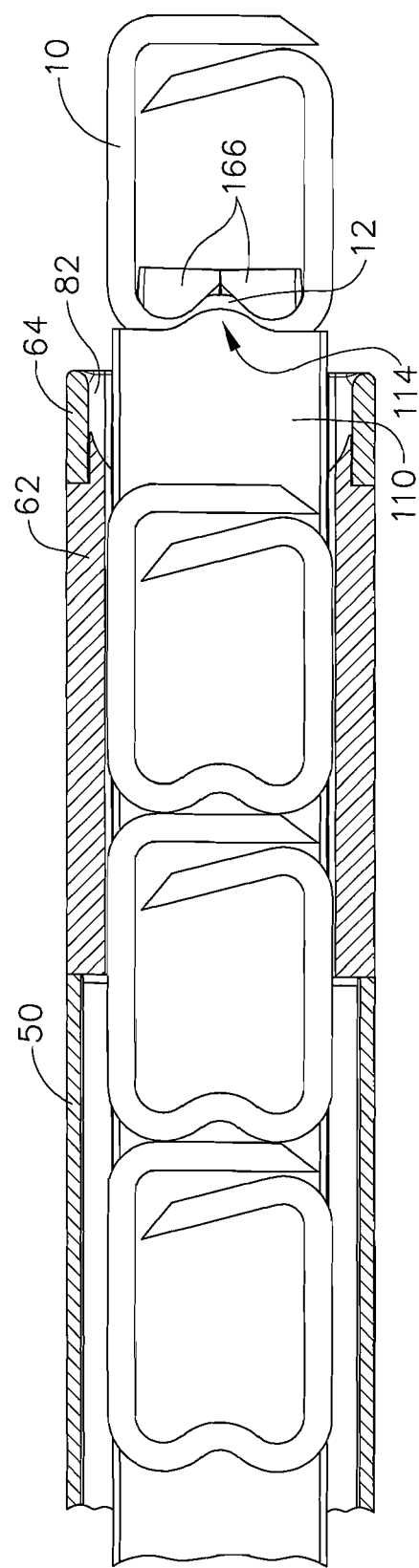
FIG. 34 is a top, partially sectional view of the distal stapler end showing a staple held outside the stapler by the anvil and clamp during an intermediate stage in the deployment process.
Figure 35:
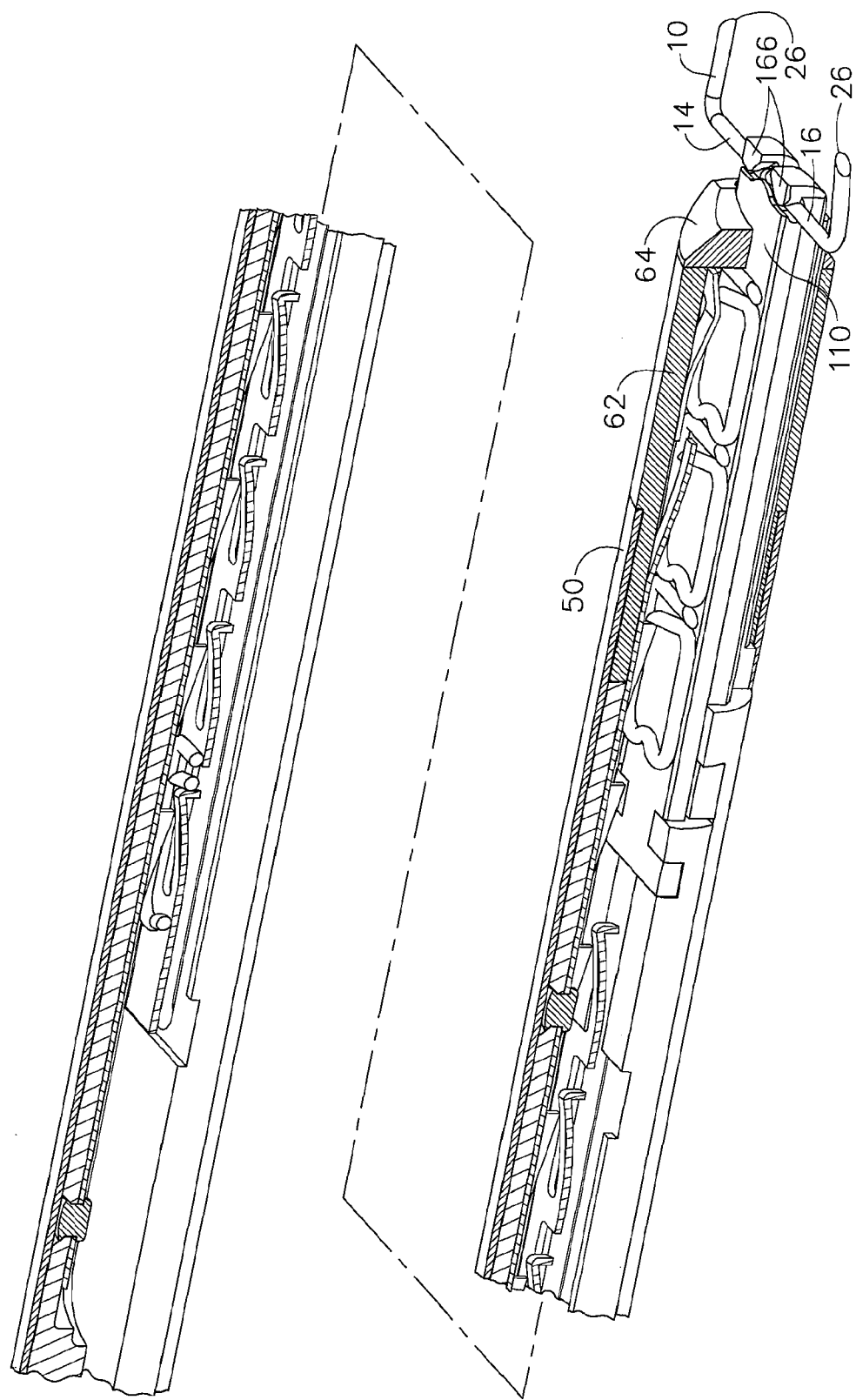
FIG. 35 is an isometric, fragmentary, partially sectional view of the distal end of the stapler showing a staple expanded open by the anvil and separator outside the open stapler end.
Figure 38:
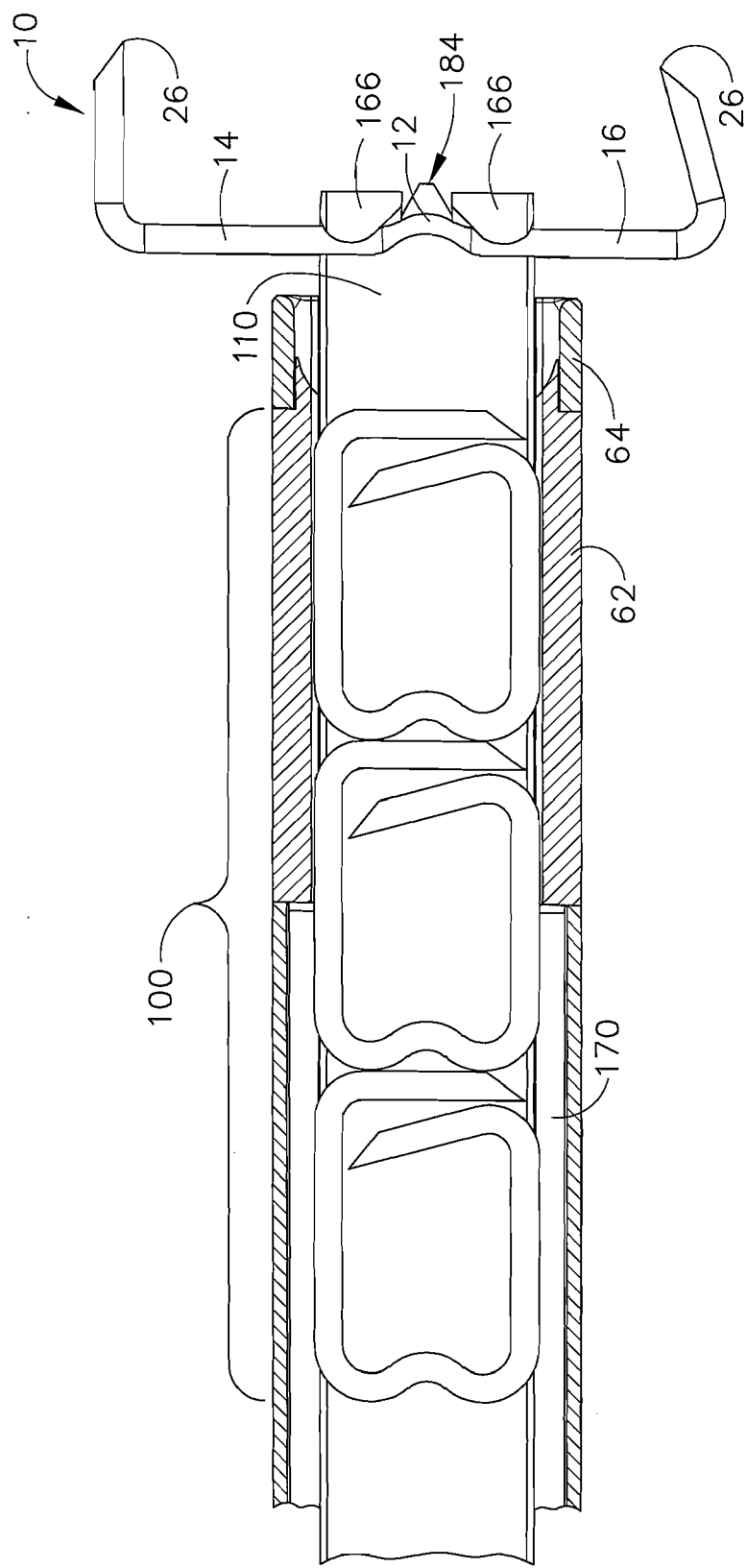
FIG. 38 is a top, partially sectional view of the distal stapler end showing a staple expanded open outside the open stapler end.

With staple 10 pinned between clamp 110 and anvil tines 166, the continued force of trigger 260 on separator driver 214 advances separator 180 and clamp 110 further distally; pushing the previously stationary staged staple 10 and anvil tines 166 through the former channels 66 and 76, and out the distal end of former end cap 64, as shown in FIGS. 29-31. As anvil 160 is pushed distally, inside handle 42 the moving anvil extension 170 pulls anvil stop 224 distally within anvil bushing 220, against the counter force of anvil spring 230, as shown in FIGS. 32 and 33. When anvil stop 224 abuts against the distal end of anvil bushing 220, the contact between the anvil bushing and anvil stop prevents further distal movement of anvil tines 166, as well as clamp 110 and staple stack 100 within the discharge channel. At this position, clamp 110 has pushed the staged staple 10 and anvil tines 166 fully out of the open stapler end 52 as shown in FIG. 34. As anvil stop 224 reaches the distal end stop inside anvil bushing 220, the proximal end of the anvil stop moves distally past tip 248 on anvil catch 240, allowing the catch to pivot up into contact with the proximal end of the anvil stop under the force of catch spring 244. The contact between anvil catch tip 248 and anvil stop 224 holds anvil 160 in an advanced position, with tines 166 outside the open stapler end 52, and prevents the anvil from retracting proximally during staple formation and release. Likewise, as clamp bushing 204 moves beyond the distal end of clamp catch 246, the clamp catch pivots up into the clamp bushing path under the force of clamp catch spring 252.

With anvil 160 and clamp 110 stopped from further distal movement, continued squeezing on separator trigger 260 pushes separator driver 214 further distally within handle 42. As separator driver 214 advances, the driver forces separator spring 216 to compress against the now stationary clamp bushing 204. Prior to this point, separator spring 216 has had little or no deformation due to the higher spring constant and/or preload of the separator spring as compared to the other springs in the system. The additional force on separator trigger 260 continues the distal advancement of separator 180 relative to the stationary anvil 160, staple 10 and clamp 110. This additional movement allows separator tip 184 to move distally beyond the anvil gap and between the ends of anvil arms 164. The angle of separator tip 184, as well as the inward angle of the anvil arms 164, facilitates movement of the separator tip between the arms outside the open end 52 of the former. During the separator trigger stroke, separator end 182 moves through the anvil arm gap and former recesses 72, 80 to reach the open stapler end 52.

As separator tip 184 moves between anvil arms 164, the arms are driven apart, causing anvil tines 166 to apply an outward spreading force to staple legs 14, 16. This outward spreading force on the staple legs 14 16 is indicated by arrows 32 in FIG. 1. The force against staple legs 14, 16 pulls the staple 10 to an open condition. As staple 10 expands open from its initial, closed-form shape, prong tips 26 move from an inward, overlapping position to the open, spread position described above, producing an increased width dimension in the staple. The substantial increase in width between the closed, folded staple condition and the open, expanded staple condition enables the staple to obtain a substantial tissue purchase while utilizing a small diameter delivery shaft. With staple prongs 26 facing in a substantially forward direction, staple legs 14, 16 define an approximately 180° angle, in alignment with the staple back span 12, as shown in FIGS. 35-38. A lesser opening angle may be achieved if desired by controlling the lateral spread of the anvil arms 164. This may be achieved, for instance, by reducing the width of separator tip 184.

Figure 39:
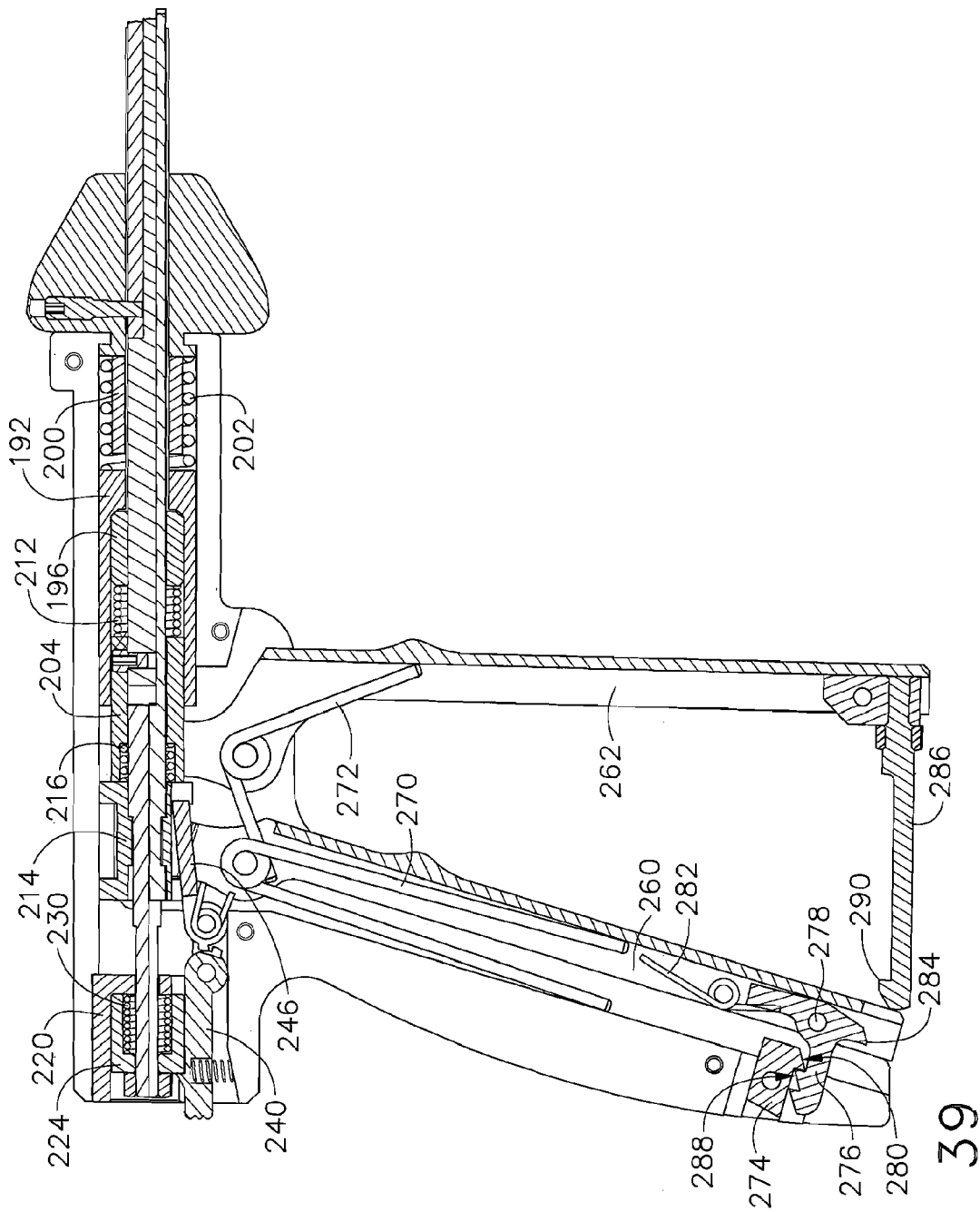
FIG. 39 is a side, sectional view of the proximal stapler end showing the separator trigger fully actuated to the distal end stops for the separator, anvil and clamp.
Figure 40:
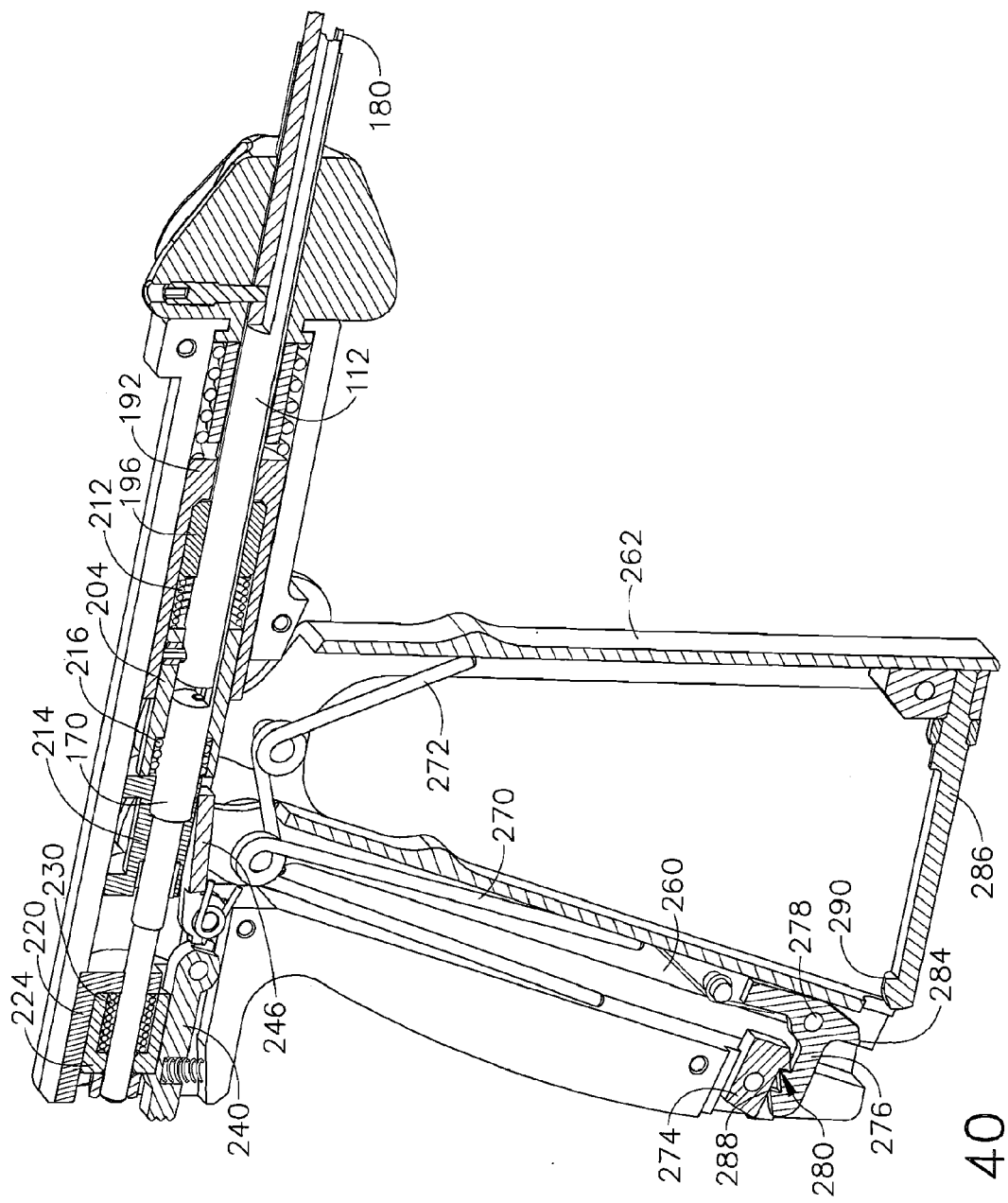
FIG. 40 is an isometric, sectional view of the proximal end of the stapler showing the same deployment stage as FIG. 39.

Separator 180 reaches a distal-most position, spreading anvil tines 166 and opening staple 10, as separator driver 214 bottoms out against the proximal end of clamp bushing 204, as shown in FIGS. 39-40. As separator driver 214 bottoms out, trigger 260 pivots to a fully closed position, in which pawl 276 rides beneath trigger latch 274. With pawl 276 beneath latch 274, pawl spring 282 urges the proximal pawl end upward to engage the pawl and latch teeth 280, 288. With pawl 276 held against latch 274 by teeth 280, 288, separator trigger 260 is locked in the fully pivoted position, to hold clamp 110, anvil 160 and the open staple 10 outside of stapler end 52. The engagement of trigger pawl 276 with pistol grip latch 274 provides a pause in the deployment process, allowing pressure on the actuator assembly to be relaxed. Pausing stapler 40 in this condition enables the surgeon to manipulate the open, exposed staple 10 relative to the surrounding tissue or material to insert the prongs 26 at the desired locations. Exemplary methods for manipulating tissue are described in U.S. patent application Ser. No. 12/359,351 which was previously incorporated by reference into this application. The movement of pawl 276 against latch 274 can produce audible as well as tactile feedback informing the surgeon that the staple is expanded and ready for tissue insertion. Additional tactile feedback is also provided through contact between pistol grip 44 and separator trigger 260.

Up to this point in the deployment process, the staple deploying assembly has been actuated solely through the squeezing of separator trigger 260. Secondary (former) trigger 262 has remained in its initial position, holding housing 50 stationary along the longitudinal stapler axis, with pin 58 at the distal end of housing slot 60. After the prongs 26 of the expanded staple 10 have been inserted at the desired tissue locations, the staple is formed through the tissue by applying squeezing pressure to former trigger 262. The pressure on former trigger 262 pushes the trigger lobes against former bushing 192, driving the bushing forward and compressing former return spring 202. As former bushing 192 moves distally, housing 50 also moves, sliding pin 58 through housing slot 60, due to the locking of the proximal housing end between the bushing and housing clamp screw 196. Housing 50 moves former end cap 64 distally, drawing end cap grooves 82 against the expanded staple legs 14, 16. The expanded staple is held fixed relative to the moving former end cap 64 by clamp 110 and anvil tines 166. The distal pushing force of end cap 64 against the expanded staple legs 14, 16 forces the legs to bend forward about the fixed anvil tines 166, drawing the bending legs into end cap grooves 82.

It will be appreciated that the points at which staple legs 14, 16 bend in response to the force of former end cap 64 are spaced laterally outward of the prior bending points for expanding open the staple, resulting in additional work hardening along the back span of the formed staple. The additional work hardening increases the strength of the formed staple. The distance between the inner surfaces of former grooves 82 is slightly less than the combined width of the expanded anvil tines 166 and staple legs 14, 16, to produce an interference fit between the former grooves and staple legs as the former rides along the outside edges of the staple. The interference fit between former grooves 82 and staple legs 14, 16 initially causes an inward overbending of the staple. The overbending of the staple during formation will typically be less than 10°, but is dependent on the materials characteristics of the staple. As former end cap 64 retracts following staple formation, the staple springs back to a closed, substantially rectangular configuration in which the staple legs are again substantially parallel. The interference fit between the former and staple legs thus "stretches" staple 10 as the stapler is being closed, to produce a substantially rectangular, finished shape. In metal forming, there are numerous methods to create a 90° bend in a piece of sheet metal. Examples and benefits are described in "Forming a 90 deg. Bend," *MetalForming Magazine*, August 1991, pp. 59-60, and "Fractures in Metal Stampings," *MetalForming Magazine*, November 1996, pp. 84-85, which are hereby incorporated herein by reference in their entirety. Techniques from this field may be applied in a novel way in the field of staple formation.

Figure 41:
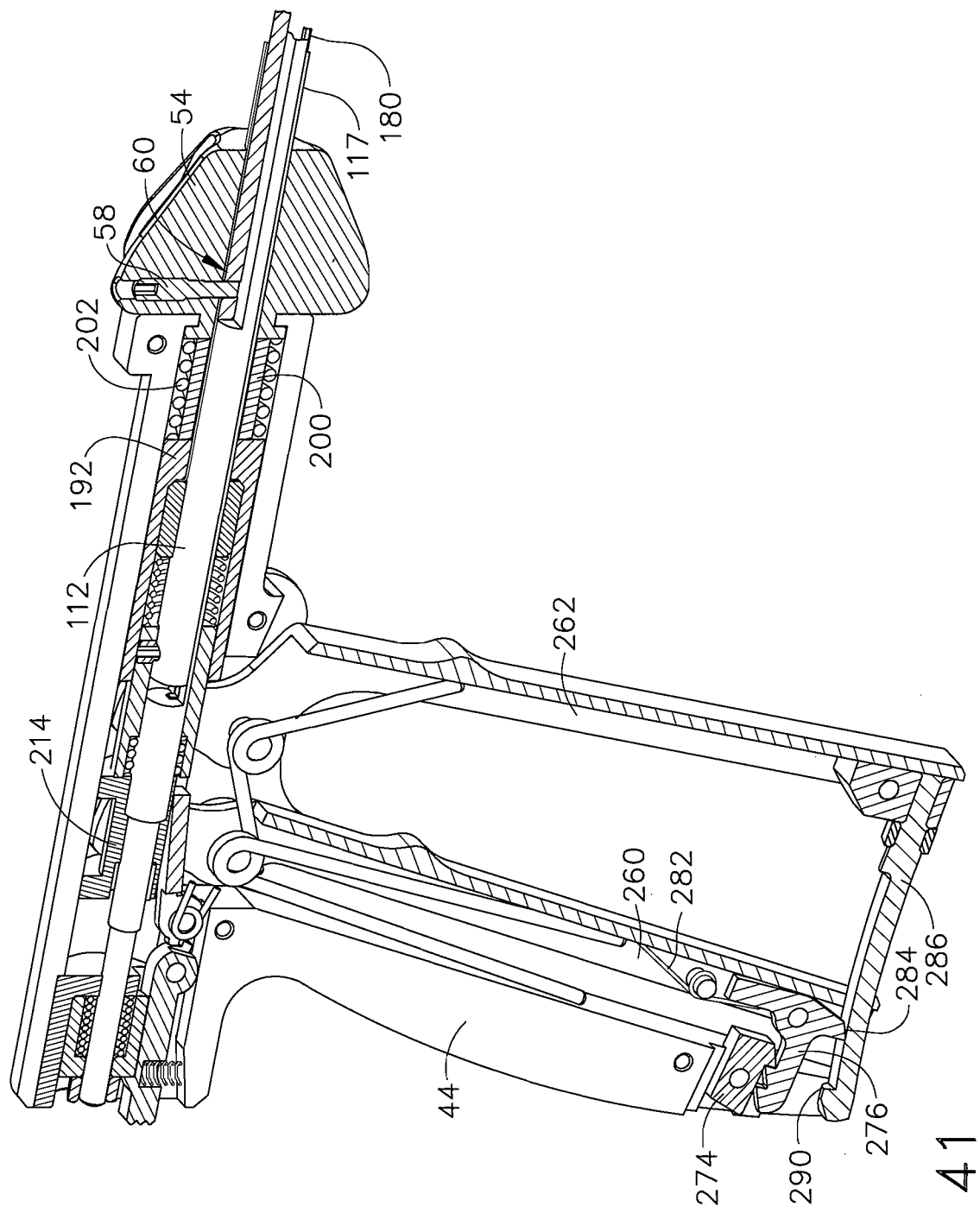
FIG. 41 is an isometric, sectional view of the proximal end of the stapler showing the separator and former triggers in fully pivoted positions.
Figure 42:
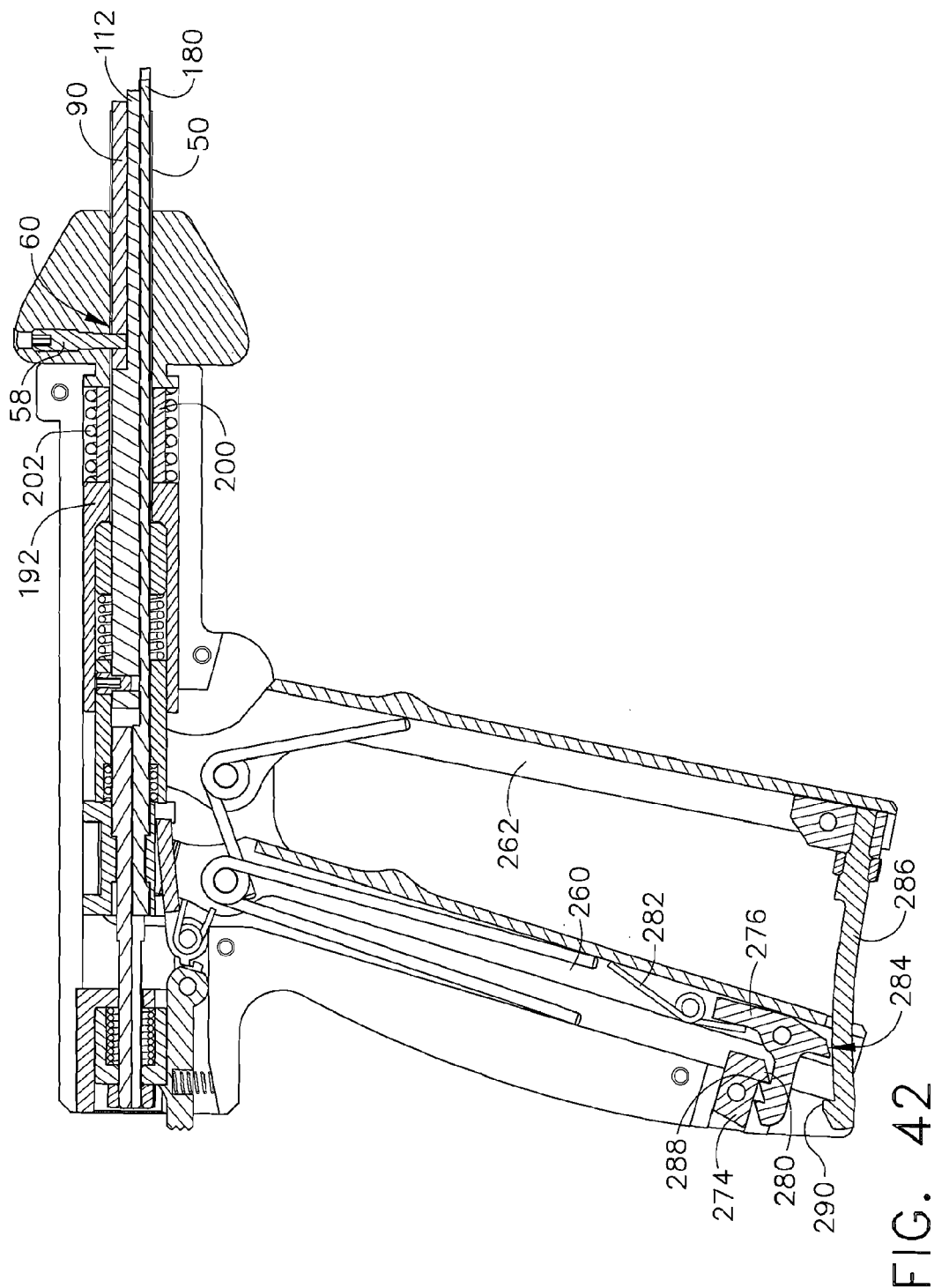
FIG. 42 is a side, sectional view of the proximal stapler end, similar to FIG. 41, showing the separator and former triggers in fully pivoted positions.
Figure 43:
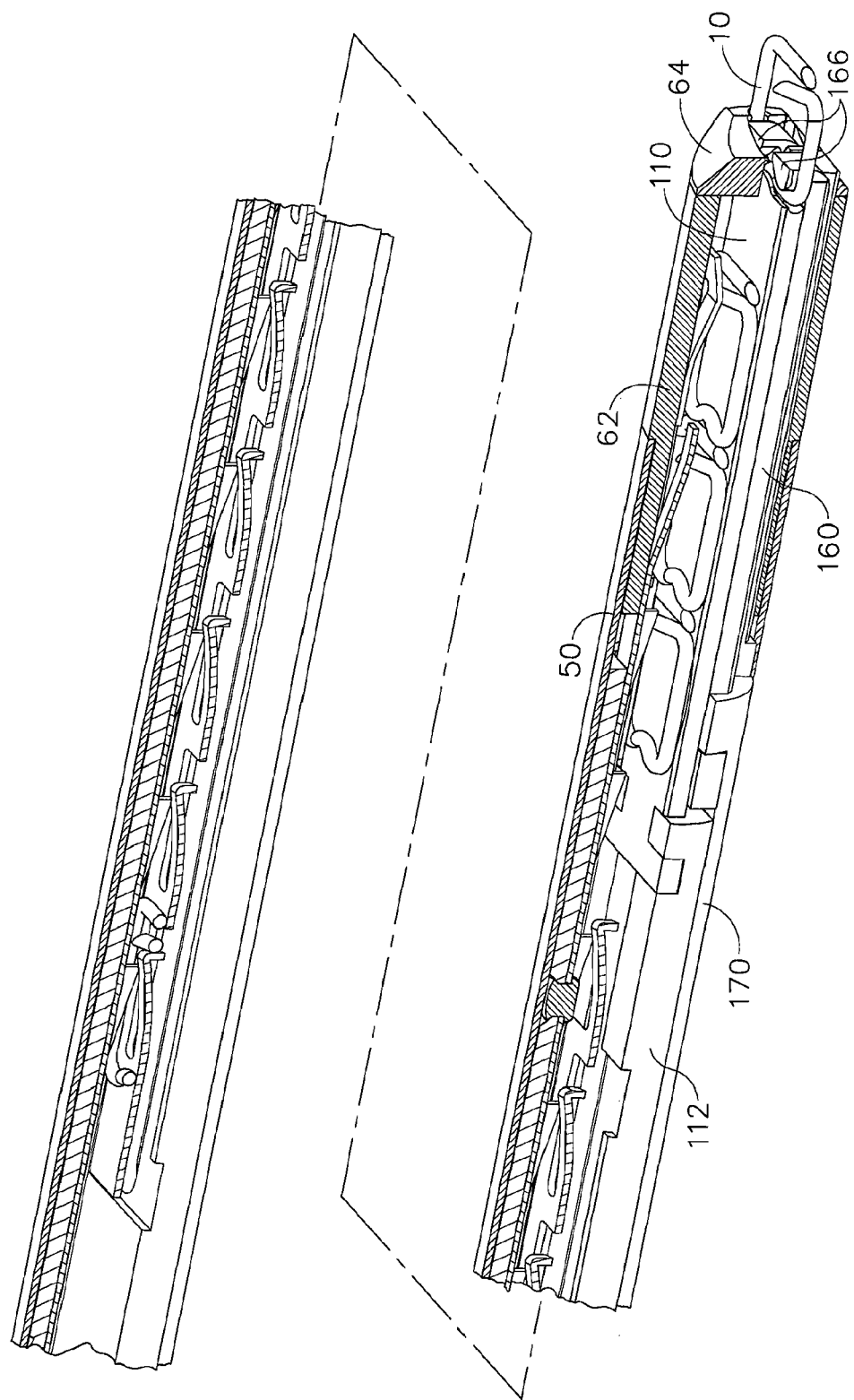
FIG. 43 is a fragmentary, isometric view, partially in section, of the distal stapler end showing the staple being formed by the former end cap.
Figure 46:
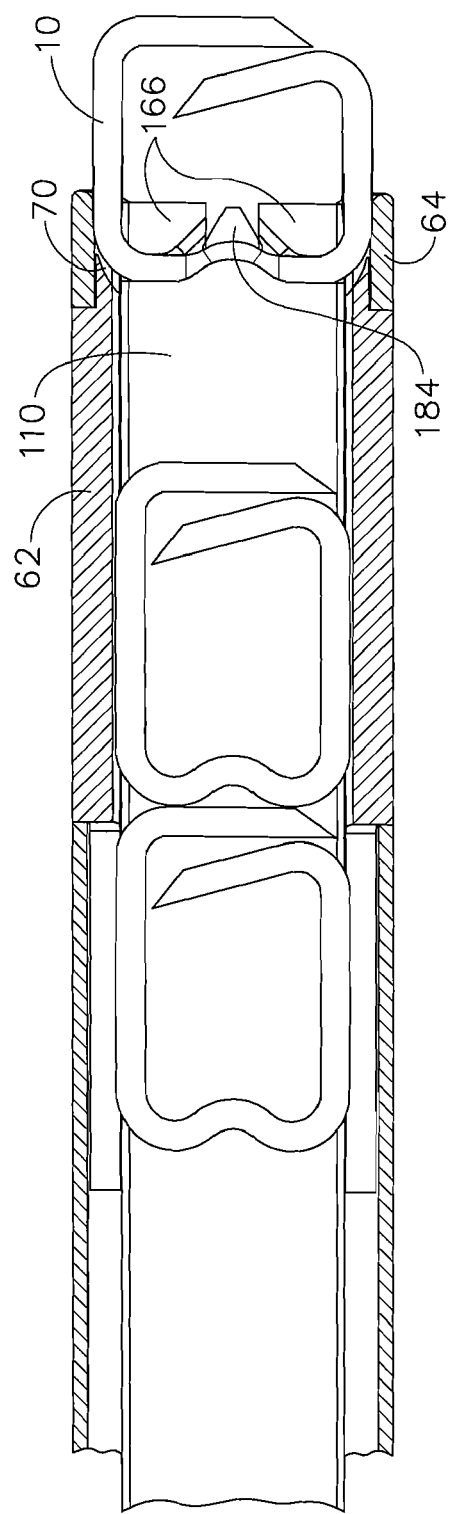
FIG. 46 is a top, partially sectional view of the distal stapler end depicting the same deployment stage as FIG. 44.
Figure 47:
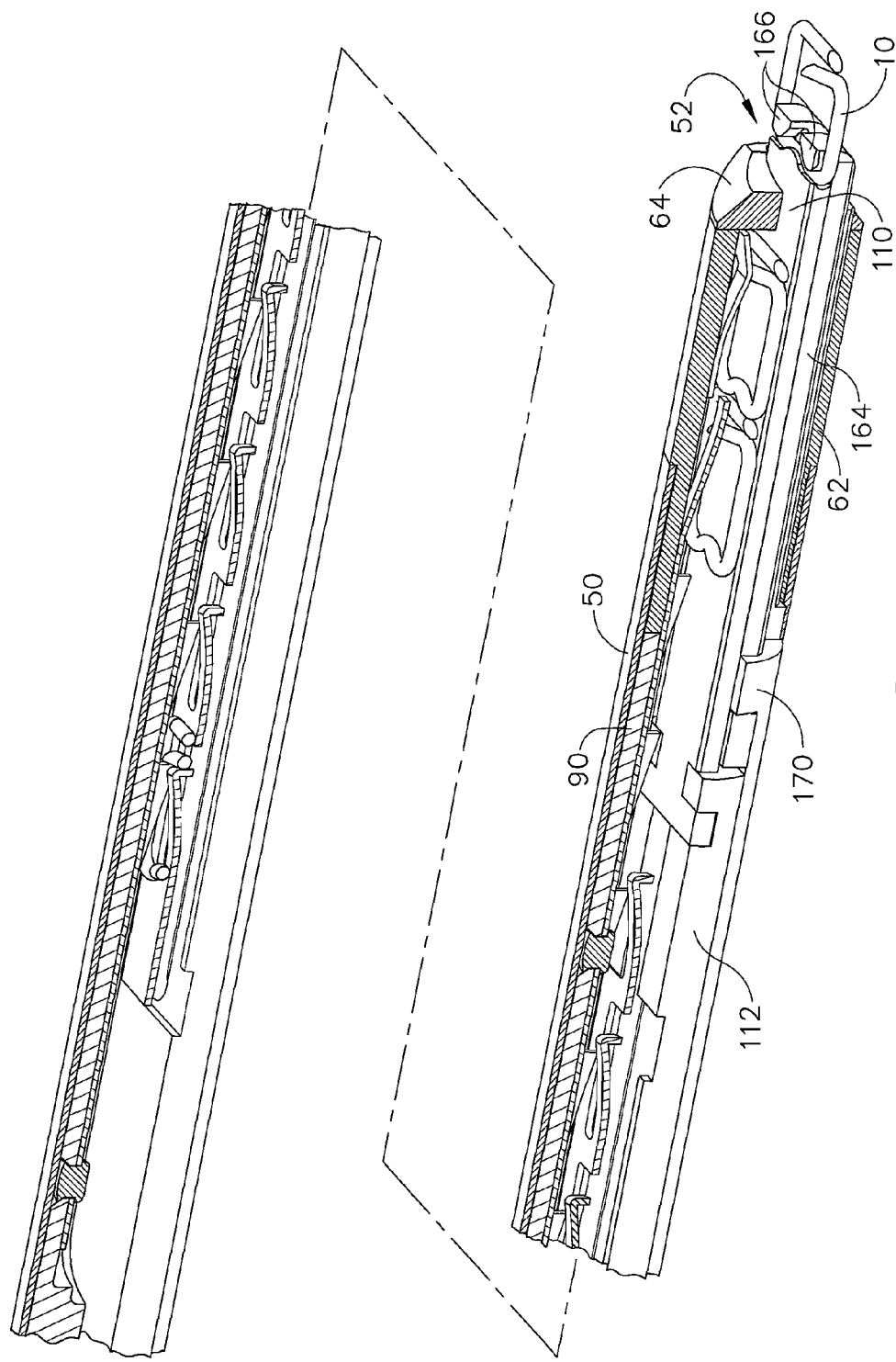
FIG. 47 is a fragmentary, isometric view, partially in section, of the distal end of the stapler showing the former retracted back from the formed staple.
Figure 50:
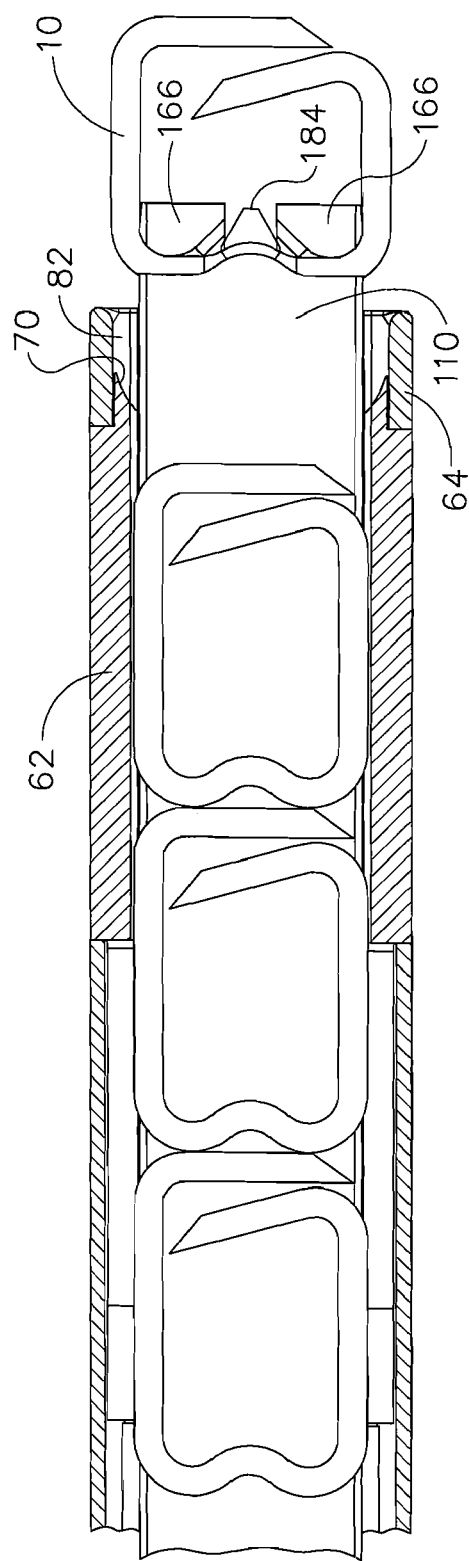
FIG. 50 is a top, partially sectional view of the distal stapler end depicting the same deployment stage as FIG. 47.

In the finished, closed shape, the width of the staple is greater than the previous, undeployed width, due to the different bending points along the staple length. This change in staple width enables the staple to have a low profile during delivery and a larger profile when formed through tissue. As staple legs 14, 16 are bending forward, prongs 26 are drawn back inward, grabbing onto the tissue or material in the spread between the prongs. As prongs 26 move inward, staple ends 20, 22 traverse an arc through the tissue, drawing the tissue into the closing staple. As prongs 26 reach an inward, preferably overlapping position, in which the staple 10 passes through the gripped tissue, former end cap 64 reaches its distal-most position. At this distal-most position, setting radii 70 at the proximal ends of former grooves 82 impact the bends between staple back span 12 and staple legs 14, 16 to plastically deform the outer edges of the intersection between the back span and staple legs, as described above. Inside handle 42, former bushing 192 contacts the proximal end of former distal stop 200, compressing spring 202 between the bushing and knob 54, and preventing further distal advance of the bushing. As an alternative to the end stop formed between former bushing 192 and former stop 200, an end stop can be reached by the bottoming out of pin 58 against the proximal end of housing slot 60. As the former reaches a distal end stop, former trigger 262 reaches a fully pivoted position, as shown in FIGS. 41-42, and trigger release 286 is drawn back to position release head 290 proximal of pawl tip 284. At this point, shown in FIGS. 43-46, staple 10 is fully formed through the tissue (not shown), and further squeezing of actuating assembly 46 is prevented.

Following formation of staple 10, the squeezing pressure on former trigger 262 is released, allowing the trigger to pivot back open under the force of former leaf spring 272. As former trigger 262 pivots open, the upper trigger lobes rotate back, allowing former return spring 202 to propel former bushing 192 proximally within the handle. As former bushing 192 moves proximally, the bushing forces housing clamp screw 196 back as well, pulling housing 50 back proximally by the locked flanges 194. As housing 50 retracts, pin 58 moves to the distal end of housing slot 60, and former end cap 64 is drawn away from the formed staple, releasing the staple from the former, as shown in FIGS. 47-50. As former end cap 64 retracts proximally, the formed staple 10 remains locked in the tissue (not shown), and held between anvil tines 166 and clamp 110 outside the open stapler end 52.

Figure 51:
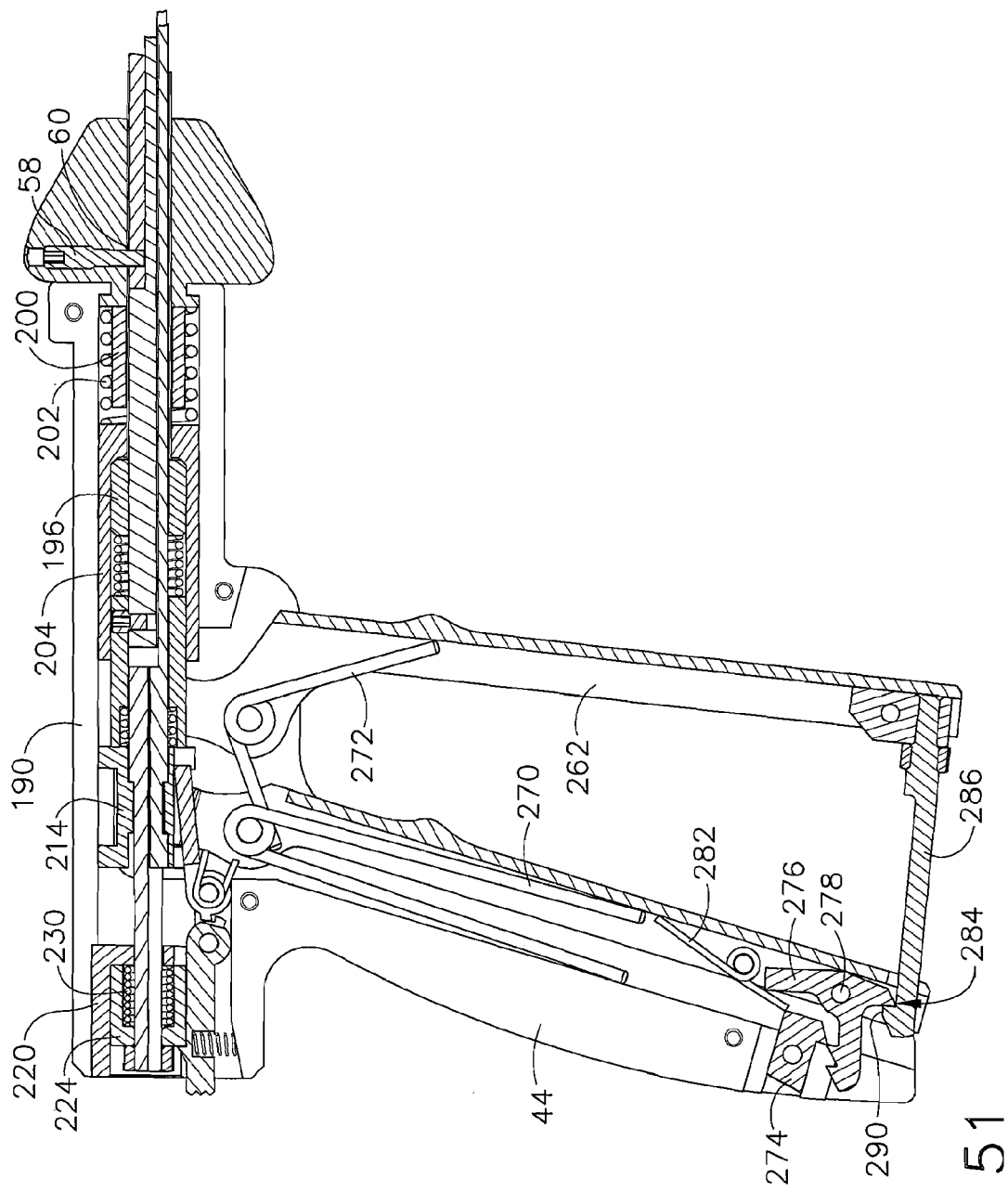
FIG. 51 is a side sectional view of the proximal stapler end showing the former trigger retracting open and tripping the separator trigger pawl.
Figure 52:
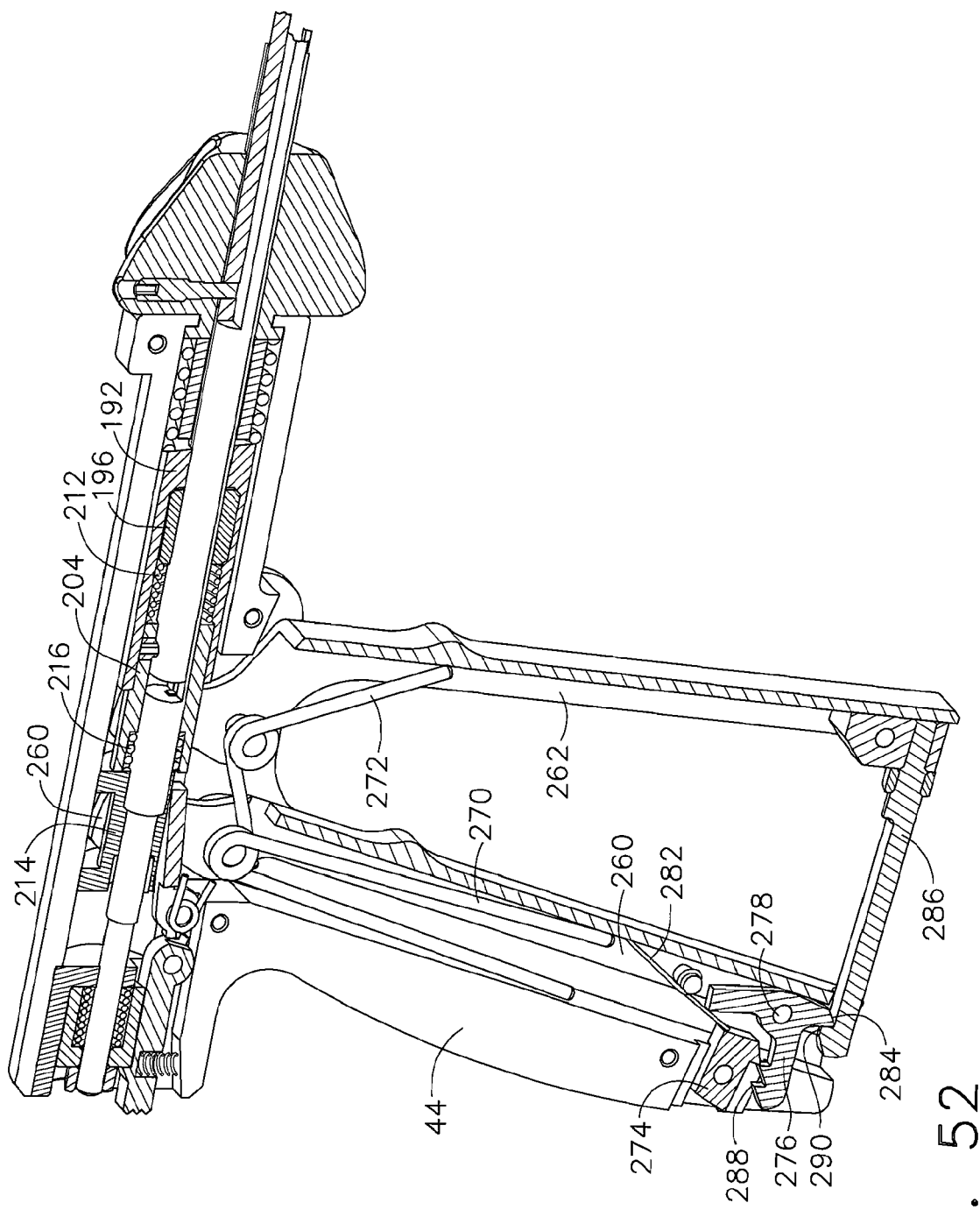
FIG. 52 is an isometric, sectional view of the proximal end of the stapler showing the same deployment stage as FIG. 51.
Figure 53:
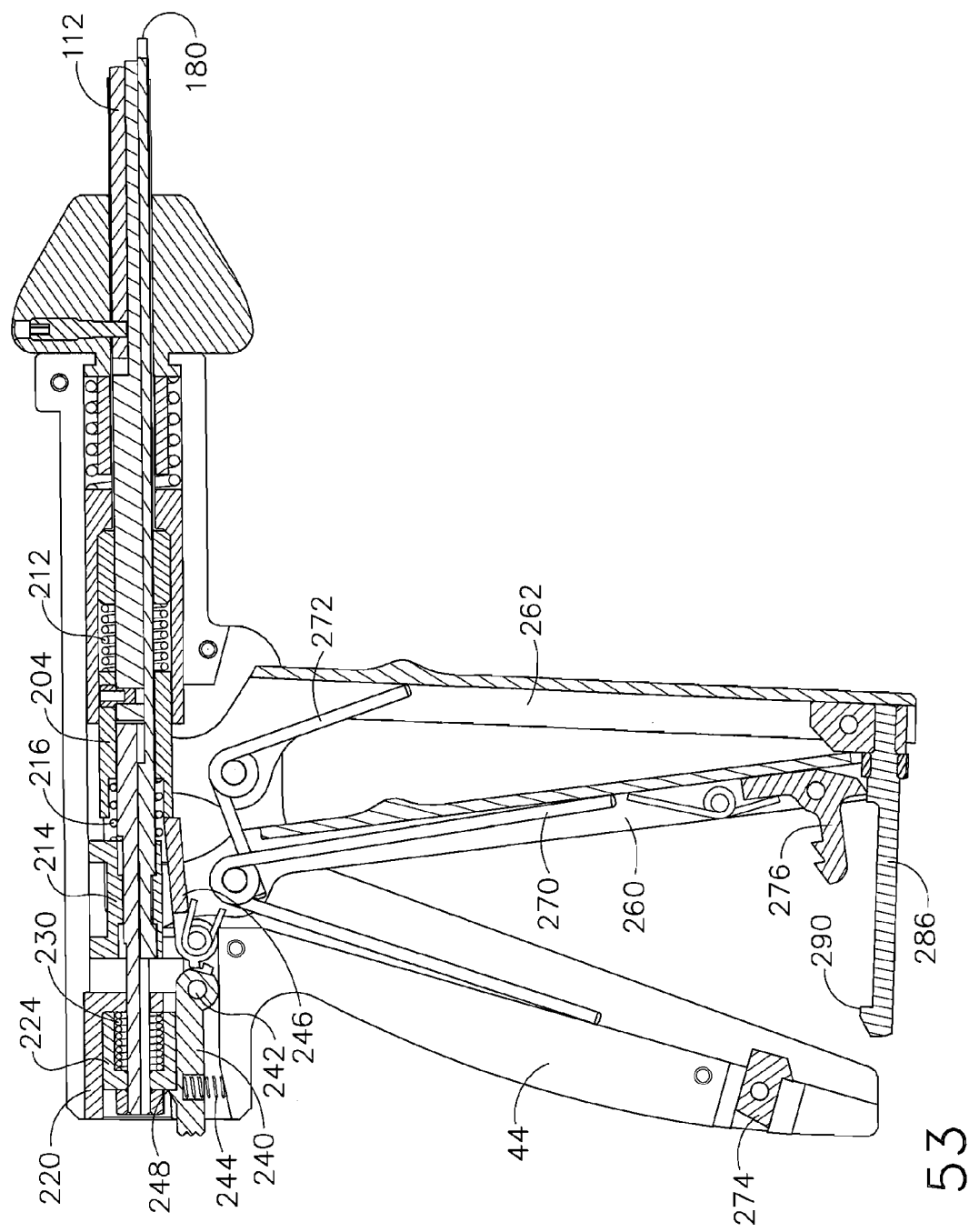
FIG. 53 is a side sectional view of the proximal stapler end showing the separator and former triggers retracting open.
Figure 54:
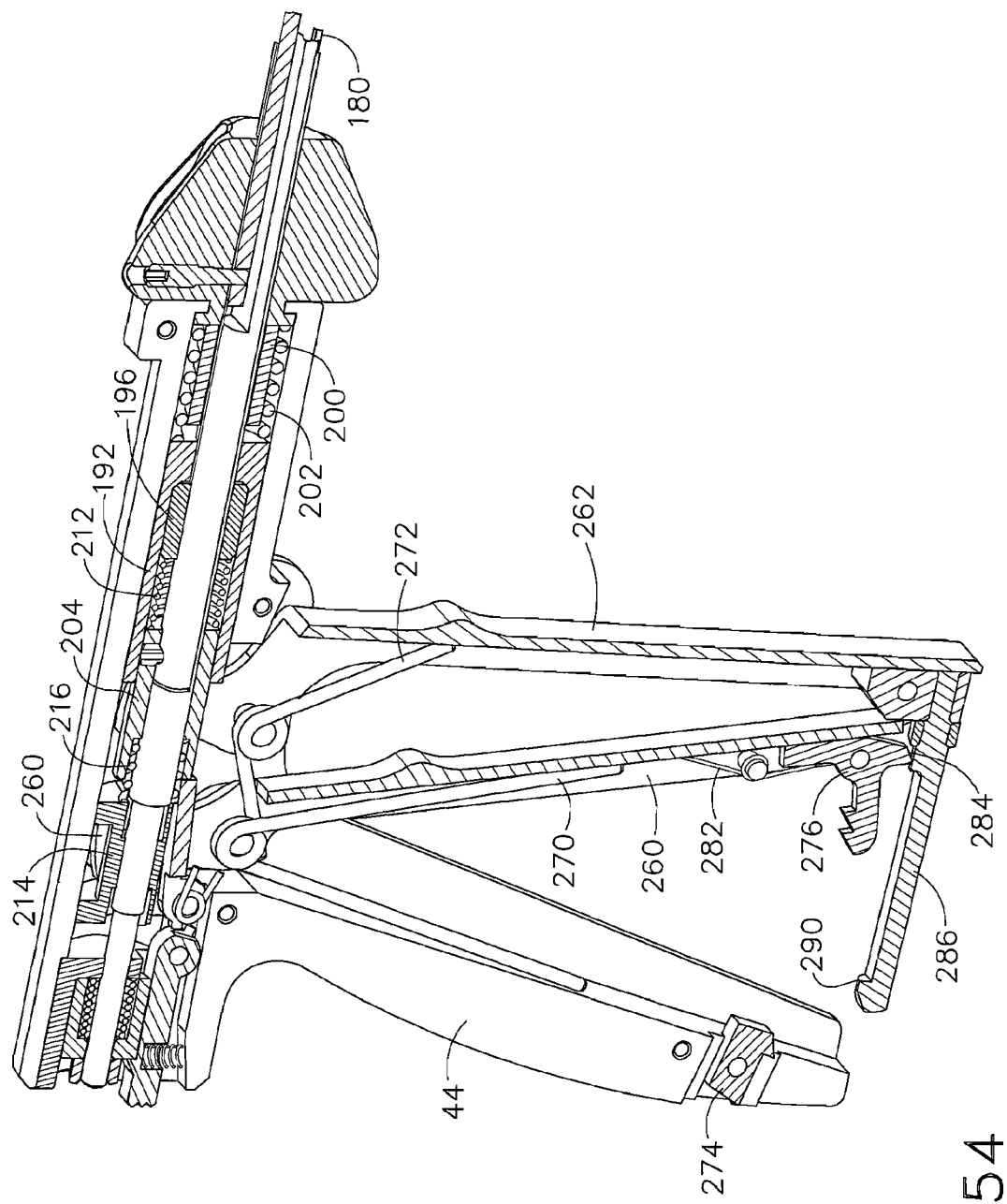
FIG. 54 is an isometric, sectional view of the proximal end of the stapler showing the same deployment stage as FIG. 53.
Figure 55:
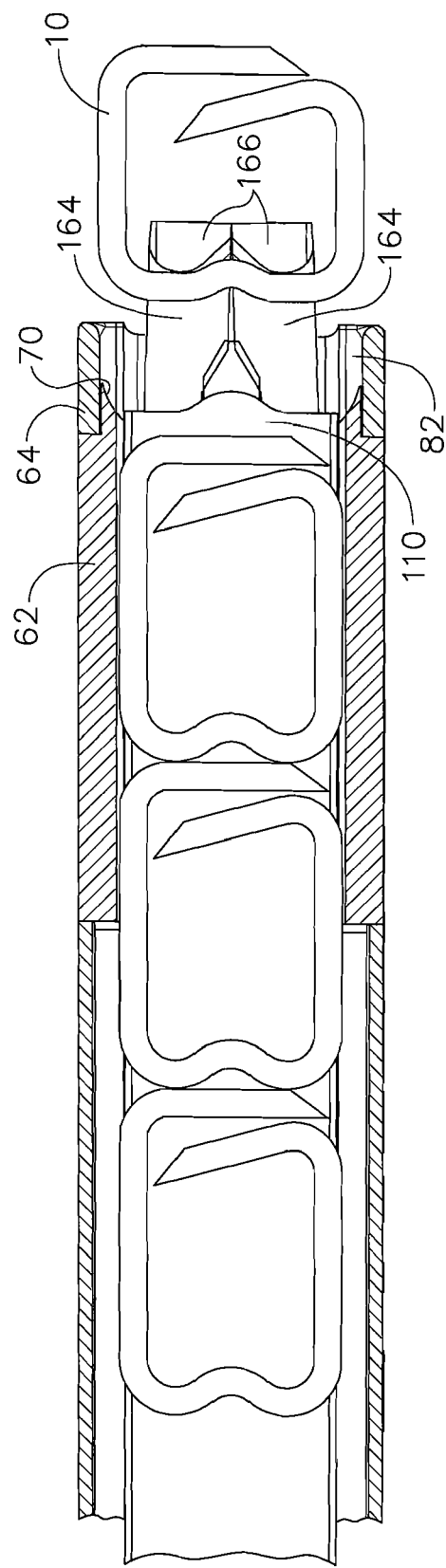
FIG. 55 is a top, partially sectional view of the distal stapler end depicting the clamp retracted back from the staple and anvil tines prior to staple release.

As trigger 262 pivots open, trigger release 286 rotates distally beneath pawl 276 with release head 290 tripping pawl tip 284, as shown in FIG. 51-52. The contact between the moving release head 290 and pawl tip 284 pivots pawl 276 about pin 278, against the force of pawl spring 282, drawing pawl teeth 288 down and out of engagement with trigger latch 274. The disengagement of pawl teeth 288 from latch teeth 280 releases separator trigger 260 from the locked condition, allowing the trigger to pivot back open under the force of separator leaf spring 270, as shown in FIGS. 53-54. As separator trigger 260 pivots back open, the upper lobes of the trigger push in the proximal direction against separator driver 214. This proximal force on separator driver 214 pulls the driver and attached separator 180 back proximally. Separator driver 214 continues pulling separator 180 proximally, under the force of separator trigger 260, until the separator is retracted back to the initial deployment position. Separator driver 214 is assisted in moving proximally by the expanding separator spring 216. As separator 180 moves proximally, separator tip 184 is withdrawn from between anvil tines 166, allowing the tines to pull back inward and away from the sides of staple legs 14, 16, as shown in FIGS. 55-58. After contacting pawl tip 284, former trigger 262 continues pivoting open until the upper edge of the trigger rotates into contact with an angled edge of handle cover 190, as indicated at 292 in FIGS. 59-60, preventing further opening of the trigger.

The proximal movement of separator driver 214 also releases clamp bushing 204 to move proximally under the force of expanding clamp spring 212. As clamp bushing 204 moves proximally, the bushing pulls the attached clamp extension 112 and clamp 110 back proximally, retracting the clamp from the formed staple as shown in FIGS. 55-58. As mentioned above, staple stack 100 rides along the surface of clamp 110 and clamp extension 112. As clamp 110 is advanced distally, the staple stack 100 advances along with the clamp. Following staple formation, clamp 110 is refracted back inside the open stapler end 52. As mentioned above, a staple indexing body 140 extends along the upper surface of staple stack 100. Indexing body 140 is connected to staple guide 90 to remain stationary during the staple deployment process. Staple indexing body 140 includes a plurality of holding arms 142 which engage the individual staples in stack 100. As clamp 110 retracts following staple formation, the distal ends of holding arms 142 push against the inner most ends 22 on the individual staples 12, as shown at 294 in FIG. 56. Contact between the stationary holding arms 140 and the staples 10 prevents the staple stack 100 from retracting along with clamp 110, thereby keeping the stack in a distal position for indexing the next staple into the discharge channel. As shown in FIGS. 53-54, the retracting clamp bushing 204 contacts the distal end of clamp catch 246, stopping proximal movement of the clamp 110. The contact between clamp catch 246 and clamp bushing 204 provides a pause in the deployment process for release of the formed staple 10 from stapler 40.

After clamp 110 and separator 180 are retracted proximally, the formed staple 10 can be released from stapler 40 by maneuvering the anvil 160 if needed (via handle 42) away from the staple. Staple ejecting members may also be incorporated into anvil 160 for aiding in the release of the formed staple from the anvil. As shown in FIGS. 72 and 73, the staple ejecting members can comprise springs 296 which are recessible within anvil arms 164 beneath the staged staple. Springs 296 are biased into an outward exposed position. As clamp 110 moves distally over anvil arms 164 to advance staple 10 during deployment, the clamp pushes springs 296 downward into recesses within the anvil arms, and away from the staple. As clamp 110 and separator 180 retract following staple formation, the downward pressure of the clamp on springs 296 is released, allowing the springs to flex outward into contact with the staple back span. The force of springs 296 is greater than the retaining force of the anvil tines (which have collapsed inwardly following the retraction of separator 180), allowing the ejecting springs to push the staple off the anvil. In order to prevent premature release of a staple 10, the upward spring force of the ejecting members is less than the opposing, downward force of shoe 150, to enable the shoe to deposit another staple onto the anvil tines at the end of the deployment sequence without the staple being ejected or positioned out of plane with clamp 110.

Figure 59:
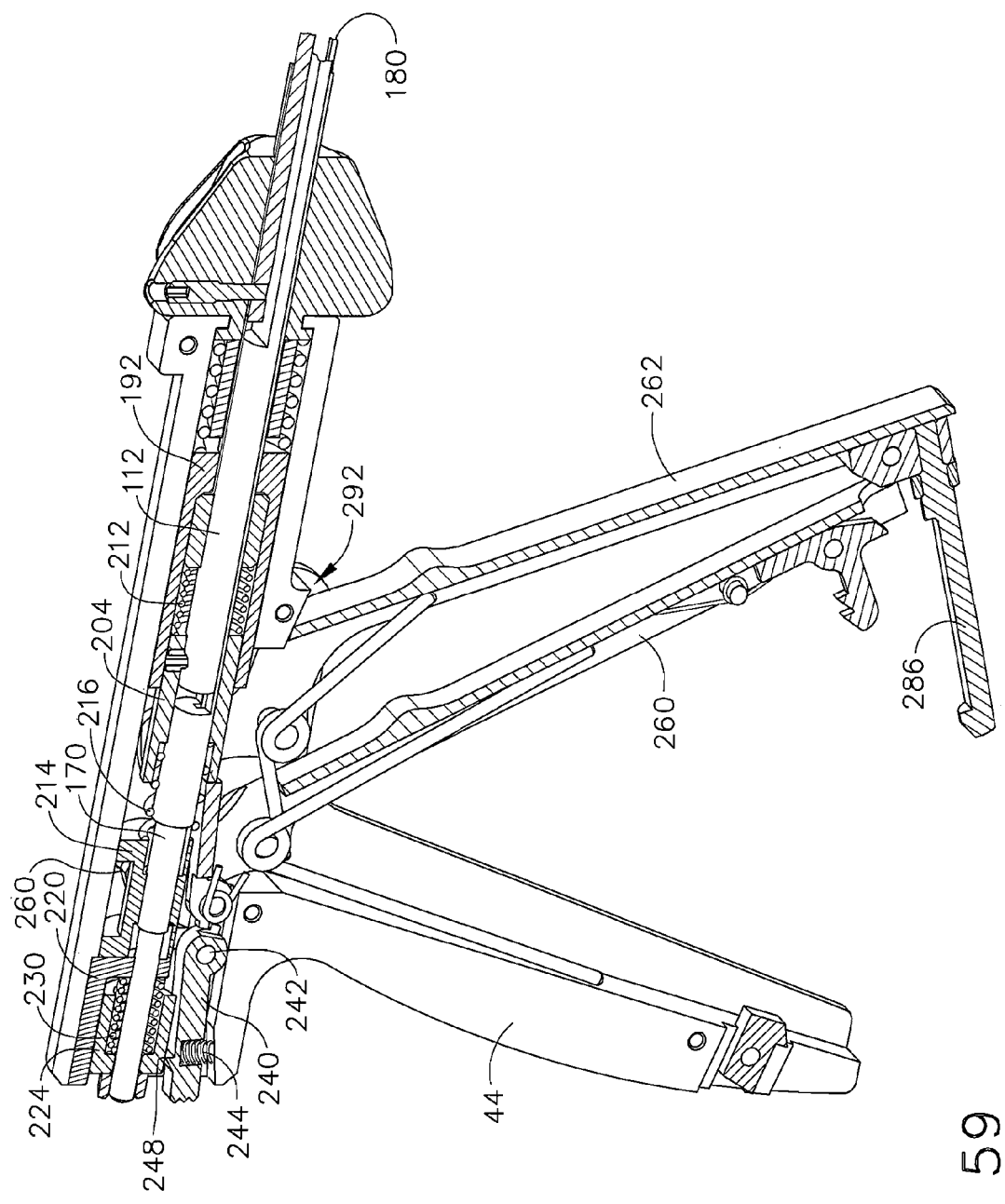
FIG. 59 is an isometric, sectional view of the proximal end of the stapler showing the anvil catch released to fully retract the anvil.
Figure 60:
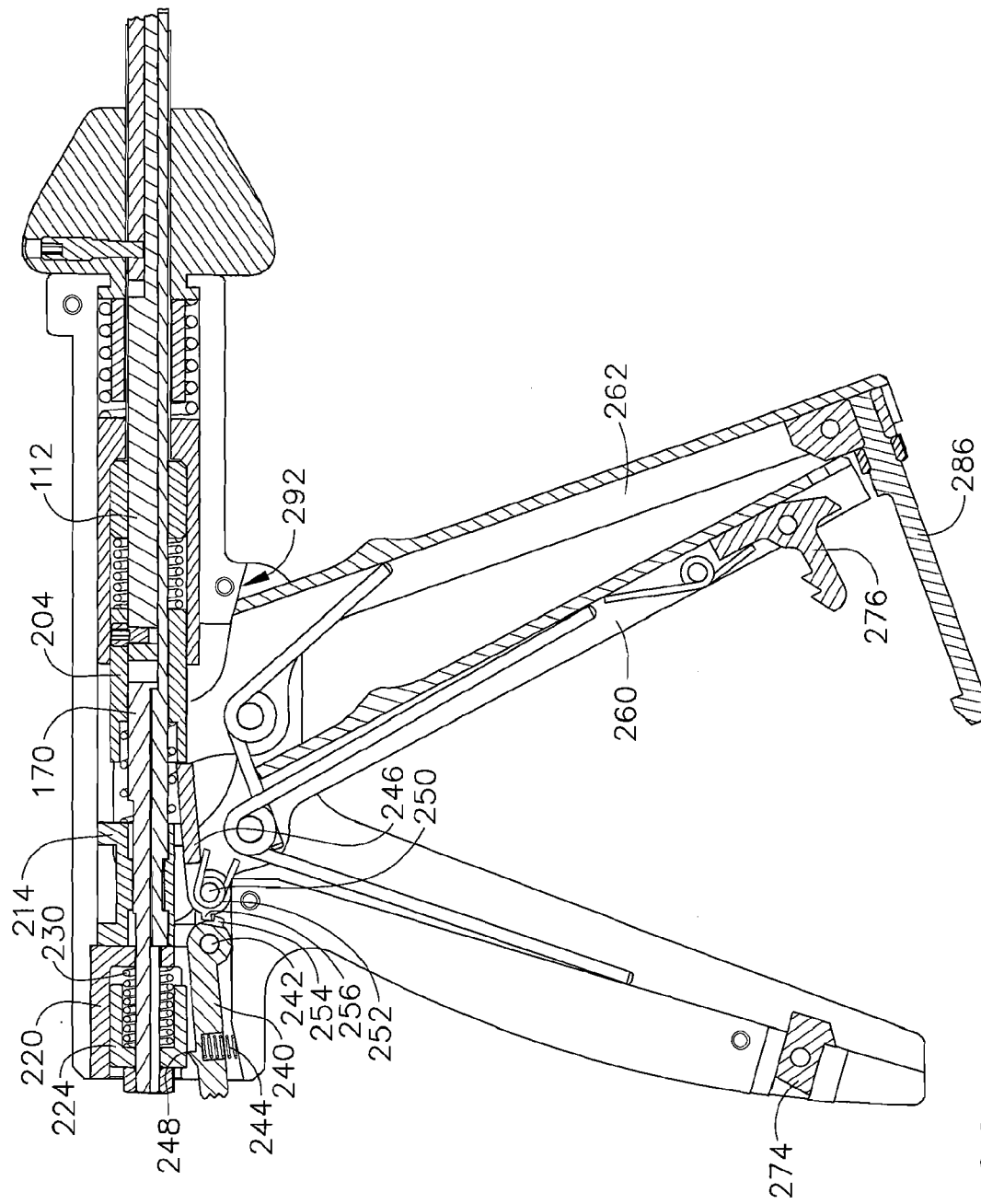
FIG. 60 is a side sectional view of the proximal stapler end showing the same deployment position as FIG. 59.
Figure 61:
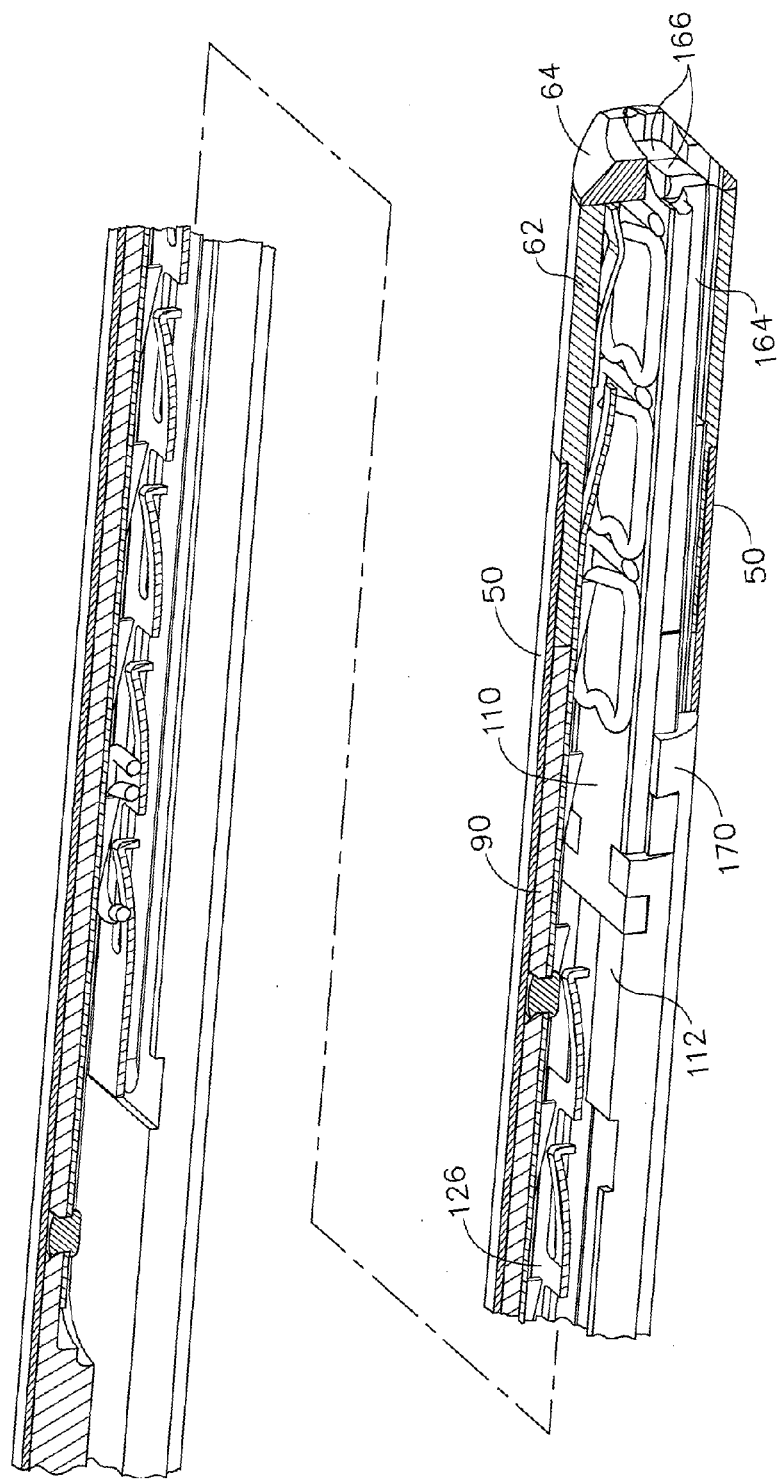
FIG. 61 is a fragmentary, isometric view, partially in section, of the distal end of the stapler showing the anvil tines retracted back within the stapler housing following staple release.
Figure 64:
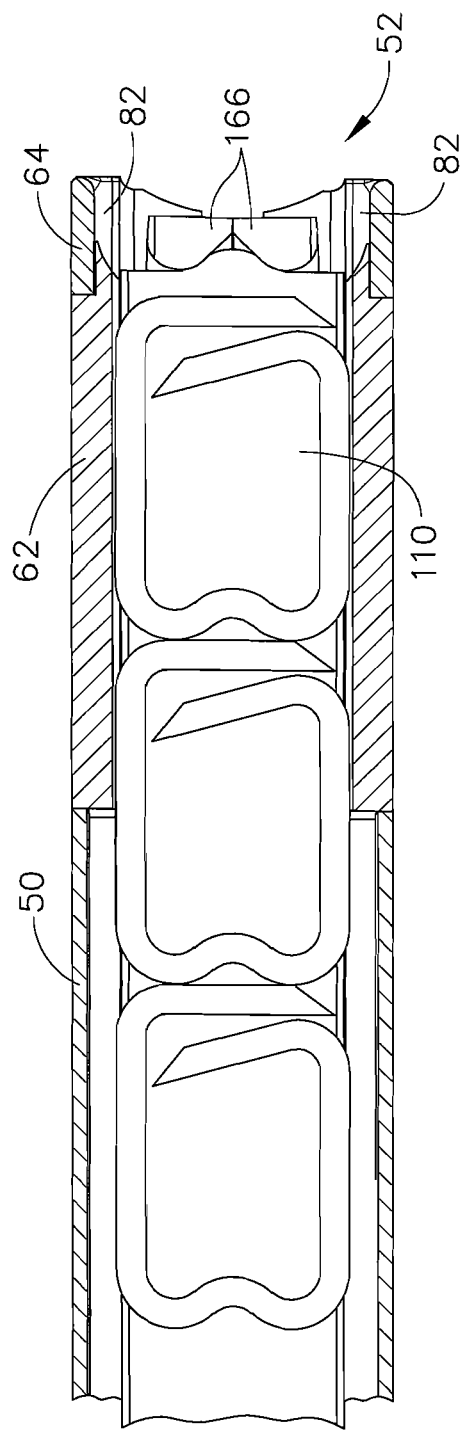
FIG. 64 is a top, partially sectional view of the distal stapler end showing the same deployment stage as FIG. 61.

After the release of staple 10, anvil 160 and clamp 110 are retracted within stapler 40 by pressing down on the proximal, exposed end of anvil catch 240. Pressure is applied to anvil catch 240 to overcome the upward force of anvil catch spring 244. Downward pressure on anvil catch 240 by a thumb or other external force, pivots anvil catch 240 in a downward direction about pin 242. As anvil catch 240 pivots about pin 242, anvil catch tip 248 moves out of contact with the proximal end of anvil stop 224, allowing the anvil stop to move proximally under the force of anvil spring 230, as shown in FIGS. 59-60. As anvil stop 224 moves proximally, anvil extension 170 and the attached anvil 160 are retracted back inside the distal end of former end cap 64, as shown in FIGS. 61-64.

Figure 65:
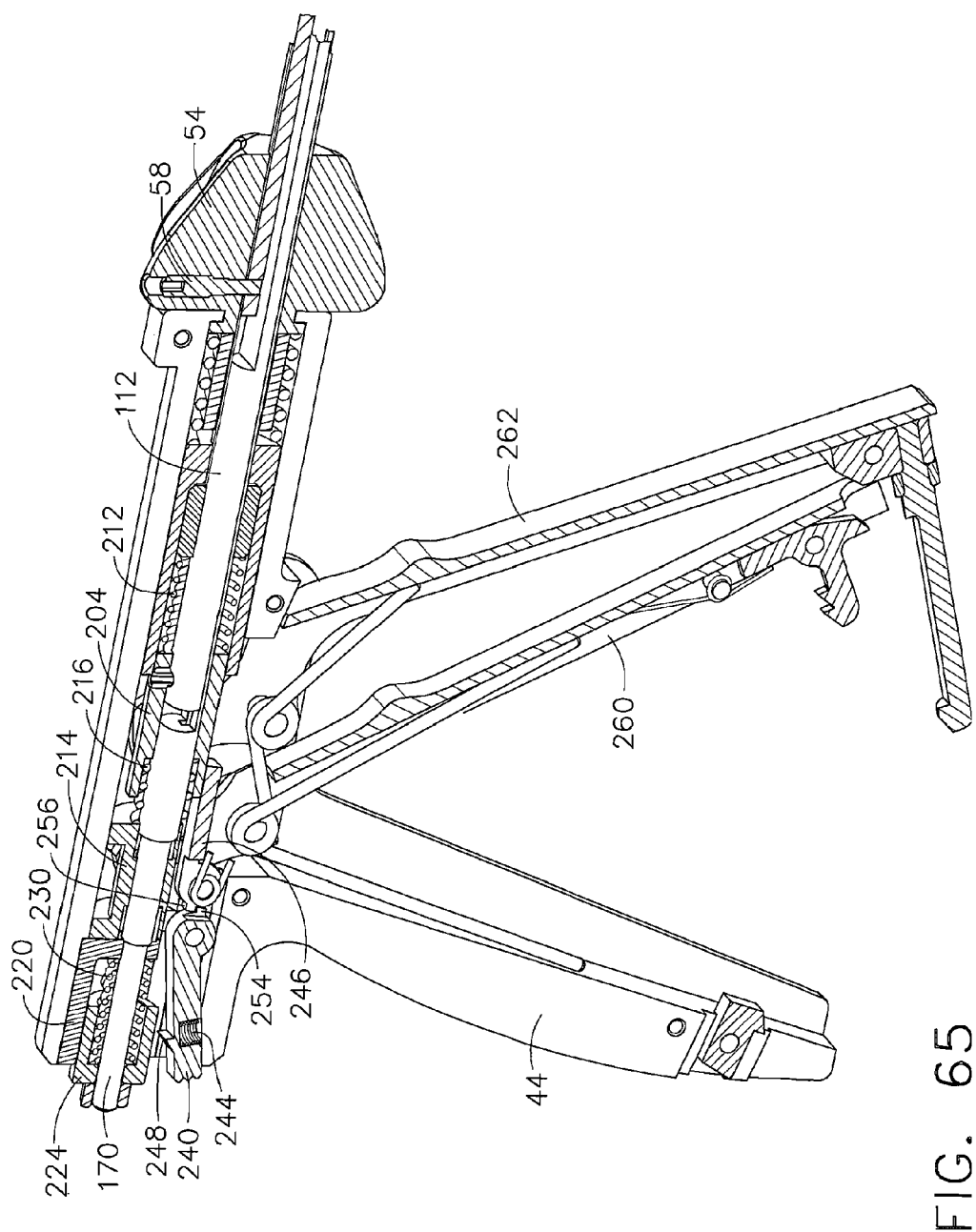
FIG. 65 is an isometric, sectional view of the proximal end of the stapler showing the anvil at a proximal end stop and the clamp catch released to fully retract the clamp.
Figure 66:
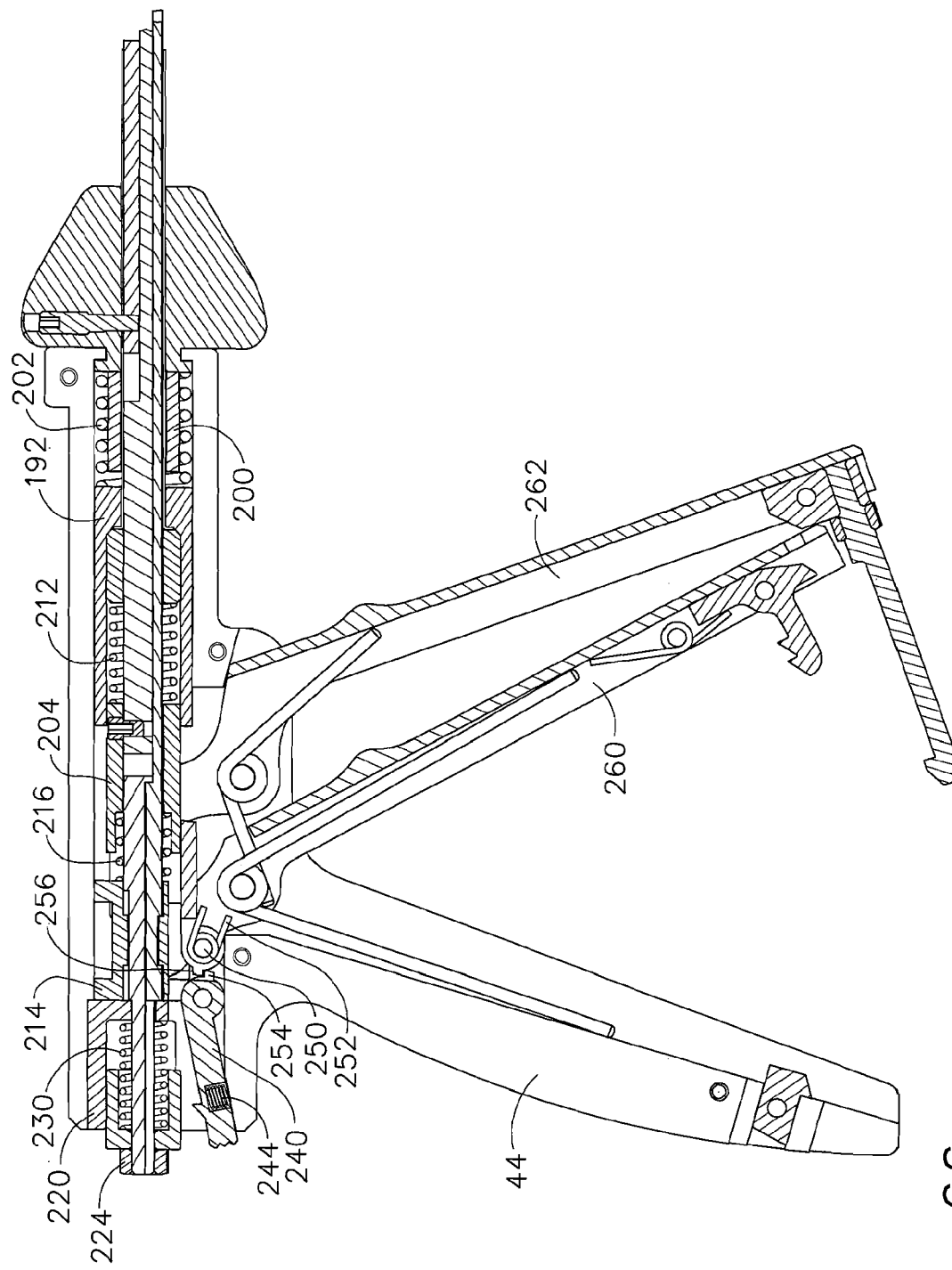
FIG. 66 is a side sectional view of the proximal stapler end showing the same deployment position as FIG. 65.
Figure 67:
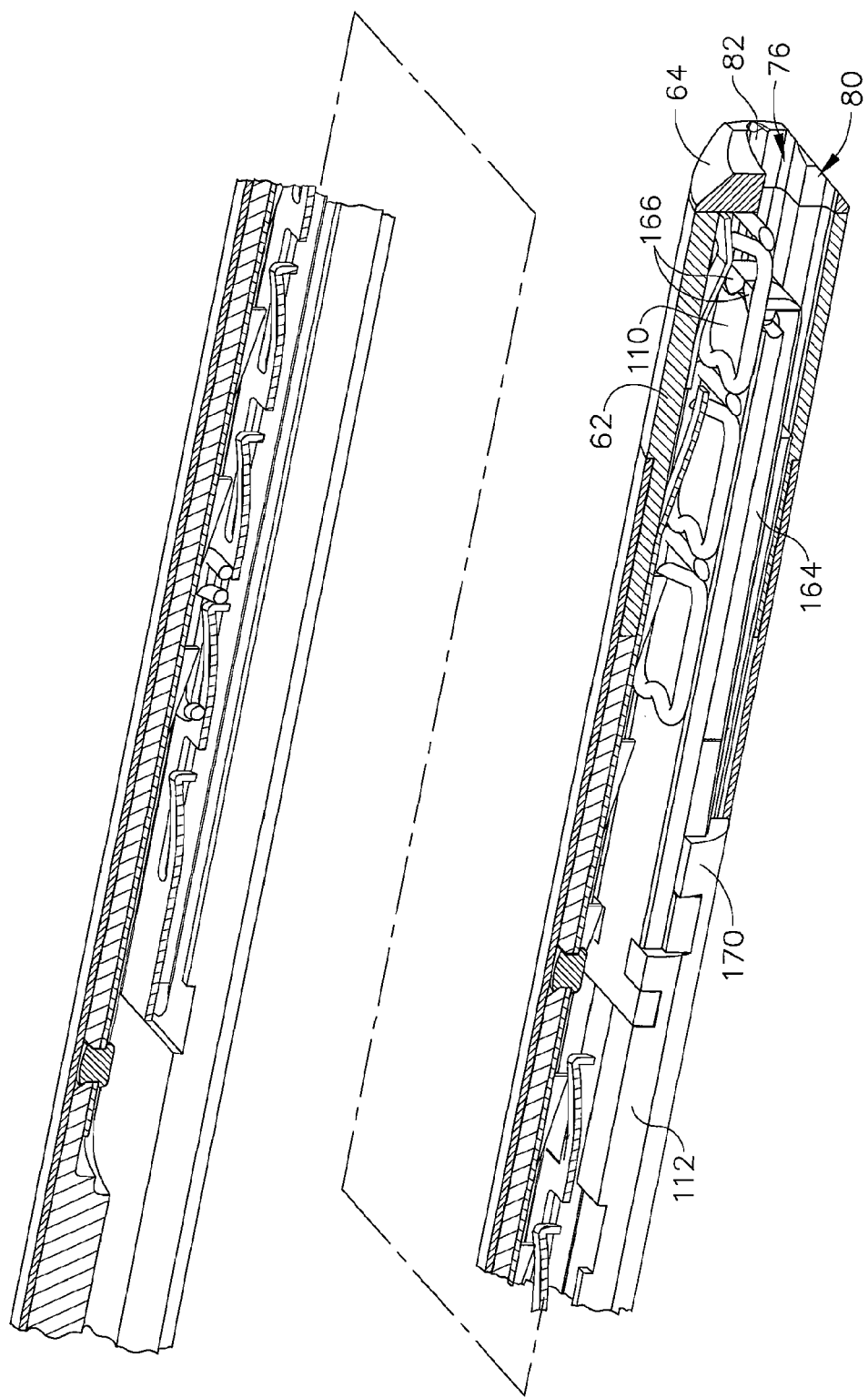
FIG. 67 is a fragmentary, isometric view, partially in section, of the distal end of the stapler showing the anvil and clamp retracted back beneath the distal staple in the stack.
Figure 68:
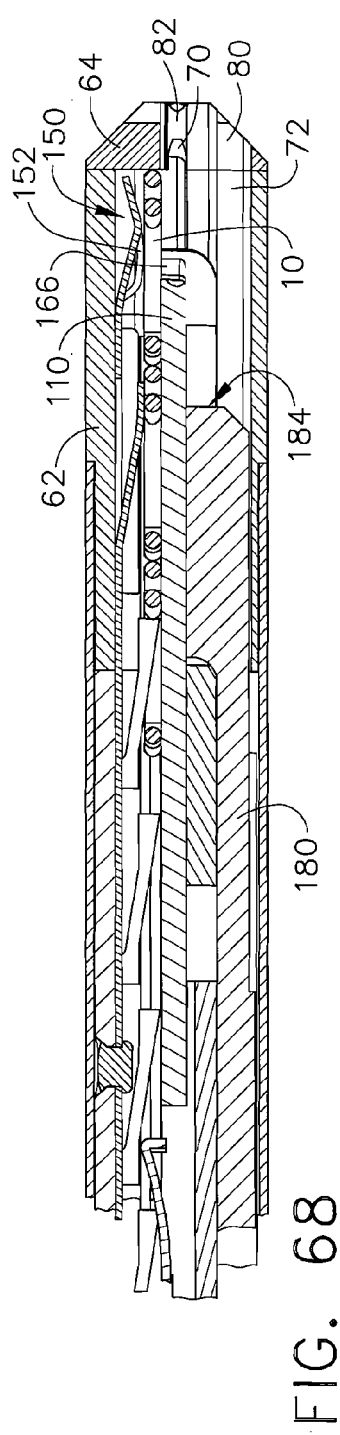
FIG. 68 is a side sectional view of the distal stapler end, taken along the longitudinal stapler axis, showing the same deployment stage as FIG. 67.
Figure 69:
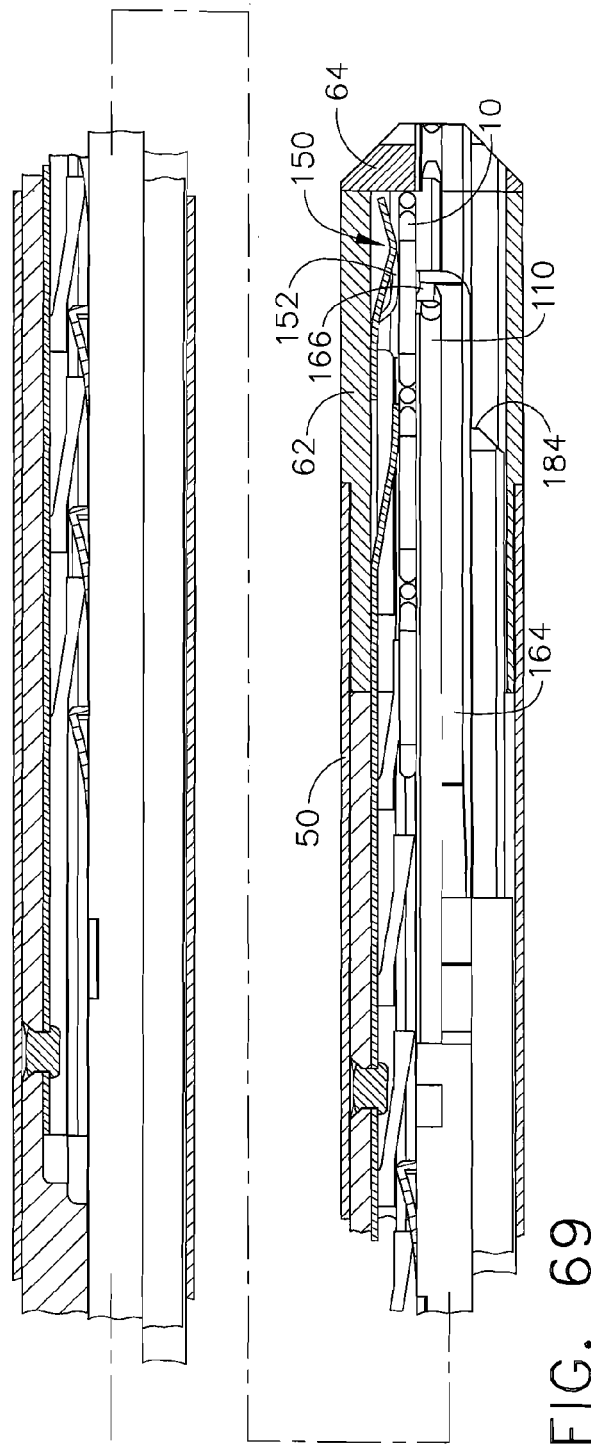
FIG. 69 is a side, fragmentary, partially sectional view of the distal stapler end showing the same deployment stage as FIG. 67.
Figure 70:
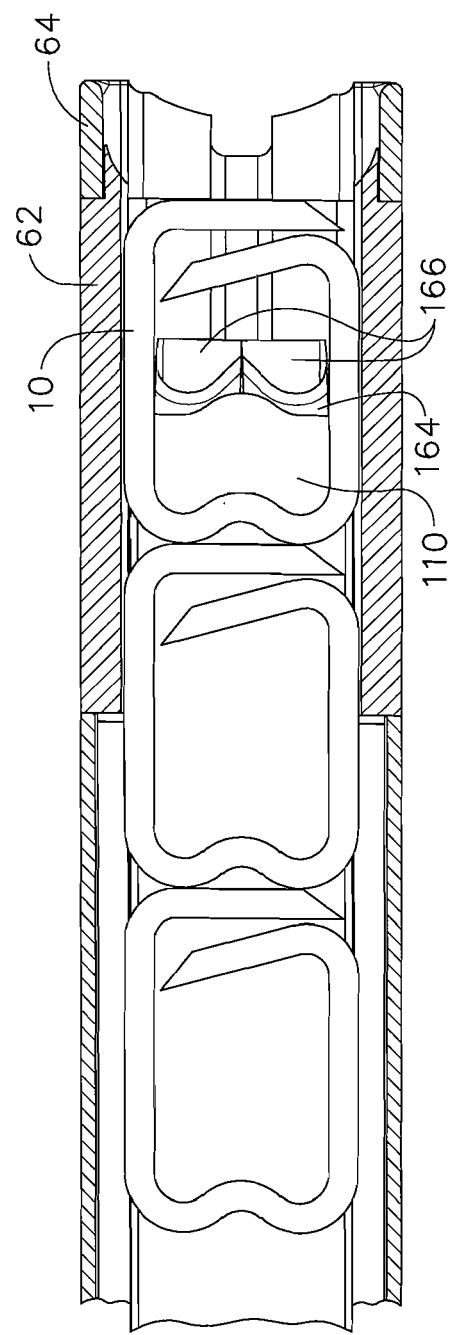
FIG. 70 is a top, partially sectional view of the distal stapler end showing the same deployment stage as FIG. 67.

As anvil catch 240 pivots downward, anvil detents 254, located on the proximal side of pivot pin 242, rotates in an upward direction toward clamp catch detents 256, as shown in FIGS. 65-66. Anvil detents 254 contacts clamp catch detents 256 after catch tip 248 has cleared the proximal end of anvil stop 224. The force of anvil detents 254 against clamp detents 256 causes catch clamp 246 to rotate in the opposite direction about clamp catch pin 250. As catch clamp 246 rotates, the distal end of the catch is drawn out of contact with the proximal end of clamp bushing 204, enabling the bushing to resume retracting proximally under the force of clamp spring 212. Detents 254, 256 are positioned about the respective anvil and clamp catches 240, 246 so as to produce a time delay between the start of anvil retraction and the continuation of the clamp retraction. This dwell time allows anvil tines 166 to retract back towards clamp 110, to close the gap between the anvil tines and distal clamp face, as shown in FIGS. 67-70, prior to the anvil and clamp retracting back together into former body 62.

After clamp bushing 204 is released from clamp catch 246, the bushing continues retracting under the force of clamp spring 212 until the clamp spring is expanded back to its initial condition, as shown in FIG. 65. Likewise, anvil stop 224 continues retracting proximally until anvil spring 230 returns to an initial, uncompressed condition. Anvil 160 stops retracting prior to clamp 110, enabling the clamp to retract beyond the anvil tines 166 within the discharge channel, leaving a gap between the distal clamp face and the anvil tines. As clamp 110 and anvil tines 166 move back proximally, the clamp and anvil tines pass underneath the staple at the distal end of stack 100. As the gap forms between clamp 110 and anvil tines 166, the downward force of shoe 150 pushes the distal staple from stack 100 down into the discharge channel. Side rails 152 push down on staple legs 14 16 to place the staple legs in parallel with the sidewalls of former body channel 66, the staple back span 12 between the distal clamp face and anvil tines, and the anvil tines extending up through the closed staple loop. As the staple 10 drops into this staged position in the discharge channel, clamp 110 finishes retracting to its initial deployment position (shown in FIGS. 18-20), thus completing the resetting of the stapler. With the actuator assembly 46 and the staple deploying assembly fully reset to the initial deployment conditions, and a new staple staged on the anvil tines 166, stapler 40 is ready to be re-fired to deploy the next staple.

Figure 77:
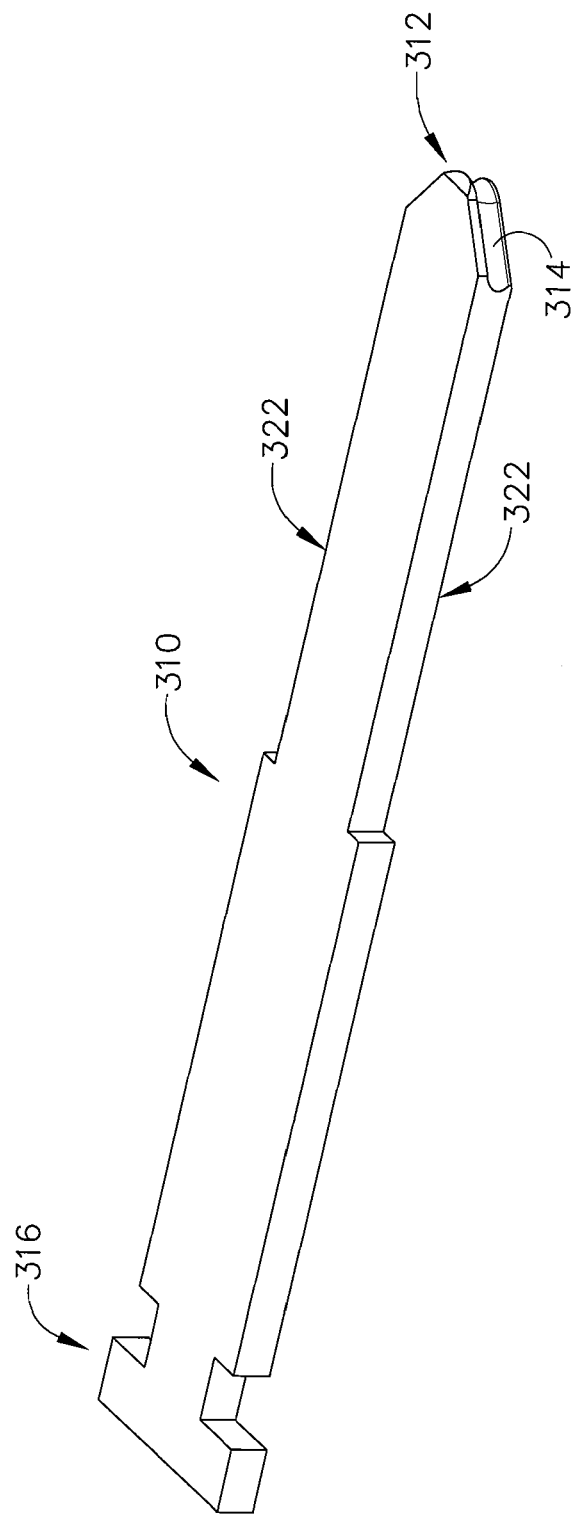
FIG. 77 is an isometric view of the spreader shown in FIGS. 74 and 75.

Turning now to FIGS. 74 and 75 which depict an alternative embodiment for stapler 40. In this embodiment, the stapler is modified to include a spreader 310 for opening the staple 10 during the deployment sequence. Spreader 310 opens the staple 10 by applying a distally directed force to the staple back span 12 (shown in FIG. 76) while the staple is pinned against the proximal face of the anvil tines 166. The force of spreader 310 is applied to a mid-section of back span 12, while the back span is held fixed at the intersections between the back span and staple legs 14, 16 by the anvil tines. The force of spreader 310 against the opposite fixed forces at the leg intersections pulls the staple legs 14, 16 outward, expanding open the staple, while substantially simultaneously indenting the center of the back span 12. Spreader 310 has a similar shape and location within the stapler 40 as clamp 110 of the previous embodiment, with the exception of the distal spreader end 312, which is angled inwardly to a center tip as shown in FIG. 77. The angle of the distal spreader end 312 is preferably approximately 45° relative to the longitudinal axis of the stapler, although lesser or greater angles can be applied to the spreader end to vary the opening size, the rate of opening, or to adjust the holding force of the staple. The distal angled face of the spreader 310 includes an inward radius, as indicated at 314, for mating against the outer circumference of the staple back span. The proximal end of spreader 310 includes a T-connector 316 for attachment to the extension 112 described in the previous embodiment in connection with clamp 110. Extension 112 advances spreader 310 distally within the discharge channel to deform the back span of the staged staple during the deployment sequence.

Figure 78:
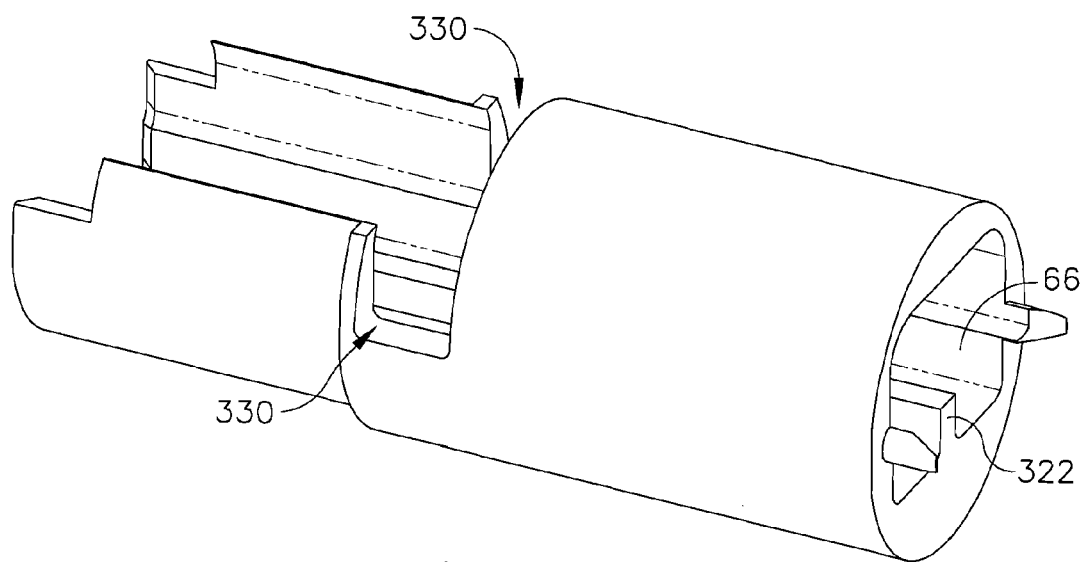
FIG. 78 is an isometric view of an alternative former body.
Figure 79:
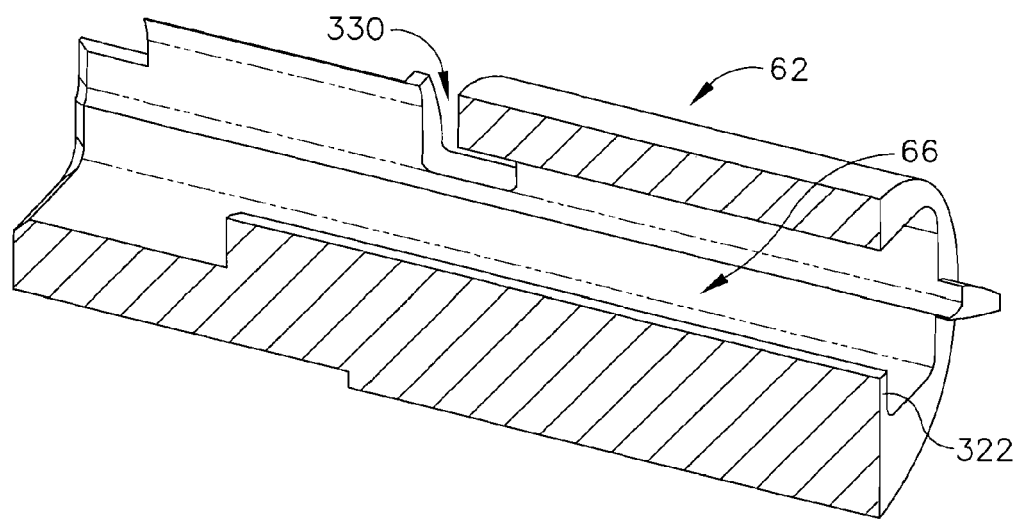
FIG. 79 is an isometric view, partially in section, of the former body shown in FIG. 78.

Also in this embodiment, former body 62 is modified to include a center rib 322, shown in greater detail in FIGS. 78 and 79, extending longitudinally into former body channel 66. Rib 322 contacts staple 10 as the staple is pushed down into the discharge channel by shoe 150, providing support for the distal end (i.e. end segments 20, 22) of the staple as the staple is staged within the discharge channel. Rib 322 is positioned to sit between anvil arms 164 as the anvil, staple and spreader 310 are advanced through the former body 62 during deployment. As spreader 310 pushes against the staple 10, the staple moves along the upper surface of rib 322 and outside the open stapler end 52.

Figure 80:
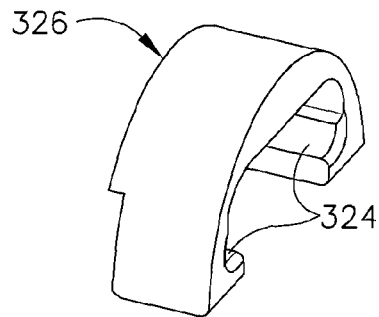
FIG. 80 is an isometric view of an insert piece for the former body of FIGS. 78 and 79.
Figure 81:
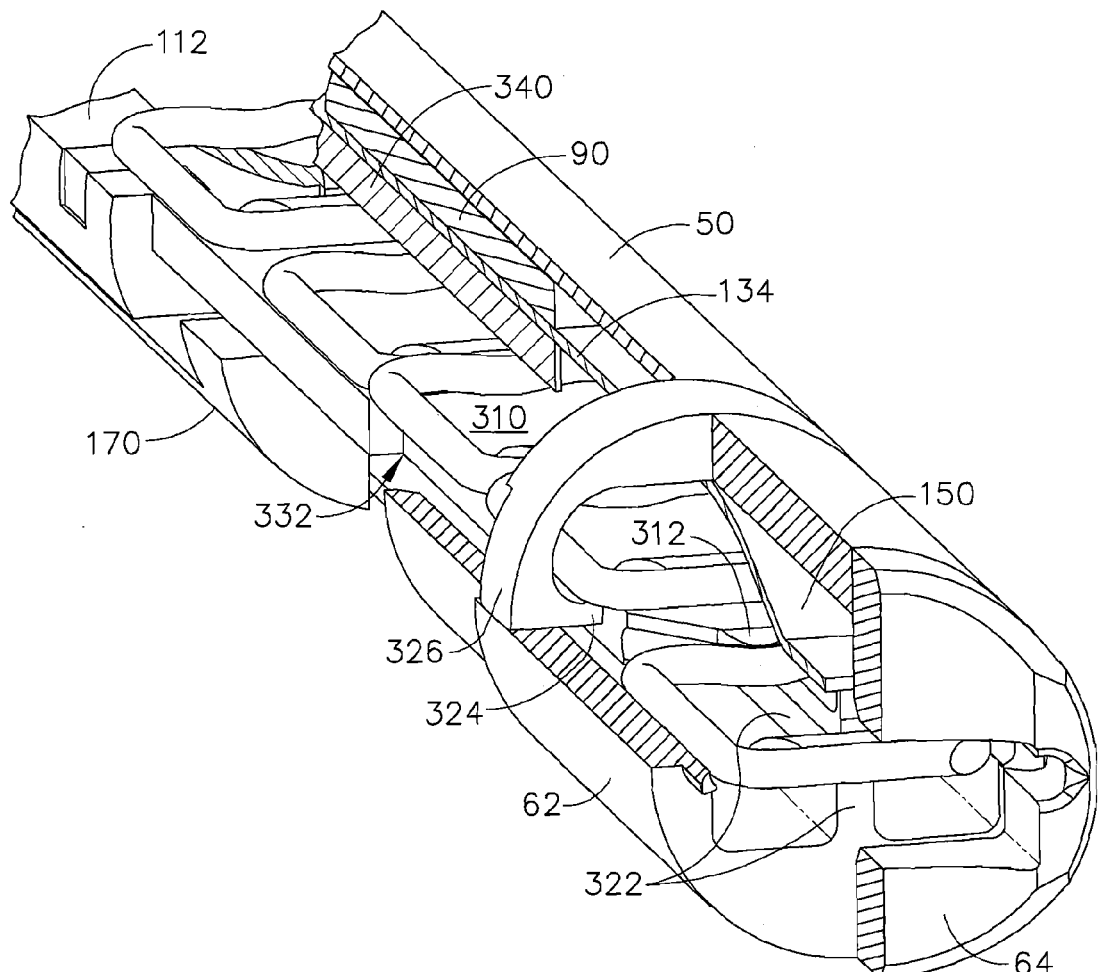
FIG. 81 is an isometric view, partially in section, of the distal stapler end for the embodiment shown in FIG. 74.

In this embodiment, former body 62 is also modified to include lateral shelves 324 for supporting the distal-most staple within the magazine channel. As shown in greater detail in FIG. 80, shelves 324 may be shaped into an inset piece 326 that is positioned into notches 330 (shown in FIGS. 78 and 79) in former body 62, so that the upper surfaces of shelves 324 are coplanar with the upper surface of spreader 310. Shelves 324 are coplanar with the upper, staple holding surface of spreader 310 to provide support for the distal-most staged staple 10 within the magazine channel as the spreader is advanced and retracted beneath the staple stack. Shelves 324 prevent the distal-most staple in the magazine channel from prematurely tilting into the discharge channel during refraction of spreader 310. Shelves 324 enable spreader 310 to be retracted back proximally beyond the distal end of the staple stack, while ensuring proper placement of the staples within the discharge channel. As shown in FIGS. 77 and 81, the longitudinal sides of spreader 310 are partially cutaway, as indicated at 332, to allow the spreader to slide between shelves 324 as the spreader advances and retracts during deployment. While support shelves 324 are shown as part of an inset piece to former body 62, it should be understood that the inset piece (including shelves) could be formed as a unitary piece with the former body 62 without departing from the scope of the invention.

Figure 82:
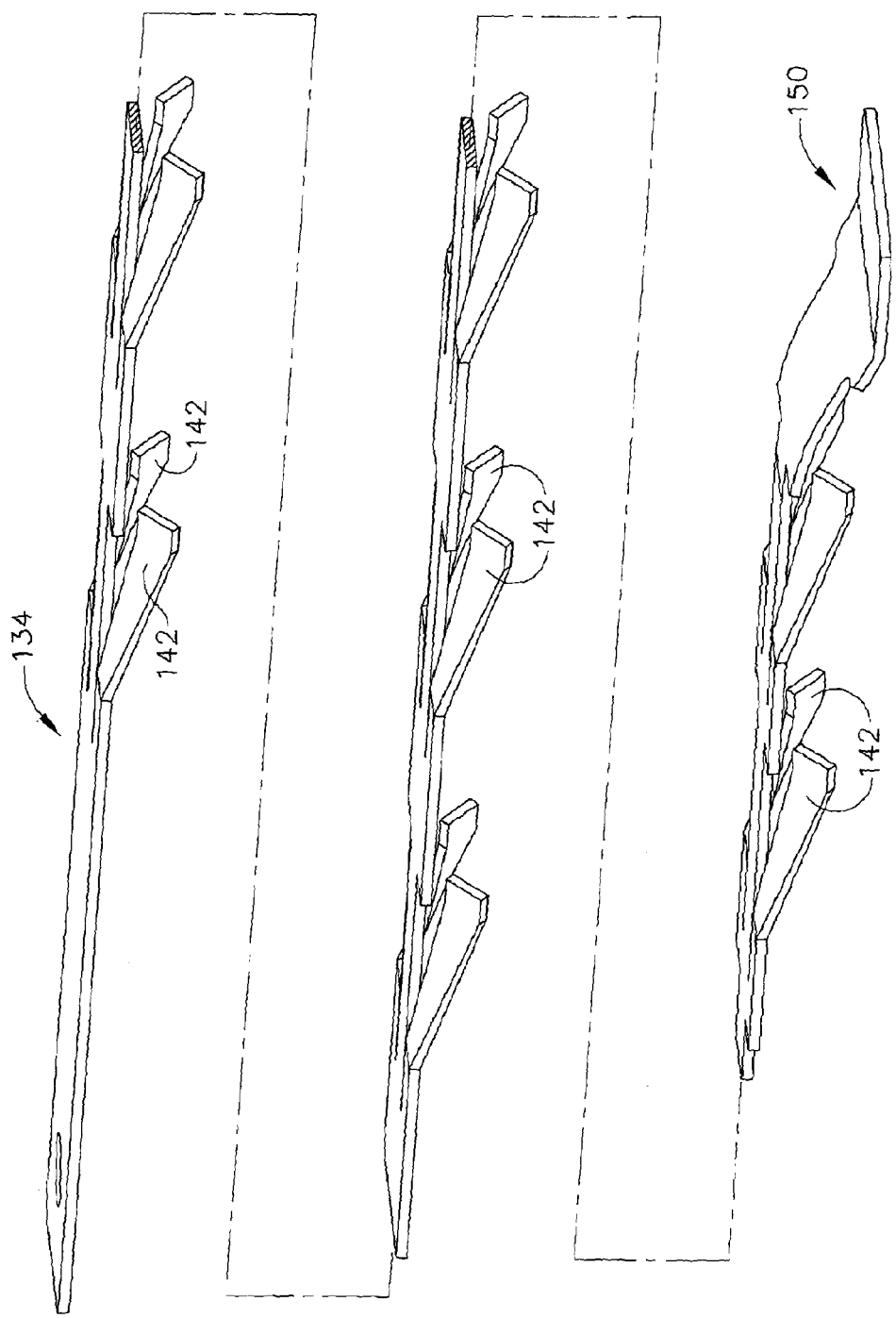
FIG. 82 is an isometric view of an alternative embodiment for the staple indexer.

FIG. 82 shows another possible modification for stapler 40. As shown in this figure, staple indexer 134 is modified to include pairs of staple holding arms 142 distending down from opposite longitudinal sides of the indexer. Each holding arm pair engages a separate staple in stack 100, with the distal ends of the arms contacting the staple end segments adjacent the intersections between the end segments and staple legs. Each of the holding arms 142 may be twisted relative to the plane of the staple indexing body 140 to provide a larger, angled area of contact between the distal end of the arm and the inside of the staple loop. A preferred angle of twisting is approximately 45° from the plane of indexing body 140. Additionally, a center section of staple indexing body 140 may have a length of increased depth forming a spacer 340, as shown in FIGS. 74 and 75. Spacer 340 extends longitudinally above the staple stack 100 and contacts the upper surface of the staples within the stack. Contact between spacer 340 and staple stack 100 inhibits relative vertical movement of the staples within the stack as the stack is indexed within the magazine channel. Shoe 150 may have an opening in a central region (not shown) allowing anvil tines 166 to pass permitting shoe 150 to push the staple more securely against anvil arms 164 and rib 322.

Figure 83:
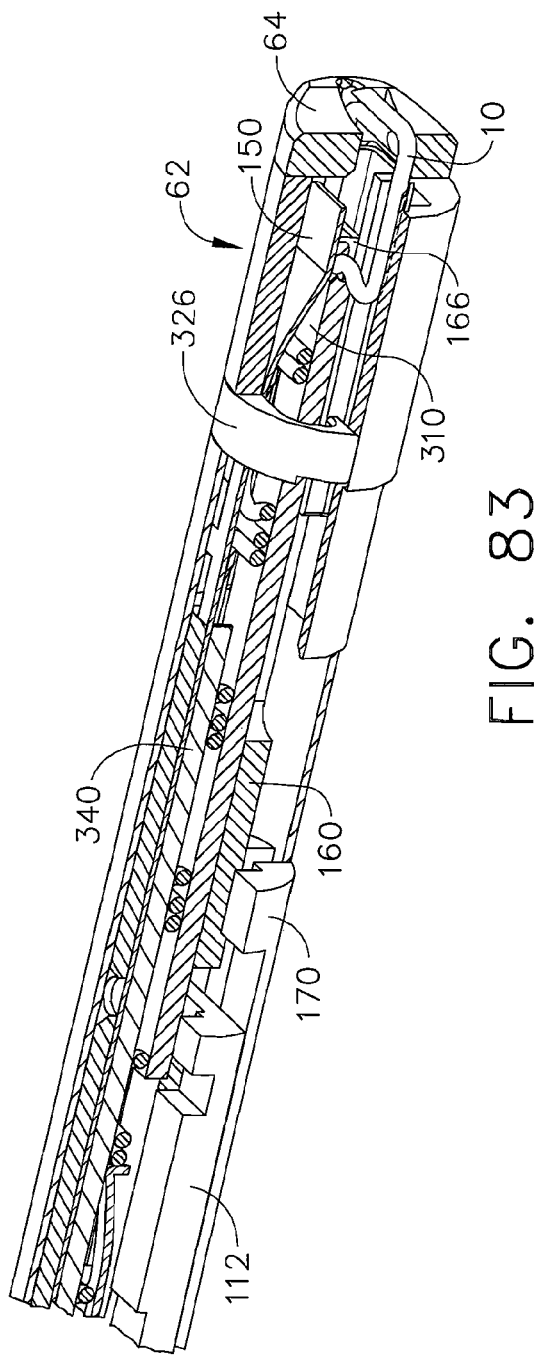
FIG. 83 is an isometric view, partially in section, of the stapler of FIG. 74 shown with the spreader advanced to hold the staple against the anvil tines during the deployment sequence.
Figure 84:
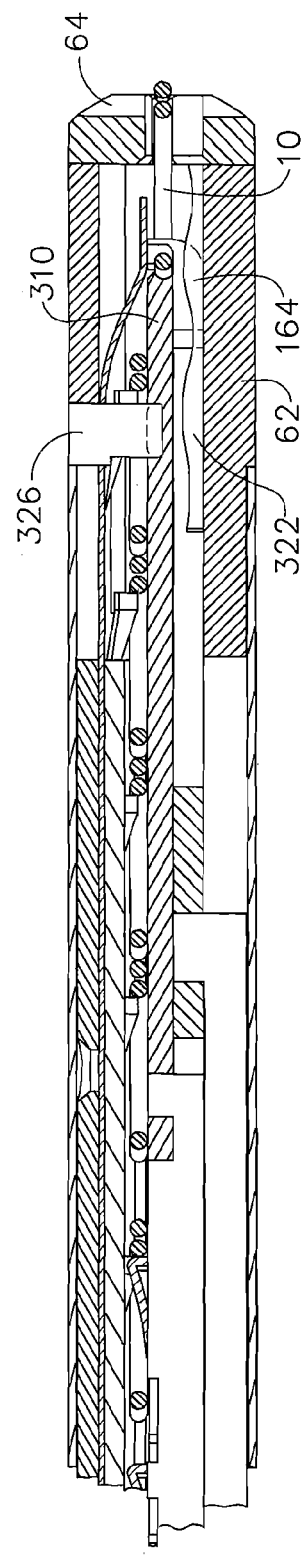
FIG. 84 is a side, partially sectional view of the distal stapler end showing the same deployment stage as FIG. 83.

To deploy a staple 10, the initial trigger 260, defined as the separator trigger in the previous embodiment, is squeezed towards pistol grip 44. The squeezing force rotates the trigger 260 about pivot pin 264, causing the upper trigger lobes to apply a force against separator driver 214, which in turn pushes clamp bushing 204 distally. In this embodiment, bushing 204 pushes clamp extension 112 distally, advancing spreader 310 within the discharge channel. As spreader 310 advances distally, inward radius 314 at the distal spreader end 312 engages the outer circumference of the staged staple and pushes the staple against the proximal face of the anvil tines 166, holding the staple back span fixed between the spreader tip and anvil tines. As initial trigger 260 continues applying force to driver 214, spreader 310 continues pushing against the staple 10, driving the staple and anvil tines 166 forward towards the open stapler end, as shown in FIGS. 83 and 84. As anvil tines 166 and the staged staple 10 progress through the distal stapler opening, the anvil tines remain inwardly biased, adjacent the intersection between the staple legs 14, 16 and back span 12. With staple 10 held outside the open stapler end by spreader 310 and anvil tines 166, anvil stop 224 bottoms out against anvil bushing 220, stopping further distal movement of the anvil 160.

Figure 85:
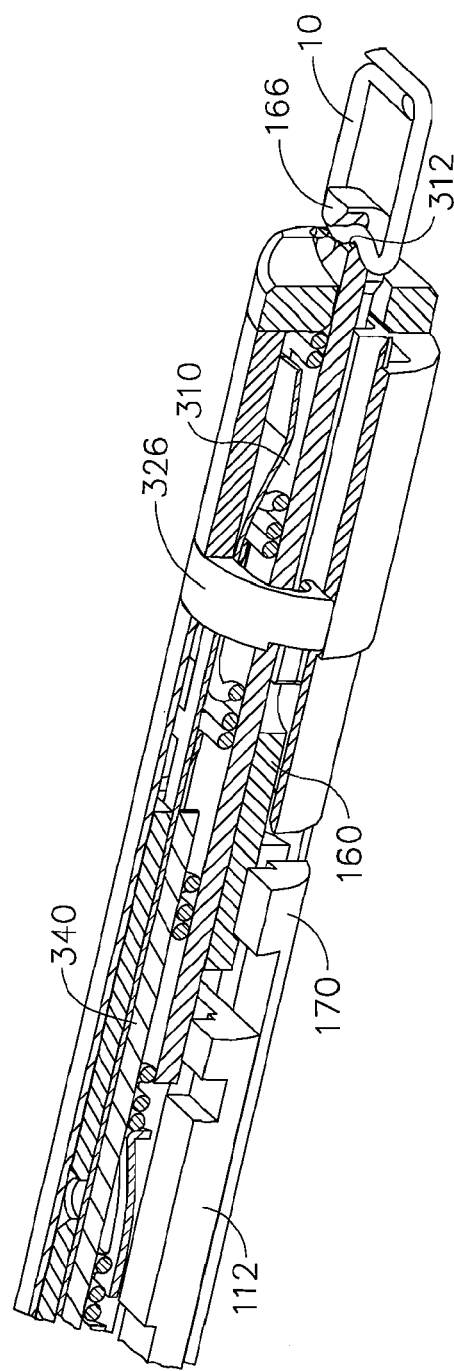
FIG. 85 is an isometric view, partially in section, of the stapler of FIG. 74 shown with the spreader advanced to hold the staple against the anvil tines outside of the stapler.
Figure 86:
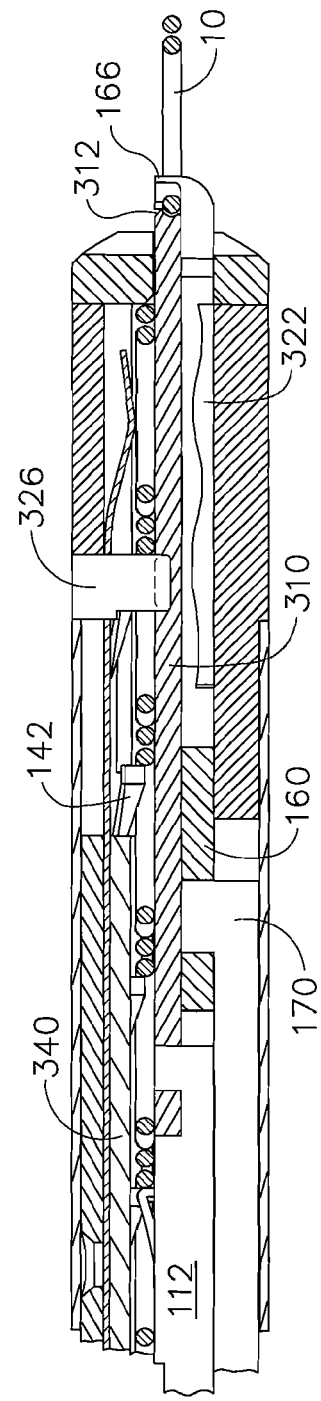
FIG. 86 is a side, partially sectional view of the distal stapler end showing the same deployment stage as FIG. 85.

When anvil 160 reaches its fully distal position, as shown in FIGS. 85 and 86, the back span of staple 10 is firmly held between spreader end 312 and the proximal face of anvil tines 166. After anvil 160 reaches its distal stop, initial trigger 260 continues advancing driver 214 and, thus, spreader 310 relative to the fixed anvil tines. As spreader 310 advances, spreader tip 312 moves between anvil tines 166, pushing the tines outward against the inside edges of staple 10 at the intersections between staple legs 14, 16 and back span 12. The advancing spreader tip 312 applies a distally directed force against depression 30 in staple back span 12 between the anvil tines 166. As shown in FIGS. 87 and 88, the distally directed force of spreader 310 drives anvil arms 164 out laterally and deforms back span 12 between the anvil tines. The deforming force of spreader 310 against the fixed back span 12 drives the anvil tines 166 laterally into staple legs 14, 16, expanding open the staple 10 to the condition shown in FIG. 89. In expanding open, staple 10 bends at two points along base segment 12, with both points occurring opposite the proximal face of anvil tines 166, just inside the intersection between the back span and staple legs 14, 16. As staple 10 is expanding open, staple legs 14, 16 are bent back against the distal angled face of spreader tip 312. The angle at which staple legs 14, 16 bend open can vary, depending in part upon the angle of the spreader distal tip 312 and also on the amount of relative motion between the anvil tines 166 and spreader 310. With staple 10 fully expanded and stabilized between spreader 310 and anvil tines 166, the staple can be pushed forward by stapler 40 to pierce or otherwise engage the intended tissue or other target. As staple 10 expands open, initial trigger 260 pivots to a fully closed position, with pawl 276 engaging latch 274, pausing the deployment process to allow the surgeon to manipulate the open, exposed staple 10 relative to the surrounding tissue or material to insert the prongs 26 at the desired locations.

Figure 93:
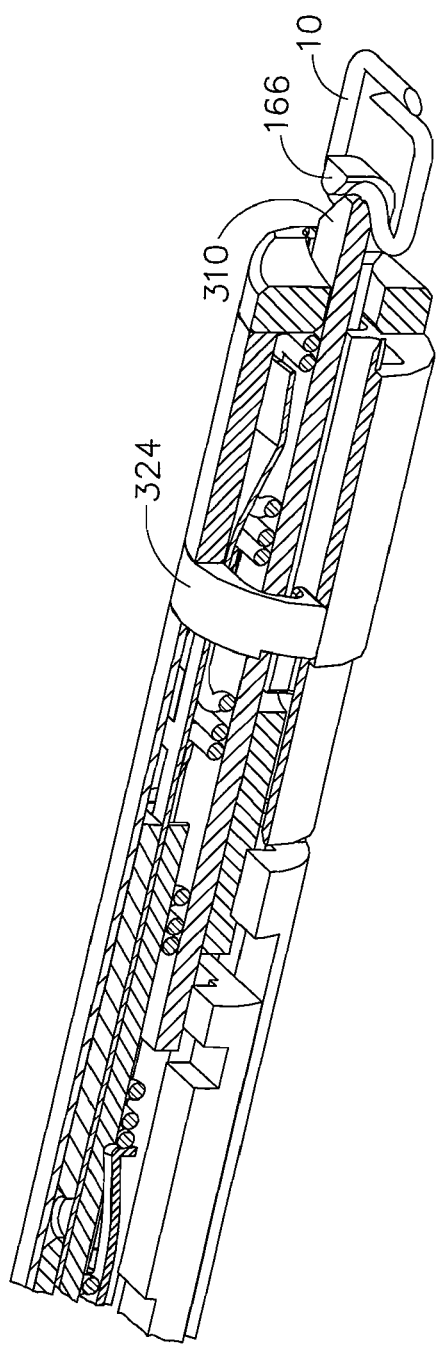
FIG. 93 is an isometric view, partially in section, of the stapler of FIG. 74 shown with the former retracted back from the closed staple.
Figure 94:
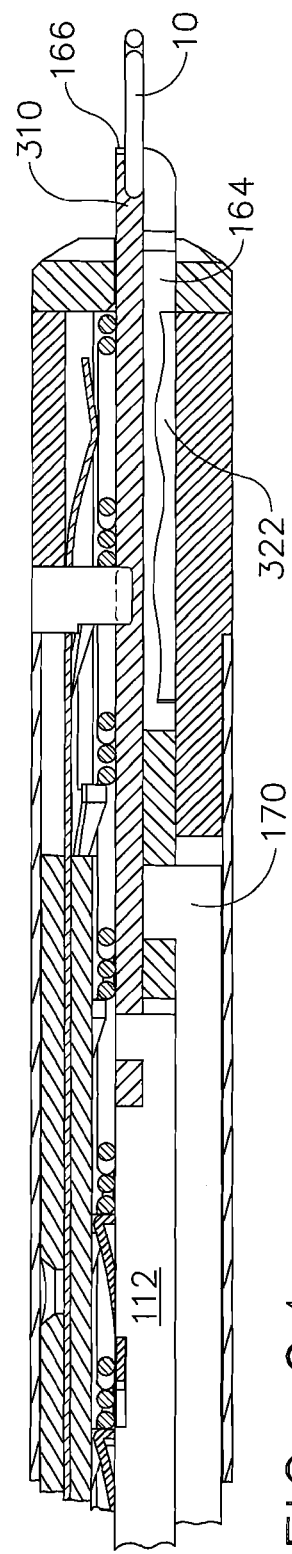
FIG. 94 is a side, partially sectional view of the distal stapler end showing the same deployment stage as FIG. 93.
Figure 95:
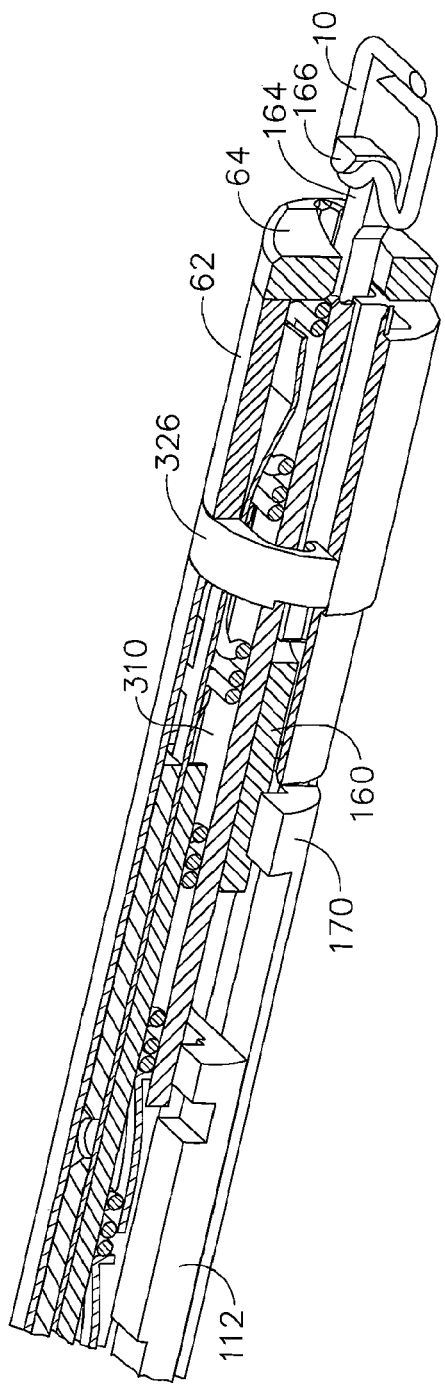
FIG. 95 is an isometric view, partially in section, of the stapler of FIG. 74 shown with the spreader retracted back from the closed staple and anvil tines in preparation for releasing the staple.
Figure 96:
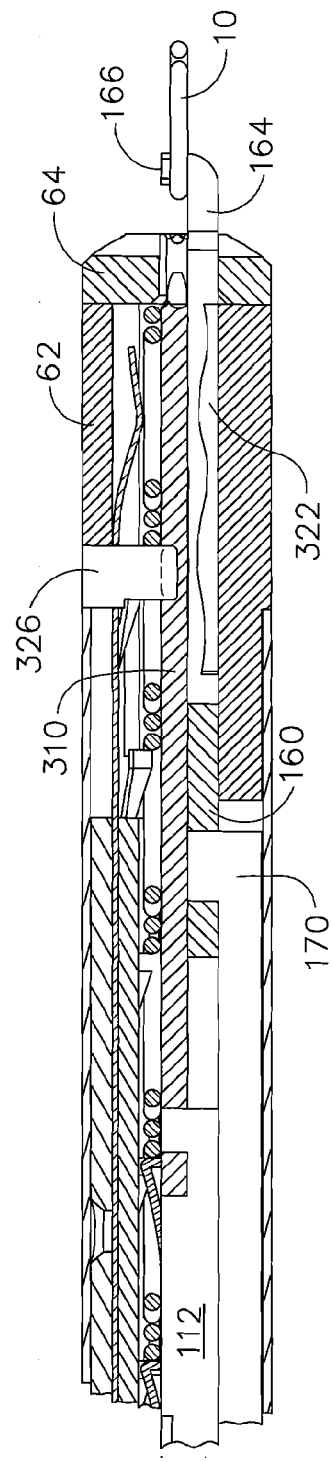
FIG. 96 is a side, partially sectional view of the distal stapler end showing the same deployment stage as FIG. 95.

To close the expanded staple former trigger 262 is squeezed, applying force to former bushing 192 to drive the bushing, housing 50, former body 62 and former end cap 64 distally relative to the fixed, expanded staple 10. The distal movement of former end cap 64 draws end cap grooves 82 against the expanded staple legs 14, 16, as described in the previous embodiment, forcing the staple legs to bend forward about the fixed anvil tines 166 to close the staple 10, as shown in FIGS. 90-92. In this embodiment, the staple former operates in a similar manner to the previously described embodiment in closing the staple. After staple 10 is closed, former trigger 262 is released, allowing the former bushing to retract and draw housing 50, former body 62 and end cap 64 back proximally from the staple, as shown in FIGS. 93 and 94. As the former is drawn proximally, staple 10 remains fixed between spreader 310 and anvil tines 166. As former trigger 262 pivots open, the trigger releases the initial trigger 260, as described above, allowing the trigger upper lobes to push against driver 214 within handle 42 and draw spreader 310 proximally back from staple 10. FIGS. 95 and 96 show spreader 310 retracted back within former body 62. While spreader 310 retracts, anvil 160 remains distal, with the closed staple 10 locked in the tissue (not shown), and held by anvil tines 166 outside the open stapler end. As spreader 310 retracts, anvil arms 164 retract back inward releasing the pressure of anvil tines 166 against staple legs 14, 16. With the outward anvil force removed, staple 10 can be released from the stapler by maneuvering the anvil 160 as needed away from the staple or, optionally, by utilizing staple ejecting members as described above.

Figure 97:
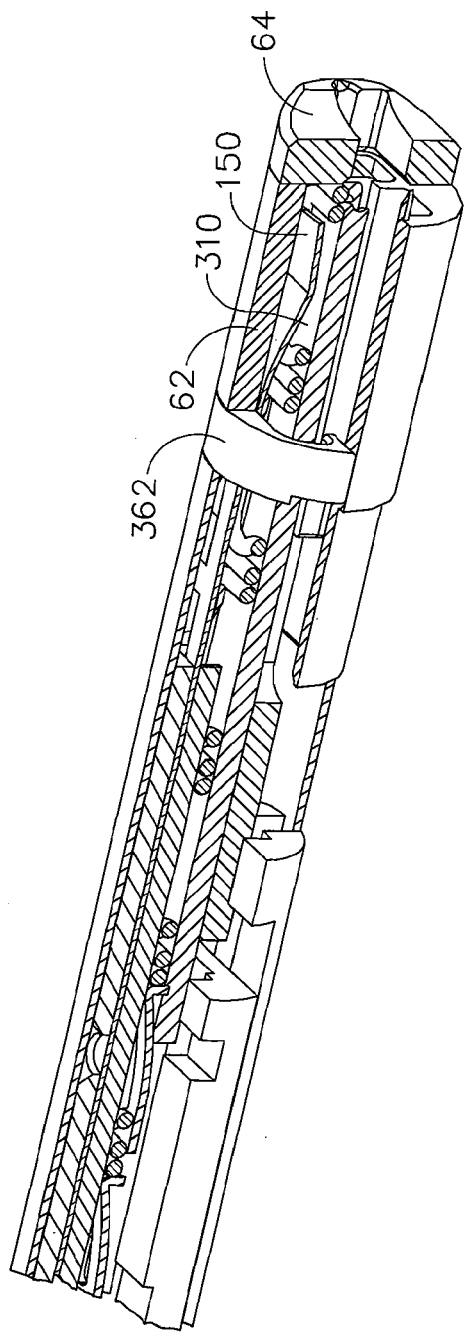
FIG. 97 is an isometric view, partially in section, of the stapler of FIG. 74 shown with the spreader and anvil in a partially retracted position following release of the staple.
Figure 98:
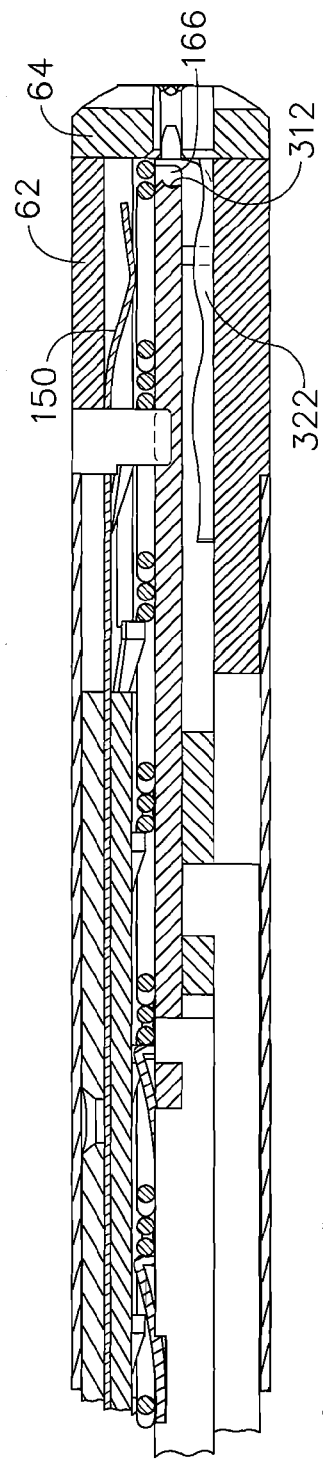
FIG. 98 is a side, partially sectional view of the distal stapler end showing the same deployment stage as FIG. 97.
Figure 99:
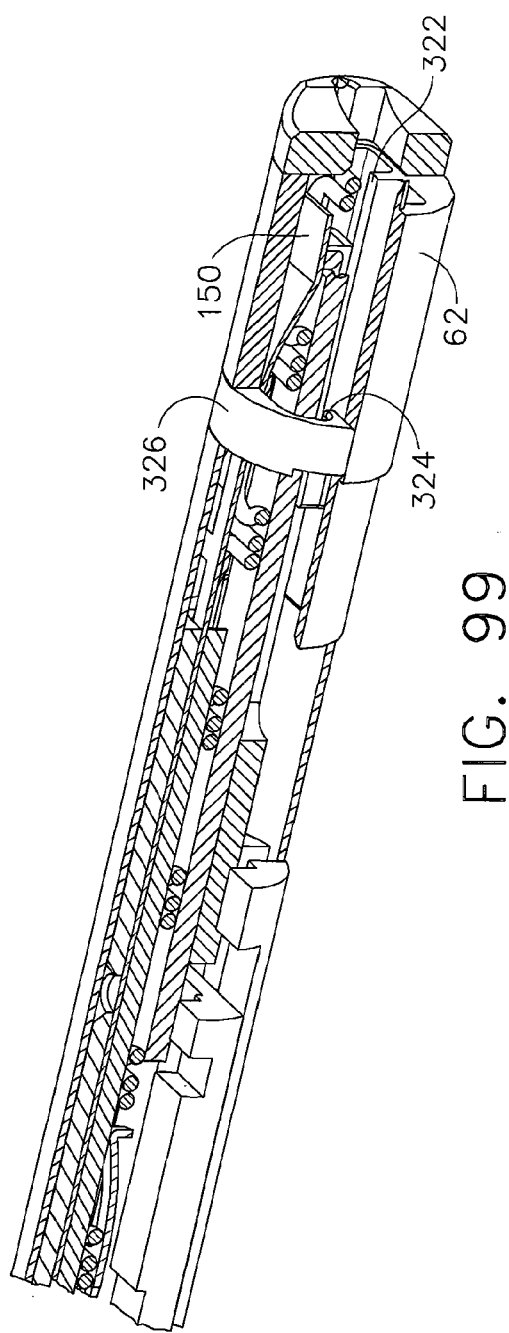
FIG. 99 is an isometric view, partially in section, of the stapler of FIG. 74 shown with the spreader retracting back beneath the staple stack to allow for depositing of the next staple over the anvil tines.
Figure 100:
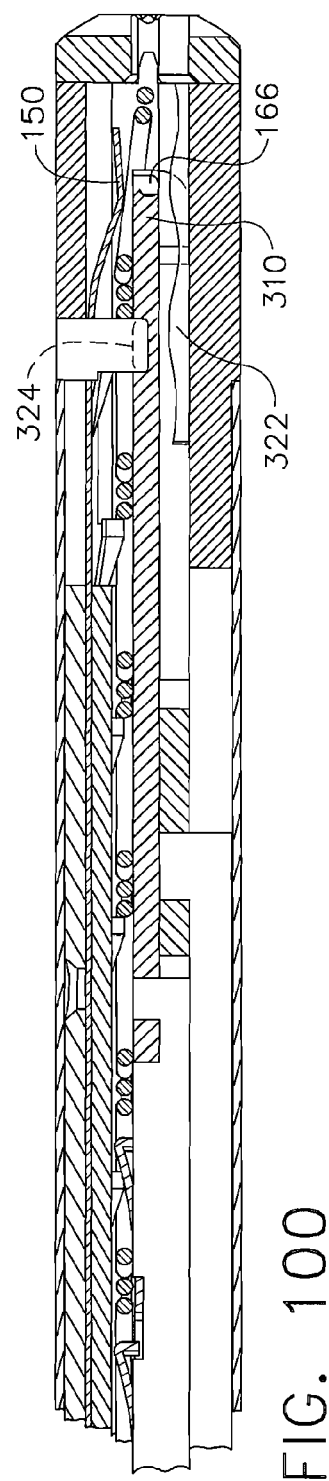
FIG. 100 is a side, partially sectional view of the distal stapler end showing the same deployment stage as FIG. 99.

After staple 10 is released, anvil 160 is drawn back proximally by releasing anvil catch 240 in the manner described above. With anvil catch 240 released, anvil stop 224 moves proximally drawing the attached anvil extension 170 and anvil 160 back within former body 62 and against the face of spreader 310, as shown in FIGS. 97 and 98. While anvil 160 retracts, spreader 310 continues retracting beneath the distal end of staple stack 100. Spreader 310 retracts back to a position proximal of the distal-most staple in stack 100, allowing shoe 150 to push the distal-most staple down into the discharge channel as shown in FIGS. 99 and 100. Spreader 310 is refracted further proximally than anvil tines 166 to provide a gap for the staple back span 12 between the distal spreader tip and anvil tines. Shelves 324 provide support for the second staple in stack 100 as the distal-most staple is deposited by shoe 150 into the discharge channel forward of spreader 310 and over anvil tines 166.

Shelves 324 enable spreader 310 to retract back sufficiently to ensure depositing of the distal-most staple into the discharge channel, yet retain the remaining staple stack in a plane on the surface of the spreader. Rib 322 in former channel 66 supports the distal end (i.e. end segments 20, 22) of the deposited staple within the discharge channel to maintain the staple in a horizontal plane parallel to the surface of spreader 310. Using rib 322 to support staple 10 within the discharge channel maintains the staple in the optimum position for engagement with the distal spreader tip at the commencement of the next deployment sequence.

In this embodiment, the functions of the clamp and separator of the initial embodiment are combined into a single spreader component. To accommodate this change, the stiff separator spring 216 in the handle can be eliminated, as the function of the spring, to drive the separator 180 forward after the clamp 110 has reached a distal stop, is not necessary in this embodiment. Spreader 310 is driven distally by the interaction of the upper lobes of initial trigger 260 with driver 214, which in turn drives the clamp bushing 204 distally. The connection between clamp bushing 204 and the extension 112 (which is connected in this embodiment to spreader 310) enables the distally directed force on bushing 204 to drive the spreader forward against the staple and anvil.

Figure 103:
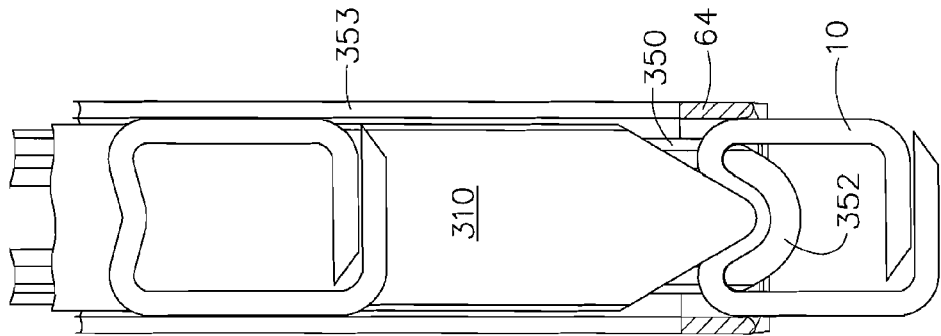
FIG. 103 is a top, partial view of the alternative stapler embodiment of FIG. 101, showing the staple in a closed condition.
Figure 102:
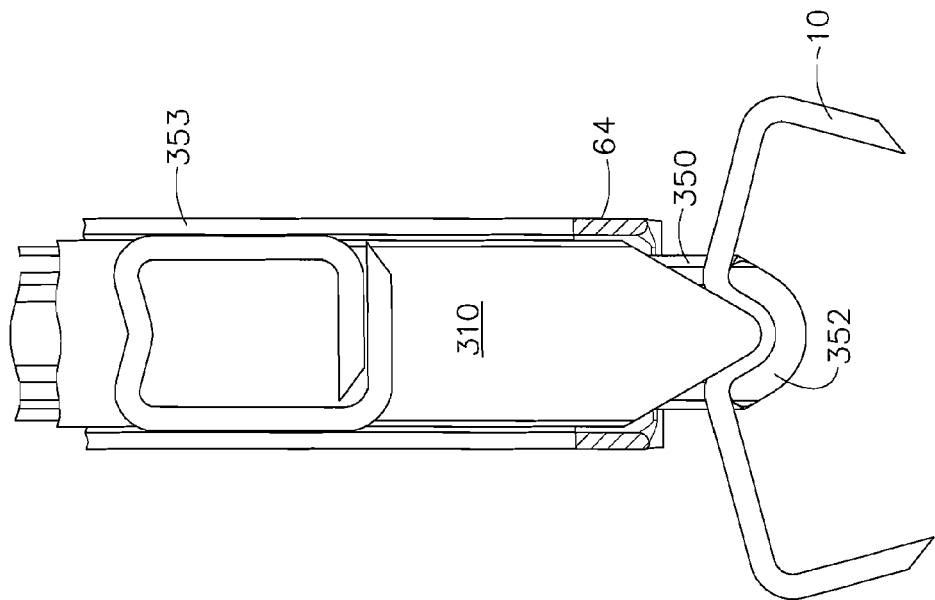
FIG. 102 is a top, partial view of the alternative stapler embodiment of FIG. 101, showing the spreader advanced distally to open the staple.
Figure 101:
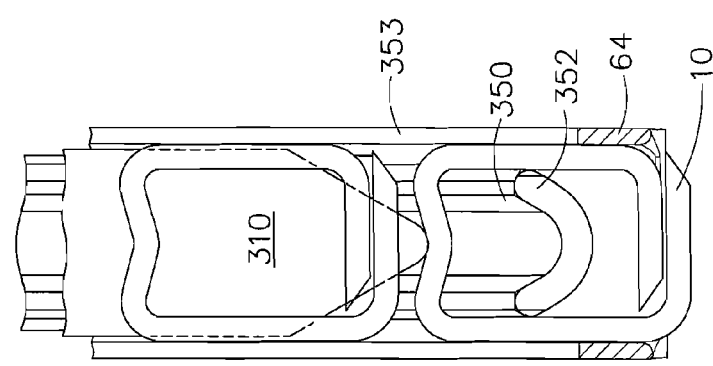
FIG. 101 is a top, partial view of another alternative embodiment for the stapler, showing the staple and spreader in an initial deployment condition.

FIGS. 101 through 103 show another alternative embodiment for stapler 40 in which the anvil 160 with separate, spaced anvil arms 164 is replaced with a single, solid staple support 350 having a continuous staple engaging surface. Support 350 includes a rim 352 extending beyond the surface plane at the distal end of the support. Rim 352 has a rounded distal end for engaging depression 30 in the back span of staple 10. Rim 352 has a radius sized to allow the distal tip of spreader 310 to advance into the proximal contour of the rim to lock the staple back span between the spreader and rim. During the deployment sequence, a staple 10 is deposited on staple support 350 by a shoe or similar (not shown) from previous embodiments with rim 352 extending up through the staple loop, as shown in FIG. 101. During deployment, spreader 310 is advanced against the back span 12 of the staple, while the staple is held against the ends of rim 352 at the intersections between the back span 12 and staple legs 14, 16. As spreader 310 advances, the spreader deforms the staple back span 12 into rim 352, forcing open the staple legs 14, 16 as shown in FIG. 102. After the staple 10 is opened, a former outer tube 353 and former end cap 64 are advanced against the expanded staple legs, as in the previous embodiments, to close the staple about the outer proximal edges of rim 352 as shown in FIG. 103. Ejectoring members similar to springs 296 previously described may be housed in support 350 to facilitate removal of the formed staple from rim 352.

FIGS. 104-106 show the first deployment stage of another alternative embodiment of stapler 40. In this embodiment, staple 10 is reconfigured, as shown in FIG. 104, to include opposing inward depressions 354 extending into the staple loop at the intersection between a substantially linear back span 12 and staple legs 14, 16. Depressions 354 form a reduced width for back span 12 relative to the remaining length of the staple. As shown in FIGS. 105 and 106, this reduced width back span 12 fits within a concave distal end 356 of a modified clamp 110 when the reconfigured staple 10 is deposited over anvil tines 166. Anvil tines 166 are positioned at the junction between depressions 354 and staple legs 14, 16, distal of back span 12. Depressions 354 decrease the width of the proximal staple end to less than the width of the closed anvil tines 166. After staple 10 is deposited in the discharge channel, clamp 110 advances against the back span 12 to hold the staple securely between the clamp and anvil tines 166.

Figure 107:
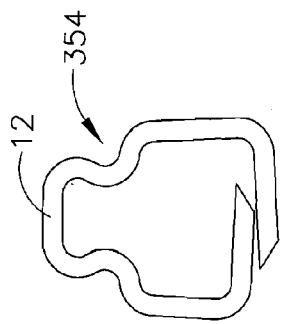
FIG. 107 is a top view of the alternative staple of FIG. 104 showing the staple in a partially open condition.
Figure 108:
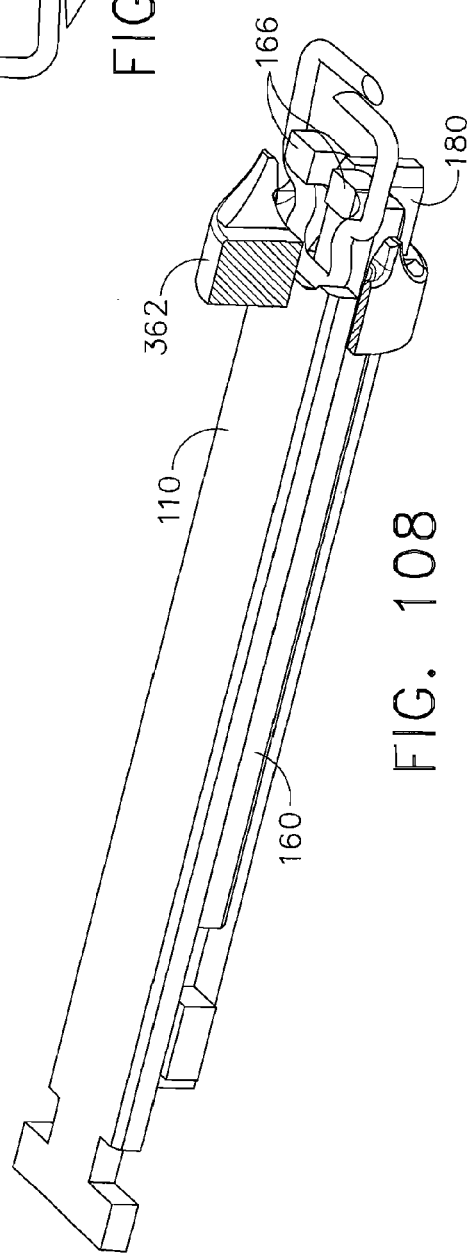
FIG. 108 is a partial, isometric view of the stapler of FIG. 105 showing the spreader advanced between the anvil tines to partially open the staple.
Figure 109:
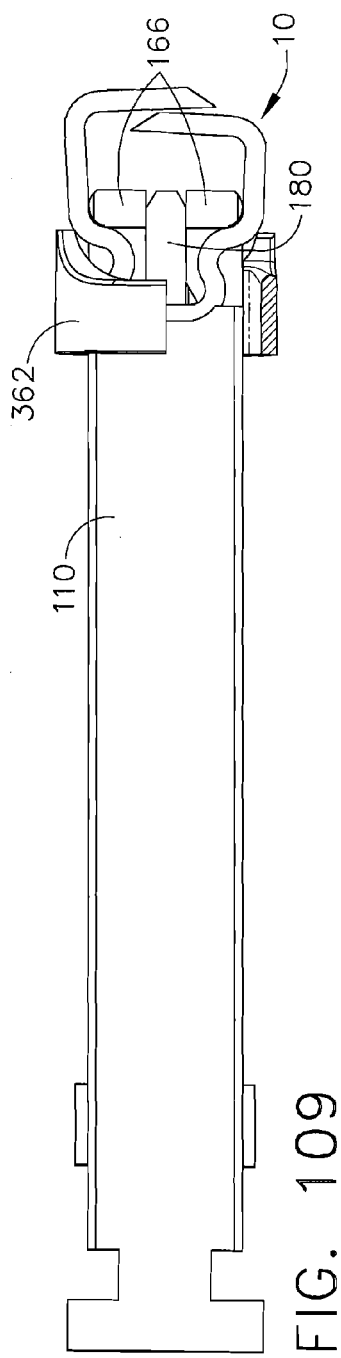
FIG. 109 is a partial, top view of the alternative stapler embodiment and deployment stage shown in FIG. 108.

With staple 10 held fixed, a separator 180 is advanced between anvil arms 164, as in the initial embodiment described above, to drive the anvil tines out laterally against the inner edges of staple legs 14, 16. The force of anvil tines 166 against staple legs 14, 16 in the interior of the staple loop slightly opens the staple (in a range of approximately 10°) from the initial staged condition, as shown in FIGS. 107-109. With separator 180 holding the anvil tines 166 apart, clamp 110 is advanced against staple back span 12. The force of clamp 110 pushing the narrower width, staple back span 12 against the wider, proximal face of anvil tines 166 pulls the staple 10 open at points between the back span and depressions 354, as shown in FIGS. 110-112. As the staple opens, staple legs 14, 16 are bent back proximally, with depressions 354 contacting concave grooves formed in the distal end face of a former 362. With the open staple 10 held fixed between clamp 110, spread anvil tines 166 and former 362, the former is advanced distally against staple legs 14, 16. As former 362 advances, the former bends the staple legs 14, 16 in a distal direction at the junction between the staple legs and depression 354. As staple legs 14, 16 bend forward, end segments 20, 22 move inward and prongs 26 overlap, closing the staple as shown in FIGS. 113-115. As former 362 pushes distally against the curve of depressions 354, the former causes a slight inward overbending of the staple. This overbending of the staple during formation will typically be in the range of 8-10°. As former 362 retracts following staple formation, the staple springs back to a closed, rectangular configuration in which the staple legs are substantially parallel. The interference fit between the former and staple legs thus "stretches" staple 10 as the stapler is being closed, to produce a rectangular, finished shape. Modifying staple 10 and clamp 110, as in this embodiment, decreases the amount of force that is required from the clamp to open the staple. Additionally, the concave shape of the distal clamp end advancing against the fixed, spread anvil tines 166 provides a predictable opening of the staple 10, ensuring consistent results during each staple deployment without setting the corner of the bend as described previously. After staple 10 is closed, former 362, clamp 110 and separator 180 are retracted proximally, as in the previous embodiments, allowing anvil tines 166 to retract inward away from the inside surfaces of staple 10. After anvil 160 retracts, the staple can be released from the stapler as described above.

Figure 71:
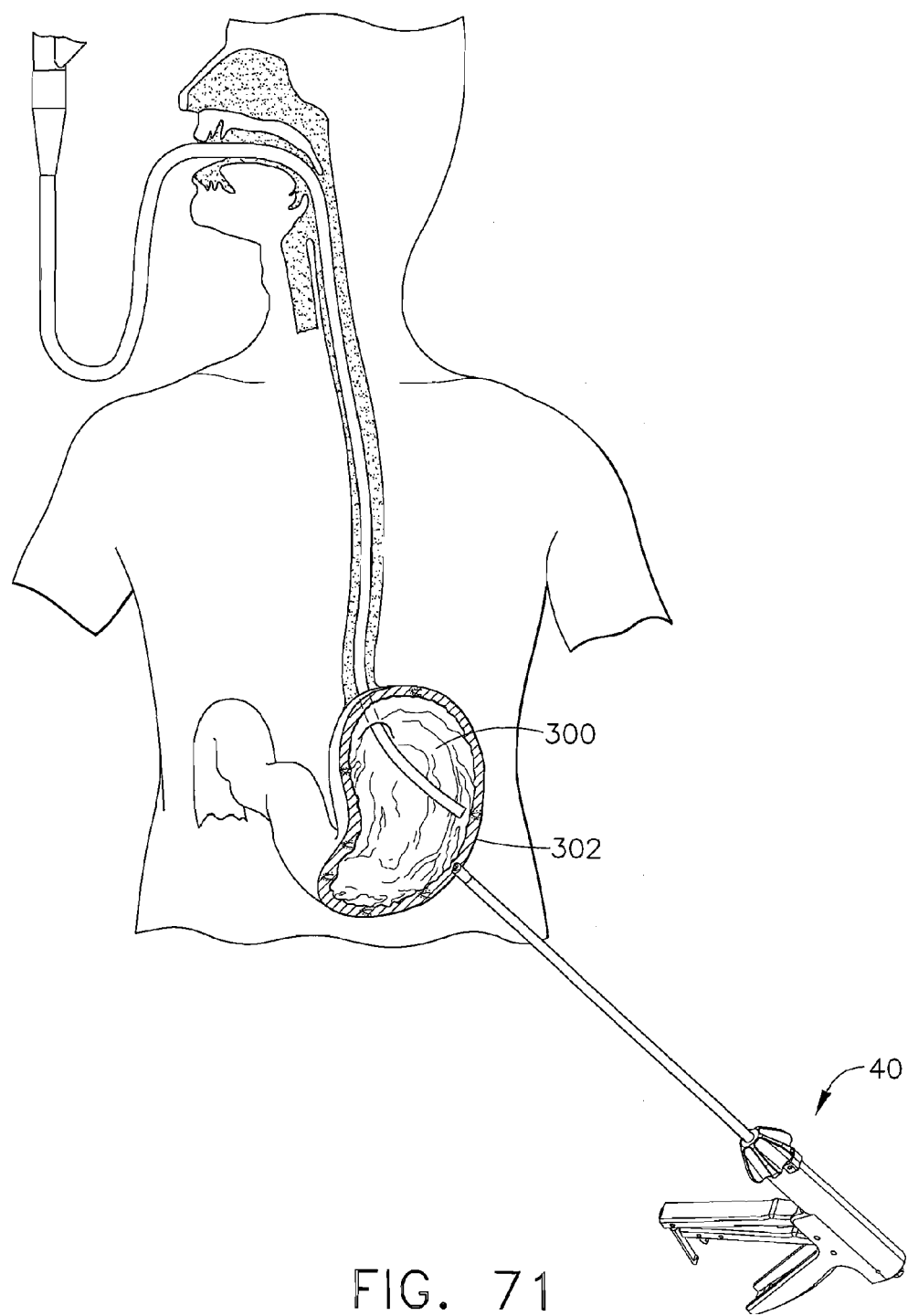
FIG. 71 is a schematic view of a patient during a hybrid endoscopic-laparoscopic procedure.

As mentioned above, one of the many applications for stapler 40 is in a gastric volume reduction (GVR) procedure. In a GVR procedure, such as depicted diagrammatically in FIG. 71, a fold is formed in the wall of the gastric cavity 300. To perform the GVR procedure, a trocar port is inserted through an incision in the abdominal wall. Stapler 40 of the present invention is passed through a trocar port (e.g., a single port abdominal trocar, an abdominal trocar containing multiple ports, a transvaginal trocar port, etc.) and into the peritoneal cavity. In addition to stapler 40, other instruments may be inserted through the abdominal wall or other access means to facilitate the procedure. In a preferred procedure, the greater curvature of the stomach is freed of connection points such as the omentum and short gastric vessels via standard dissection means and the targeted fold is about the greater curvature of the stomach. With stapler 40 inside the cavity, pressure is applied to actuator assembly 46 to advance a staple 10 outside the open end of the stapler. Staple legs 14, 16 are expanded open outside the stapler, so that prongs 26 face forward towards the cavity wall. With staple legs 14, 16 open, stapler 40 can be manipulated to grab, pierce, or otherwise engage sections of the cavity wall 302 with prongs 26. Graspers or other tissue manipulation devices may aid in the positioning of tissue or other targets. As the staple prongs grab onto separate wall sections, the sections are drawn together to appose the serosal tissue between the staple legs. As the sections are drawn together, the tissue involutes inward into cavity 300 forming a fold. With the tissue sections folded and held by prongs 26, additional pressure can be applied to actuator assembly 46 to form the staple 10 through the tissue. As staple 10 is being closed by the former, prongs 26 and staple end segments 20, 22 draw together within the cavity wall to secure the tissue sections together.

After the staple 10 is formed through the tissue to hold the fold in place, actuator assembly 46 is released to eject the staple from the stapler. After the first staple is deployed, stapler 40 is preferably moved to a second location on the cavity wall along the intended fold line. Additional staples are preferably deployed along the cavity wall to extend the length of the fold. Additional details regarding GVR procedures and the use of a stapling device, such as the staple deploying device of the present invention, in a GVR procedure; as well as other surgical applications for the stapling device of the present invention, can be found in commonly assigned U.S. patent application Ser. No. 12/359,351, which was previously incorporated by reference into this application.

In these procedures the infolded tissue may develop edema. This edema or swelling of the fold may have the potential to temporarily block or obstruct the gastric lumen if the fold was not properly sized by the surgeon. This edema dissipates in a few days time. Accounting for the edema requires the surgeon to create a smaller fold that is less restrictive once the edema has subsided. Implanting a device such as a stent into the region of the fold allows the surgeon to create a more restrictive fold with the stent maintaining a patent lumen while the edema is present. After the edema subsides, a patent lumen remains that does not require scaffold provided by the stent. The stent may be a permanent implant, but is preferably removable, digestible, or otherwise absorbable. The stent may also be designed to be passed naturally after some degradation. One example of a stent that may be applicable is the Polyflex® Esophageal Stent available from Boston Scientific Corporation, Natick, Massachussetts. Stents such as these are known in the art and are designed to maintain luminal patency.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, ethylene oxide (EtO) gas, or high-energy electrons. The radiation kills bacteria on the instrument and in the container. The sterilized instrument can then be stored in the sterile container. The sealed container keeps the instrument sterile until it is opened in the medical facility.

Any patent, publication, application or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The foregoing description of preferred embodiments of the invention has been presented for purposes of illustration and description. It is not intended to be exhaustive or to limit the invention to the precise form disclosed. Obvious modifications or variations are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed:

1. A method of deploying a surgical fastener comprising the steps of:
    a. introducing said fastener into a body of a patient while said fastener is in a first shape comprising a first loop having a back span with an original size and shape;
    b. moving end segments of said fastener away from each other substantially along an entire length thereof while keeping said back span in substantially its original size and shape; and
    c. forming said fastener into a second loop having a width greater than a width of said first loop.

2. The method of claim 1 wherein said step of forming said fastener into a second loop having a width greater than a width of said first loop also comprises the step of keeping said back span in substantially its original size and shape.

3. The method of claim 1 further wherein the step of introducing said fastener comprises the step of providing a fastener comprising:
    a. a base, and two legs extending away from said base, said legs having distal end segments;
    b. a first shape wherein said distal end segments bend towards each other in so that they are adjacent and form said fastener into a first loop;
    c. a second shape wherein said distal end segments are spaced apart from each other along substantially an entire length thereof; and
    d. a third shape wherein said distal end segments bend towards each other in so that they are adjacent and form said fastener into a second loop, said second loop having a width greater than a width of said first loop.

4. The method of claim 1 wherein said step of forming said fastener comprises approximating tissue locations separated by a distance larger than a maximum width between said end segments of said fastener.

5. The method of claim 4 further comprising moving said tissue locations by said end segments of said fastener.

6. The method of claim 4 further comprising moving said tissue locations by using at least one additional tissue manipulator.

7. A method of deploying a surgical fastener comprising the steps of:
    a. introducing said fastener into a body of a gastric cavity of a patient while said fastener is in a first shape comprising a first loop having a back span with an original size and shape;

b. moving end segments of said fastener away from each other substantially along an entire length thereof while keeping said back span in substantially its original size and shape; and c. forming said fastener around gastrointestinal tissue into a second loop having a width greater than a width of said first loop.

8. The method of claim 7 said step of forming said fastener around gastrointestinal tissue comprises creating a plication of gastric tissue and reducing a stomach capacity.

9. The method of claim 7 further comprising securing an implantable material to a tissue of a patient.

10. The method of claim 7 further comprising the step of introducing a therapeutic agent into a patient via said fastener.

* * * * *